United States Patent
Kim et al.

(10) Patent No.: US 10,620,215 B2
(45) Date of Patent: *Apr. 14, 2020

(54) REAL-TIME IMAGING SENSOR FOR MEASURING CELLULAR THIOL LEVEL

(71) Applicants: CELL2IN, INC., Seoul (KR); KOREA UNIVERSITY RESEARCH AND BUSINESS FOUNDATION, Seoul (KR); SNU R&DB FOUNDATION, Seoul (KR)

(72) Inventors: In-Gyu Kim, Incheon (KR); Ki Hang Choi, Seoul (KR); Eui Man Jeong, Seoul (KR); Heun Soo Kang, Gyeonggi-do (KR)

(73) Assignees: Cell2In, Inc. (KR); Korea University Reserach and Business Foundation (KR); SNU R&DB Foundation (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/238,371

(22) Filed: Jan. 2, 2019

(65) Prior Publication Data

US 2019/0204331 A1 Jul. 4, 2019

Related U.S. Application Data

(63) Continuation of application No. 15/527,816, filed as application No. PCT/KR2015/012415 on Nov. 18, 2015, now Pat. No. 10,215,757.

(30) Foreign Application Priority Data

Nov. 19, 2014 (KR) .......................... 10-2014-0161860

(51) Int. Cl.
*G01N 33/58* (2006.01)
*G01N 33/50* (2006.01)
*C07D 491/16* (2006.01)

(52) U.S. Cl.
CPC ......... *G01N 33/582* (2013.01); *C07D 491/16* (2013.01); *G01N 33/5008* (2013.01); *G01N 33/5091* (2013.01); *G01N 2800/7009* (2013.01); *G01N 2800/7042* (2013.01)

(58) Field of Classification Search
CPC ................................ G01N 33/50; G01N 33/58
See application file for complete search history.

(56) References Cited

U.S. PATENT DOCUMENTS 1,021,575 A1 2/2019 Kim et al.

FOREIGN PATENT DOCUMENTS

| KR | 10-1328000 | 11/2013 |
| KR | 10-1337434 | 12/2013 |

OTHER PUBLICATIONS

Cho, A. Y. et al., "A Coumarin-based Fluorescence Sensor for the Reversible Detection of Thiols", Chemistry letters, 2012, vol. 41, No. 12, pp. 1611-1612.
Jung, H.S. et al., "Recent Progress in Luminescent and Colorimetric Chemosensors for Detection of Thiols", Chem. Soc. Rev., 2013, vol. 42, No. 14, pp. 6019-6031.
Kwon, H. et al., "Coumarin-Malonitrile Conugate as a Fluorescence Turn-On Probe for Biothiols and Its Cellular Expression", Chemical Communications, 2011, vol. 47, No. 6, pp. 1773-1775.
Seoul National University R&DB Foundation, Final Report of Convergent Translational Research Center for the Development of Pulmonary Fibrosis Therapeutics (H11000185), Aug. 24, 2014.
Wu et al. "Reversible Fluorescent Probe for Highly Selective and Sensitive Detection of Mercapto Biomolecules," Inorganic Chemistry, 2011, vol. 50, pp. 6543-6551.
International Search Report prepared by the Korean Intellectual Property Office dated Jul. 27, 2016, for International Application No. PCT/KR2015/012415.
Official Action for U.S. Appl. No. 15/527,816, dated May 17, 2018 11 pages Restriction Requirement.
Notice of Allowance for U.S. Appl. No. 15/527,816, dated Oct. 4, 2018 9 pages.

*Primary Examiner* — Michael G. Hartley
*Assistant Examiner* — Jagadishwar R Samala
(74) *Attorney, Agent, or Firm* — Sheridan Ross P.C.

(57) ABSTRACT

The present invention relates to a fluorescence sensor capable of real-time imaging for measuring a cellular thiol level. The present invention reveals that the fluorescence intensity of the fluorescent real-time SH group-tracer (FreSH-Tracer) of the present invention increases or decreases continuously, ratiometrically or reversibly depending on the thiol level in living cells, and thus can be usefully used as a biosensor which is remarkably susceptible to quantitative or qualitative real-time detection of the cellular thiol level in living cells.

12 Claims, 46 Drawing Sheets

| Thiol compound | Structure | $K_d$ (mM) |
|---|---|---|
| Glutathione | 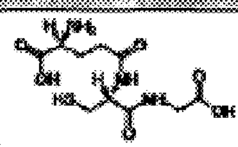 | $3.6 \pm 0.3$[ref] |
| Cysteine | 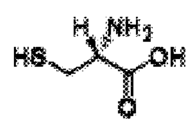 | $10.0 \pm 0.7$[ref] |
| Cysteamine | 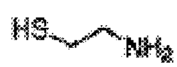 | $2.2 \pm 0.4$ |
| β-mercaptoethanol | 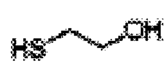 | $6.5 \pm 0.5$[ref] |
| Dithiothreitol | 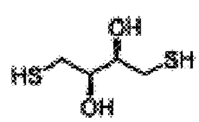 | $1.9 \pm 0.2$ |
| N-acetyl cysteine | 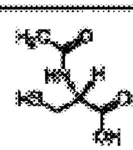 | $2.0 \pm 0.4$ |

FreSH-tracer            The stable mono bond form of FreSH-tracer

REAL-TIME IMAGING SENSOR FOR MEASURING CELLULAR THIOL LEVEL

CROSS REFERENCE TO RELATED APPLICATIONS

This application is a continuation of U.S. patent application Ser. No. 15/527,816, filed May 18, 2017, which is a national stage application under 35 U.S.C. 371 and claims the benefit of PCT Application No. PCT/KR2015/012415 having an international filing date of 18 Nov. 2015, which designated the United States, which PCT application claimed the benefit of Korean Patent Application No. 10-2014-0161860 filed 19 Nov. 2014, the disclosure of each of which are incorporated herein by reference.

TECHNICAL FIELD

Background Art

Intracellular thiols such as cysteine (Cys), homocysteine (Hcy) and glutathione (GSH) play many crucial roles in many physiological matrices. For example, Cys and Hcy are essential biological molecules required for the growth of cells and tissues in living systems. A deficiency of cysteine causes various health problems such as retarded growth, hair depigmentation, lethargy, liver damage, muscle and fat loss, and skin lesions. An elevated level of Hcy in human plasma is a risk factor for Alzheimer's disease, cardiovascular disease, neural tube defect, inflammatory bowel disease, and osteoporosis.

The human body maintains homeostasis by properly eliminating reactive oxygen species (ROS) through the activity of the antioxidant systems. However, when the balance between ROS production and the activity of the antioxidant systems is destroyed, oxidative stress increases, which has recently received attention as the primary common cause of development of aging, age-related degenerative diseases, including degenerative arthritis, cataract and Alzheimer's disease, various cancers, fibrosis diseases, as well as metabolic syndromes, including diabetes, obesity and cardiovascular diseases. The ROS are unstable and highly reactive molecules that oxidize biological molecules to cause biochemical and physiological damage, which is one of the major mechanisms of aging. Thus, not only the degree of oxidation in the human body, but also the degree of antioxidation or antioxidant activity can be used as major markers for measuring biological age.

GSH, which is the most abundant intracellular non-proteinogenic thiol, plays a pivotal role in maintaining the reducing environment in cells and acts as a redox regulator. Specifically, GSH in the human body eliminates various peroxides, including $H_2O_2$, and is oxidized into GSSG to regulate the degree of oxidation/reduction to thereby maintain redox homeostasis. Thus, GSH can be considered a major factor that maintains antioxidant activity and, at the same time, an optimal marker that indicates the degree of antioxidation in the human body. In fact, it was demonstrated by a number of publications that the levels of GSH in animals, including *C. elegans, Drosophila melanogaster*, mice and rats, and various human organs, including brain, heart, kidney, eye lens, lung and blood, decrease with age[1]. In addition, it is known that vitamin C, vitamin E or methionine, which is known to be highly reactive with ROS, does not react with specific ROS such as $H_2O_2$ or superoxide, but the thiol group of GSH can react with all ROS[2]. Furthermore, GSH removes toxic substances from cells by glutatathione S-transferase (GST) activity (detoxification), and when GSH is oxidized into GSSG, it changes the function of protein by direct glutathionylation of protein thiol (PSH) to thereby cause signaling (redox signaling).

Taking the foregoing together, detection and identification of a thiol-containing substance in a biological sample is very important. Until now, several thiol detection methods, including HPLC, capillary electrophoresis and UV-Vis detection/spectrophotometry, have been developed. Although such methods are useful for monitoring thiols in lysed biological samples, a method capable of detecting thiols in living cells has not been reported. To detect thiols in a simple, sensitive and effective manner without lysing cells, fluorescence-based methods are more preferable. For the past years, various fluorescent probes for thiols have been developed which are based on mechanisms such as Michael addition, disulfide bond exchange, Se—N bond cleavage, metal ion/sulfur interaction, or ring formation using aldehyde. However, all the thiol probes developed to date react irreversibly with thiols, and thus cannot be used to observe in real-time the change in the levels of thiols in living cells.

Throughout the specification, a number of publications and patent documents are referred to and cited. The disclosure of the cited publications and patent documents is incorporated herein by reference in its entirety to more clearly describe the state of the related art and the present invention.

DISCLOSURE

Technical Problem

The present inventors have found that the fluorescence intensity of a FreSH-tracer (Fluorescent Real-time SH group-tracer) according to the present invention changes continuously, ratiometrically and reversibly depending on the level of thiols in living cells and that the FreSH-tracer can be effectively used as a highly sensitive biosensor for quantitatively or qualitatively detecting the level of thiols in living cells in real time, thereby completing the present invention.

Therefore, it is an object of the present invention to a composition for detecting thiols in living cells, comprising a FreSH-tracer (Fluorescent Real-time SH group-tracer).

Another object of the present invention is to provide a sensor for detecting thiols in living cells, comprising the FreSH-tracer.

Still another object of the present invention is to provide a kit for diagnosing a disease caused by oxidative stress, comprising the FreSH-tracer.

Still another object of the present invention is to provide a method of screening a thiol enhancer or inhibitor in living cells by use of the FreSH-tracer.

Still another object of the present invention is to provide a composition for measuring antioxidant activity in living cells, comprising the FreSH-tracer.

Yet another object of the present invention is to provide a method of measuring antioxidant activity in living cells by use of the FreSH-tracer.

These and other objects and advantages of the present invention will become more apparent from the following detailed description of the invention and the appended claims.

Technical Solution

In accordance with one aspect of the present invention, there is provided a composition for detection of thiols in living cells, comprising a compound represented by the following formula 1 or a salt thereof:

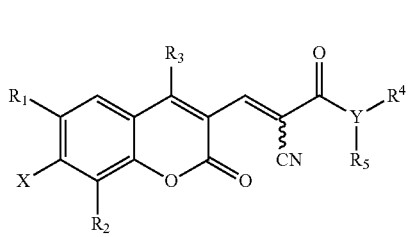

Formula 1 wherein $R_1$ and $R_2$ are each independently hydrogen or $C_{1-4}$ straight-chain or branched alkyl, or $R_1$ and $R_2$ together with X form a five- or six membered heterocycloalkyl or heterocycloalkenyl ring; $R_3$ is hydrogen or $C_{1-4}$ straight-chain or branched alkyl; $R_4$ and $R_5$ are each independently hydrogen, $C_{1-5}$ straight-chain or branched alkyl, or —$(CH_2)_m$—COO—$C_{1-5}$ straight-chain or branched alkyl (where m is an integer ranging from 1 to 5), or $R_4$ and $R_5$ together with Y form a $C_{3-7}$ heterocycloalkyl which may be unsubstituted or substituted with $R_6$; $R_6$ is —COO$(CH_2)_n$—OCO—$C_{1-5}$ straight-chain or branched alkyl (where n is an integer ranging from 1 to 5), —(CONH)—$(CH_2)_o$—$PPh_{3+}Cl^-$ (where o is an integer ranging from 1 to 5), or —(CONH)—$CHR_7$—COO$(CH_2)_p$—OCO—$C_{1-5}$ straight-chain or branched alkyl (where p is an integer ranging from 1 to 5); $R_7$ is —$(CH_2)_q$—COO$(CH_2)_r$—OCO—$C_{1-5}$ straight-chain or branched alkyl (where q and r are each an integer ranging from 1 to 5); and X and Y are each independently N or O.

The present inventors have made extensive efforts to develop a highly sensitive biosensor for quantitatively or qualitatively detecting the level of thiols in living cells in real time. As a result, the present inventor have found that the fluorescence intensity of a FreSH-tracer (Fluorescent Real-time SH group-tracer) according to the present invention changes continuously, ratiometrically and reversibly depending on the level of thiols in living cells and that the FreSH-tracer can be effectively used as a highly sensitive biosensor for quantitatively or qualitatively detecting the level of thiols in living cells in real time.

As used herein, the term "FreSH-tracer (Fluorescent Real-time SH group-tracer)" means the compound represented by formula 1, which is a coumarin derivative having a cyanoacrylamide electrophile and is used as a fluorescent substance for detection of thiols in the present invention.

As used herein, the term "ratiometric" means that output is directly proportional to input. In an embodiment of the present invention, the term "ratiometric" means that the fluorescence intensity of the composition of the present invention changes in direct proportion to the input of thiols.

As used herein, the term "detection" means measuring the presence or level of chemical species or biological substances in a sample.

As used herein, the term "reversible" means a state in which a mixture of a reactant and a product in a chemical reaction can produce an equilibrated mixture. More specifically, the term "reversible" means that the compound represented by formula 1 can react reversibly with thiols in an equilibrium state in a forward or reverse direction depending on the amount of the thiols.

In an embodiment of the present invention, the compound represented by formula 1 is a compound selected from the group consisting of compounds represented by the following formulas 2 to 8:

Formula 2

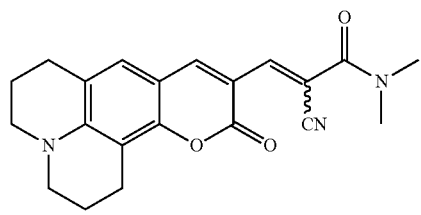

Formula 3

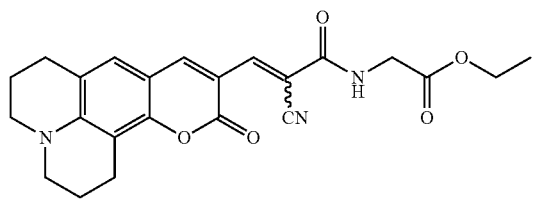

Formula 4

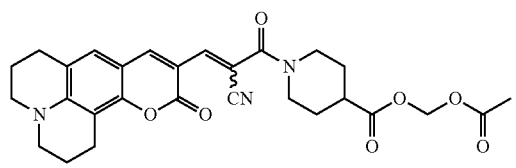

Formula 5

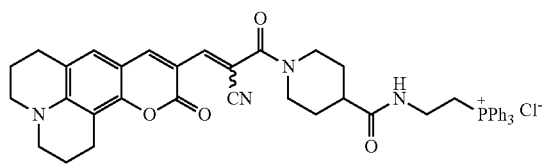

Formula 6

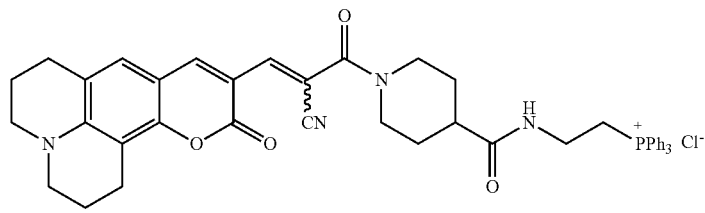

-continued

Formula 7

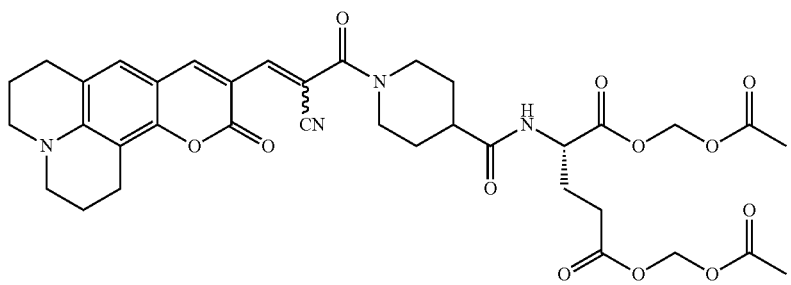

Formula 8

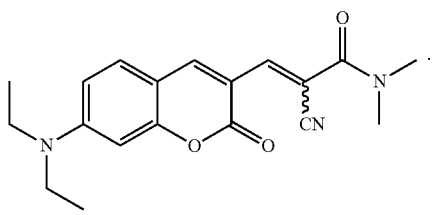

The amount of thiols binding to the compound (FreSH-tracer) represented by formula 1 according to the present invention increases as the amount of thiols in living cells increases. Thus, the fluorescence intensity at 550-680 nm, which is exhibited by the compound of formula 1 in a thiol-free state, decreases, and the fluorescence intensity at 430-550 nm, which is exhibited by the compound in a thiol-bound state, increases. The fluorescence intensity changes reversibly depending on the amount of thiols.

According to an embodiment of the present invention, the compound represented by formula 1 shows a maximum emission wavelength at 550-680 nm in a thiol-free state (i.e., a non-thiol-bound state), and shows a maximum emission wavelength at 430-550 nm in a thiol-bound state. According to another embodiment of the present invention, the compound represented by formula 1 shows a maximum emission wavelength at 550-650, 550-620, 550-600, 570-590 or 580 nm in a thiol-free state. According to still another embodiment of the present invention, the compound represented by formula 1 shows a maximum emission wavelength at 450-550, 470-550, 470-530, 490-530, 500-520 or 510 nm in a thiol-bound state.

According to an embodiment of the present invention, the fluorescence intensity of the compound of formula 1 at the emission wavelength changes continuously and reversibly as the amount of thiols in living cells increases. According to a more specific embodiment, the fluorescence intensity at the emission wavelength changes in the range of 430 nm to 680 nm.

According to an embodiment of the present invention, the compound represented by formula 1 shows a decrease in the fluorescence intensity at 550-680 nm and an increase in the fluorescence intensity at 430-550 nm, as the amount of thiols in living cells increases.

According to an embodiment of the present invention, the detection of thiols is performed by obtaining the ratio of the fluorescence intensity at 430-550 nm to the fluorescence intensity at 550-680 nm.

According to an embodiment of the present invention, the ratio is a relationship between the fluorescence intensity at 430-550 nm and the fluorescence intensity at 550-680 nm.

According to an embodiment of the present invention, the relationship is a mathematical ratio between the fluorescence intensity at 430-550 nm and the fluorescence intensity at 550-680 nm, and the mathematical ratio changes ratiometrically and reversibly depending on the amount of thiols in living cells to thereby indicate the amount of thiols in living cells in real time.

According to an embodiment of the present invention, the detection is the quantitative or qualitative detection of thiols in living cells.

According to an embodiment of the present invention, the detection is real-time quantitative detection.

According to an embodiment of the present invention, the detection of thiols in living cells indicates the oxidative stress or degree of oxidation of the cells.

According to an embodiment of the present invention, the detection of thiols in living cells indicates the degree of aging of the cells.

As used herein, the term "thiols" means organic sulfur compounds containing a sulfhydryl group bonded to carbon, and the term "sulfhydryl group" and the term "thiol group" are used interchangeably with each other.

According to an embodiment of the present invention, the thiols include glutathione (GSH), homocysteine (Hcy), cysteine (Cys) or any thiols present in the cysteine residues of proteins, but are not limited thereto.

In accordance with another aspect of the present invention, there is provided a sensor for detecting thiols in living cells, comprising the composition of the present invention.

Because the sensor for detecting the thiol according to the present invention comprises the composition for detecting the thiol according to the present invention, the detailed description of the components that are common between the two is omitted in order to avoid overlapping description.

In accordance with still another aspect of the present invention, there is provided a kit for diagnosing an oxidative stress-induced disease. As used herein, the term "oxidative stress-induced disease" means a disease caused by oxidative stress, and is used as the term "relative oxygen species (ROS)-related disease".

According to an embodiment of the present invention, the oxidative stress-induced disease is aging, degenerative arthritis, cataract, Alzheinmer's disease, cancer, fibrosis disease, diabetes, obesity, ischemia, ischemic reperfusion injury, inflammation, systemic lupus erythematosus, myocardial infarction, thrombotic stroke, hemorrhagic stroke, bleeding, spinal cord injury, Down syndrome, Crohn's disease, rheumatoid arthritis, uveitis, emphysema, gastric ulcer, oxygen toxicity, tumor, or radiation syndrome.

Because the kit for detecting the disease according to the present invention comprises the composition for detecting the thiol according to the present invention, the detailed description of the components that are common between the two is omitted in order to avoid overlapping description.

In accordance with still another aspect of the present invention, there is provided a method for screening a thiol enhancer or inhibitor in living cells, comprising the steps of: (a) adding the composition of the present invention to the living cells; (b) adding a test substance to the living cells of step (a); and (c) obtaining the ratio of the fluorescence intensity at 430-550 nm to the fluorescence intensity at 550-680 nm and comparing the obtained ratio with standard data, thereby determining that the test substance is the thiol enhancer or inhibitor.

In the method for screening the thiol enhancer or inhibitor, the test substance is added to the living cells, and the ratio of the fluorescence intensity at 430-550 nm to the fluorescence intensity at 550-680 nm in the living cells increases is compared with the standard data. When the ratio increases compared to the standard data, the test substance is determined to be the thiol enhancer, and when the ratio decreases compared to the standard data, the test substance is determined to be the thiol inhibitor.

Because the screening method of the present invention uses the composition for detecting thiols according to the present invention, the detailed description of the components that are common between the two is omitted in order to avoid overlapping description.

In accordance with still another aspect of the present invention, there is provided a composition for measuring antioxidant activity in living cells, comprising the composition of the present invention.

In accordance with still another aspect of the present invention, there is provided a method for measuring antioxidant activity in living cells, comprising the steps of:

(a) measuring in real time the ratio of the fluorescence intensity of the living cells at 430-550 nm to the fluorescence intensity at 550-680 nm; (b) adding the composition of the present invention to the living cells; (c) adding an oxidizing agent to the living cells of step (b); and (d) observing a change in the ratio of the fluorescence intensity.

According to an embodiment of the present invention, the method for measuring antioxidant activity according to the present invention further comprises, after step (d), the steps of: (i) measuring the time for the fluorescence intensity ratio to return to either the fluorescence intensity ratio of the living cells to which the oxidizing agent was not added or the fluorescence intensity ratio shown before the oxidizing agent is added; (ii) measuring the integrated value of the difference between the fluorescence intensity ratio of the living cells to which the oxidizing was not added and the fluorescence intensity ratio of the living cells to which the oxidizing agent was added, from a time point at which the oxidizing agent was added to a time point at which the fluorescence intensity ratio returns to the fluorescence intensity ratio shown before the oxidizing agent is added; (iii) determining the minimum concentration of the oxidizing agent, at which the fluorescence intensity ratio of the living cells to which the oxidizing agent was added starts to decrease; or (iv) determining the minimum concentration of the oxidizing agent, at which the fluorescence intensity ratio of the living cells to which the oxidizing agent was added does not return to either the fluorescence intensity ratio of the living cells to which the oxidizing agent was not added or the fluorescence intensity ratio shown before the oxidizing agent is added, wherein it is determined that the shorter the time in step (i) or the smaller the integrated value in step (ii) or the higher the minimum concentration in step (iii) or the higher the minimum concentration in step (iv), the higher is the antioxidant activity.

As demonstrated in the following examples, the fluorescence intensity ratio of the FreSH-tracer according to the present invention changes reversibly depending on the amount of thiols in living cells, and as described above, the detection of thiols according to the present invention indicates the degree of oxidation of living cells. Thus, the ratio of the fluorescence intensities, which is returned after treatment with the oxidizing agent, makes it possible to measure the antioxidant activity of living cells. Accordingly, it can be determined that (i) the shorter the time for the fluorescence intensity ratio to return to either the fluorescence intensity ratio shown before addition of the oxidizing agent or the fluorescence intensity ratio of living cells to which the oxidizing agent was not added, or (ii) the smaller the integrated value of the difference between the fluorescence intensity ratio of the living cells to which the oxidizing was not added and the fluorescence intensity ratio of the living cells to which the oxidizing agent was added, from a time point at which the oxidizing agent was added to a time point at which the fluorescence intensity ratio returns to the fluorescence intensity ratio shown before the oxidizing agent is added (that is, the smaller the area value between the graph for the fluorescence intensity ratio of the living cells to which the oxidizing agent was not added and the graph for the fluorescence intensity ratio of the living cells to which the oxidizing agent was added), or (iii) the higher the minimum concentration of the oxidizing agent, at which the fluorescence intensity ratio of the living cells to which the oxidizing agent was added starts to decrease), or (iv) the higher the minimum concentration of the oxidizing agent, at which the fluorescence intensity ratio of the living cells to which the oxidizing agent was added does not return to either the fluorescence intensity ratio of the living cells to which the oxidizing agent was not added or the fluorescence intensity ratio shown before the oxidizing agent is added, the higher is the antioxidant activity of the living cells.

Because the composition and method for measuring antioxidant activity according to the present invention use the composition for detecting thiols according to the present invention, the detailed description of the components that are common between the two is omitted in order to avoid overlapping description.

Advantageous Effects

The features and advantages of the present invention are summarized as follows.

(a) The present invention provides a composition, senor and diagnostic kit for detecting thiols in living cells, which comprise a FreSH-tracer (Fluorescent Real-time SH group-tracer), and a method of screening a thiol enhancer or inhibitor by use of the same.

(b) The present invention provides a composition for measuring antioxidant activity in a living cell, which comprises the FreSH-tracer, and a method for measuring antioxidant activity using the same.

(c) According to the present invention, it has been found that the fluorescence intensity of the FreSH-tracer according to the present invention changes continuously, ratiometrically and reversibly depending on the amount of thiols in living cells, and thus the FreSH-tracer can be effectively used as a highly sensitive biosensor for quantitatively or qualitatively detecting the levels of thiols in living cells.

DESCRIPTION OF DRAWINGS

FIG. 1a shows the reversible reaction of the FreSH-tracer.

FIGS. 1b to 1f show the results obtained by equilibrating the FreSH-tracer with various concentrations of glutathione ([GSH]0=0-200 mM) for 20 minutes and then measuring the reaction therebetween.

FIG. 1b shows the results of measuring the reversible reaction of the FreSH-tracer by the UV-Vis absorption spectrum.

FIGS. 1c to 1f show a graph (FIG. 1e) obtained by monitoring the fluorescence emission spectra of the FreSH-tracer, generated by excitation at 430 nm (FIG. 1c) and 520 nm (FIG. 1d) and monitored at 510 nm (F510) and 580 nm (F580), respectively.

FIG. 1f shows the F510/F580 ratio as a function of increasing concentrations of glutathione.

FIGS. 1g to 1h show the real-time change in the fluorescence of the FreSH-tracer when the thiol group of glutathione by introducing 5 mM NEM (N-ethyl maleimide) at 800 seconds after reaction with 5 mM glutathione. FIG. 1g shows the results of monitoring the fluorescence intensities of F510 and F580, and FIG. 1h shows the F510/F580 ratio.

FIG. 1i shows the real-time change in the fluorescence of the FreSH-tracer that reacted with the indicated concentration of $H_2O_2$ at 400 seconds after the start of a ratiometric sensor reaction after equilibrating the FreSH-tracer on with 5 mM glutathione for 15 minutes.

FIG. 1j shows the change in the F510/F580 ratio of the FreSH-tracer that reacted with 5 mM GSSG or $H_2O$ for seconds and then treated with 5 U/ml of glutathione reductase (GR) and 0.5 mM NADPH for 300 seconds.

FIG. 2a indicates that PSH reacts slowly and quantitatively with the FreSH-tracer after a cell protein (PSH) prepared from a HeLa cell lysate and a cell protein (PS-NEM) alkylated with NEM were mixed at various ratios.

FIG. 2b indicates that GSH reacts rapidly and quantitatively with the FreSH-tracer in 15 mg/ml of a thiol group-free protein (PS-NEM) environment.

FIGS. 2c to 2e show the results of observing in real time the F510/F580 ratio of the FreSH-tracer to confirm that PSH and GSH are oxidized by treatment with the oxidizing agent diamide in the presence of 15 mg/ml of protein.

FIG. 3a shows a confocal microscope fluorescence mage of cells, obtained by loading the cells with the FreSH-tracer, treating the cell culture with 0.5 mM diamide at 45 seconds after loading, and injecting 0.5 mM DTT into the cell culture at 125 seconds after diamine treatment. (F510=Ex403-Em525/25; F580=Ex488-Em595/25; scale bar=10 μm).

FIGS. 3b and 3c show the results obtained by measuring the fluorescence intensity (arrowhead in FIG. 3a) of each of two cells (FIG. 3b) and calculating the fluorescence intensity ratio (FIG. 3c).

FIG. 3d graphically shows the F510/F580 ratio of the whole cell region, cytoplasm and nucleoplasm obtained from four different cells.

FIG. 3e shows the results obtained by treating FreSH-tracer-loaded cells with 50 μM $H_2O_2$ at 5 minutes after the start of measurement and measuring the F510/F580 ratio of the cells at the indicated time points. The corresponding emission intensities are shown in FIG. 21a (scale bar=10 μm).

FIG. 3f shows the results obtained by calculating the F510/F580 ratio of the whole cell region, cytoplasm and nucleoplasm obtained from 7 different cells.

FIG. 3g shows the results obtained by treating cells with the indicated concentrations of $H_2O_2$ at 5 minutes after the start of measurement and measuring the radiometric sensor reaction in the whole cell region. The blue line (50 μM $H_2O_2$) indicates the F580/F510 ratio of cells indicated as the arrowhead in FIG. 3e.

FIG. 3h graphically shows the maximum ratio change that decreases from the average fluorescence intensity ratio of the whole cell area for the initial 5 minutes by treatment with various concentrations of $H_2O_2$, based on an experiment similar to that shown in FIG. 3g.

FIG. 4a shows the results obtained by seeding HeLa cells at different densities (low density: $1\times10^4$, medium density: $2\times10^4$, high density: $4\times10^4$ cells/cm), culturing the seeded cells for 24 hours, treating the cells with 5 μM FreSH-tracer, equilibrating the tracer for 2 hours, analyzing the fluorescence of the cells with a confocal microscope, and then imaging the fluorescence intensity ratio. The corresponding emission intensities are shown in FIG. 21b.

FIG. 4b shows the results obtained by culturing HeLa cells in 0% FBS or 10% FBS-containing medium for 18 hours and analyzing the cells by the method shown in FIG. 4a. The corresponding emission intensities are shown in FIG. 21c.

FIG. 5a shows images of the F510/F580 ratio of a cell group treated with the solvent ethanol or PMA (phorbol 12-myristate 13-acetate) at the indicated time points (scale bar=10 μm). The corresponding emission intensities are shown in FIG. 21d.

FIG. 5b is a graph showing the results of measuring the F510/F580 ratio of each of one control cell (arrowhead in FIG. 5a) and two PMA-treated cells (arrow in FIG. 5b) as a function of time.

BEST MODE

Figure 1A:
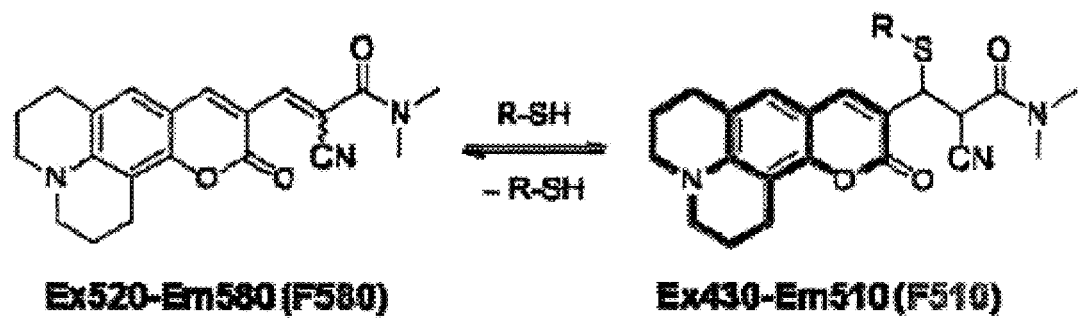
FIGS. 1a-1j show experimental results that indicate that a FreSH-tracer reacts reversibly and rapidly with reduced glutathione (a.u.: arbitrary unit; Ex: maximum excitation wavelength; Em: maximum emission wavelength).

Hereinafter, the present invention will be described in further detail with reference to examples. However, it will be obvious to those skilled in the art that these examples are for illustrative purposes and are not intended to limit the scope of the present invention.

EXAMPLES

Experimental Materials and Methods

1. Reagents

Glutathione reductase was purchased from EMD Millipore, and $H_2O_2$, N-ethylmaleimide (NEM), dithiothreito (DTT), diamide, Ellman's reagent, bis-chloroethylnitrosourea (BCNU), buthionine sulphoximine (BSO) and phorbol 12-myristate 13-acetate (PMA) were purchased from Sigma-Aldrich.

2. In Vitro Reaction of FreSH-tracer (Fluorescent Real-Time SH Group-Tracer with Thiol Compound A buffer (10 mM phosphate, 150 mM NaCl, pH 7.4, $H_2O$:DMSO=98:2) containing a mixture of a thiol compound (0-200 mM) and a FreSH-tracer (10 μM) was prepared, and the time-dependent UV-Vis absorption spectrum and fluorescence emission spectrum of the buffer were measured with S-3100 spectrophotometer and Hitachi F-7000 spectrophotometer. For preparation of buffers for use in in vitro experiments at pHs of pH 4, 5, 9 and 10, acetate and CHES (2-(cyclohexylamino)ethanesulfonate) were used instead of phosphate.

3. Calculation of Kd Value of Thiol Compound

After a chemical equilibrium between the thiol compound (0-200 mM) and the FreSH-tracer was formed by an in vitro reaction, the emission spectrum of fluorescence emitted upon excitation with light at a wavelength of 430 nm was measured. The relationship between the fluorescence intensity at the maximum emission wavelength (580 nm) and the concentration of the thiol compound was analyzed by non-linear regression to determine the chemical equilibrium constant (Kd) between the thiol compound and the FreSH-tracer.

4. Preparation of HeLa Cell Protein

HeLa cells were seeded in a 150 mm dish, and the cells reached a confluence of 80% after 2 days. The cells were collected by scraping in PBS, followed by centrifugation. To isolate a protein from the cells, the cells were resuspended in PBS containing 0.1% Triton X-100, and were completely lysed by sonication. After centrifugation at 12000 g and 4° C. for 10 minutes, the lysate was dialyzed in PBS at 4° C. to remove low-molecular-weight thiol species including glutathione. The amount of protein was quantified by the BCA method. In the method, a thiol-containing protein (PSH) sample was used. To remove a thiol group from the protein sample, the protein sample was reacted with 100 mM NEM solution at room temperature for 2 hours, and to remove NEM having residual activity from the sample, the sample was dialyzed in PBS at 4° C., and then dialyzed in 5 mM DTT-containing PBS at 4° C. for 1 hour. The remaining DTT was removed by dialysis in PBS at 4° C., and the protein was used as an NEM-alkylated protein (PS-NEM) sample.

5. Measurement of Levels of Thiol and GSH in Lysate of HeLa Cells Treated with $H_2O_2$ $2.5 \times 10^6$ HeLa cells were seeded in a 150 mm dish, and cultured for 18 hours under the conditions of 37 t and 5% $CO_2$. The cells were treated with 5 or 10 mM of $H_2O_2$ for the indicated time and washed twice with cold PBS. The cell pellets were collected by centrifugation at 12000 g and 4° C. for 1 min, and then immediately frozen in liquid nitrogen. The frozen cell pellets were resuspended in 1 mL of a lysis buffer (containing 50 mM MES, 50 mM phosphate and 1 mM EDTA, pH 6) and lysed by sonication, followed by centrifugation at 12000 g and 4° C. for 10 minutes. The supernatant was analyzed using the BCA protein quantification method to determine the total protein amount, and then analysis of the thiol and GSH levels was performed. To analyze the thiol level using the FreSH-tracer, 180 µL of the supernatant was mixed with 20 µL of 10 µM FreSH-tracer in a 96-well black plate and incubated at room temperature for 90 minutes. The fluorescence intensities of F510 (Ex430-Em510) and F580 (Ex520-Em580) were measured using Infinite M200Pro (TECAN) microplate reader. For Ellman's assay, 10 µL of the supernatant was mixed with 100 µg/µL of Ellman's reagent in 1 mM EDTA-containing PBS in a 96-well plate and incubated at room temperature for 15 minutes. The amount of the thiol was measured by the absorbance at 412 nm. The remaining supernatant was used in a GSH assay using a glutathione assay kit (Cayman). The amount of reduced GSH was calculated by subtracting two times the GSSG concentration from the total GSH concentration.

6. Imaging of Living Cells

HeLa and RAW264.7 cells were cultured in DMEM (containing 10% heat-inactivated FBS (Hyclone), 100 U/ml of penicillin, 100 µg/ml of streptomycin sulfate and 2 mM glutamine and free of phenol red). HeLa ($1.8 \times 10^5$ cells/dish) and RAW264.7 ($2 \times 10^5$ cells/dish) were seeded in 35 mm cover glass bottom dishes (SPL Life Sciences), and then cultured under the conditions of 37° C. and 5% $CO_2$ for the indicated time. Before observation using a fluorescence microscope, the HeLa cells were incubated with 2 mL of a medium containing 5 µM of the FreSH-tracer HeLa for 2 hours, and the RAW264.7 cells were incubated for 4 hours. Real-time images of the cells were acquired using a Nikon A1 laser scanning confocal microscope. The imaging test was 2 performed while the cells were incubated under the conditions of 37° C. and 5% $CO_2$ in a chamber mounted in a Nikon ECLIPSE Ti inverted microscope equipped with CFI Plan apochromat 60× and 1.40 numerical aperture (NA) objective lenses. The FreSH-tracer was excited with laser beams at 403 nm and 488 nm, and the fluorescence of the tracer was detected through filters with 500-550 nm and 570-620 nm band intervals. Using NIS-Elements AR software, the experimental data were analyzed and the ratio of fluorescence was imaged.

7. Flow Cytometry

HeLa cells were cultured in 100 mm dishes at different densities for about one day, and then treated with 5 µM FreSH-tracer for 1.5 hours. The cells were detached from the dishes by trypsin treatment to obtain single cells, and then centrifuged to remove trypsin. Afterwards, the HeLa cells were resuspended in a medium containing 5 µM FreSH-tracer and analyzed using LSRII Flow Cytometer System (BD Biosciences). Using FlowJo software, the ratio of fluorescence (530/30 nm) emitted after excitation at 405 nm and 488 nm was calculated.

8. Quantification of GSH in BSO-Treated HeLa Cells

HeLa cells were cultured in a transparent bottom white 96-well plate at the indicated density. After treatment with various concentrations of BSO for 48 hours, the cells were washed twice with HBSS, and then the total GSH and GSSG concentrations were measured using a GSH/GSSG-Glo assay kit (Promega). The amount of reduced GSH was calculated by subtracting the amount of GSSG from the total amount of GSH. The concentration of GSH in the HeLa cells was calculated based on the known average volume of HeLa cells (3000 µm$^3$) and the cell number of the whole sample, determined by counting the cell number of a portion of the sample.

Experimental Results

Figure 1B:
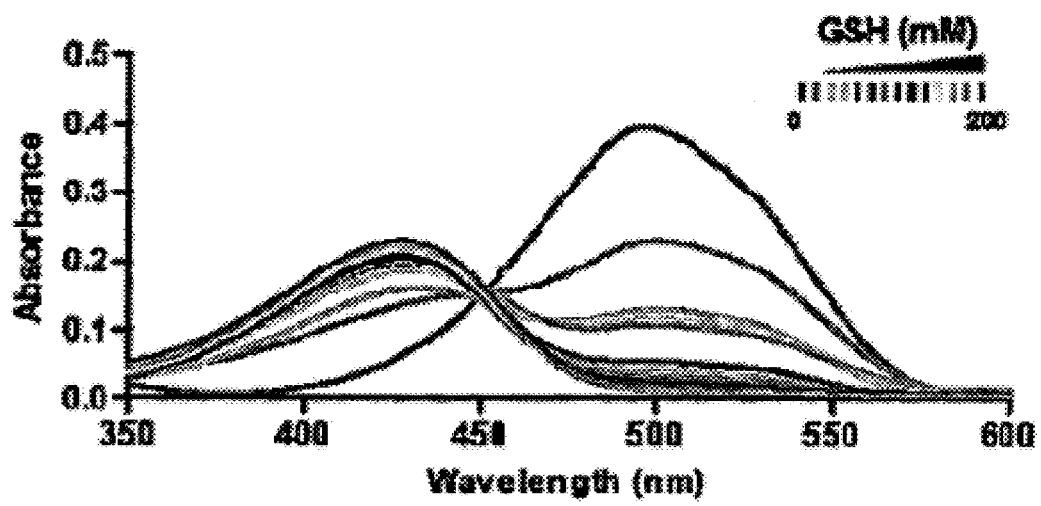
Figure 1C:
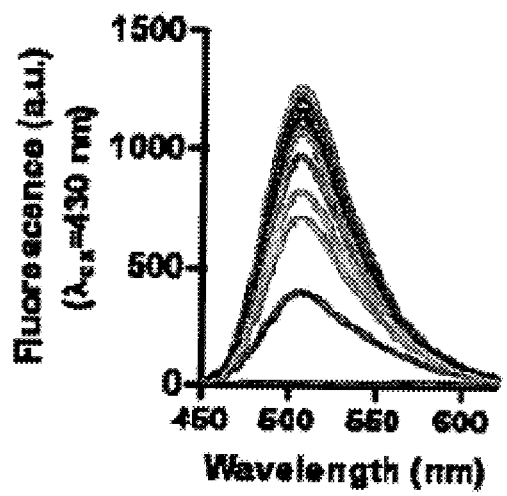
Figure 1D:
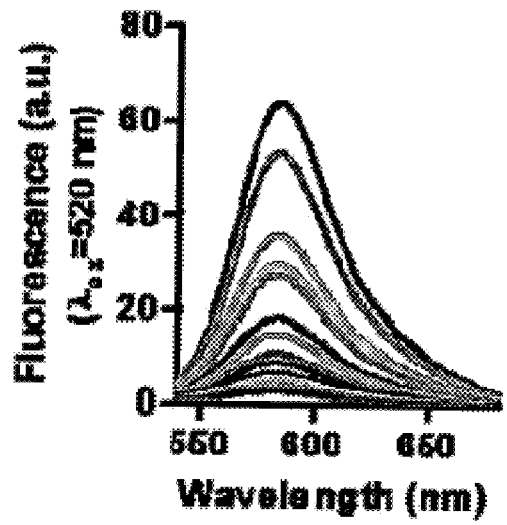
Figure 1E:
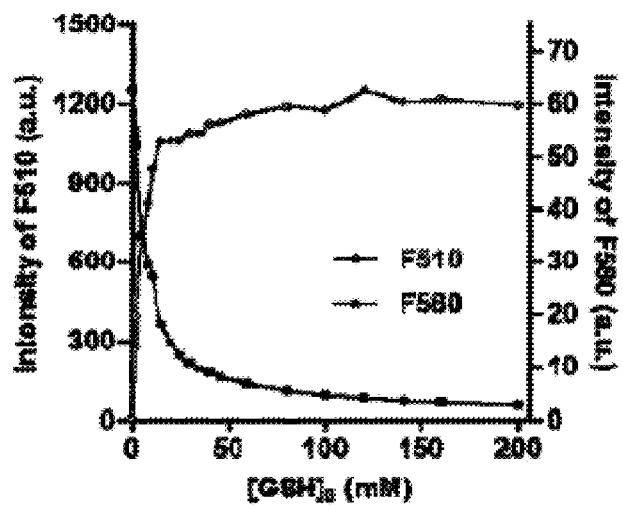
Figure 1F:
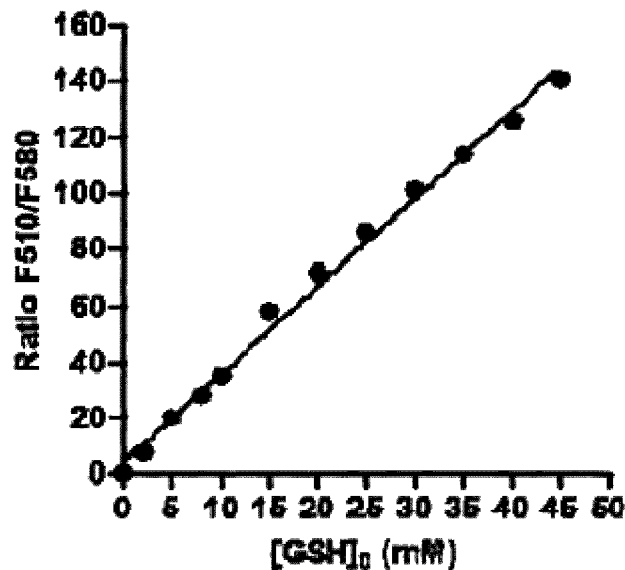
Figure 1G:
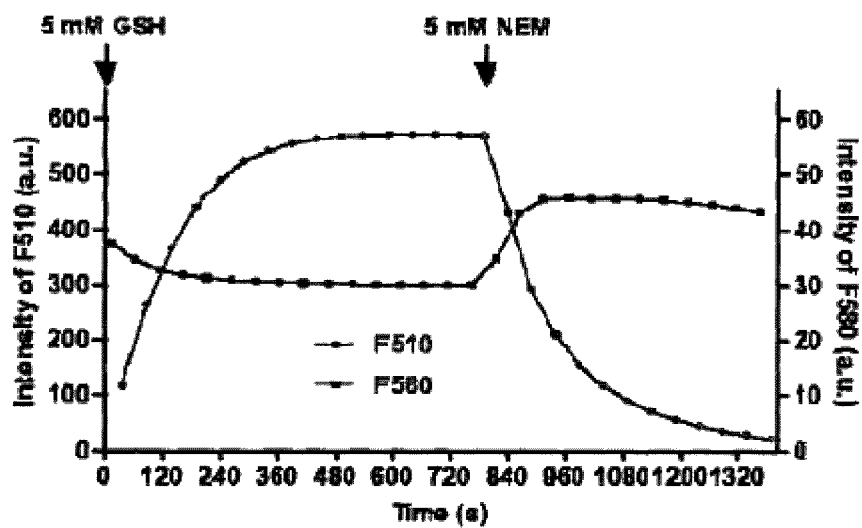
Figure 5A:
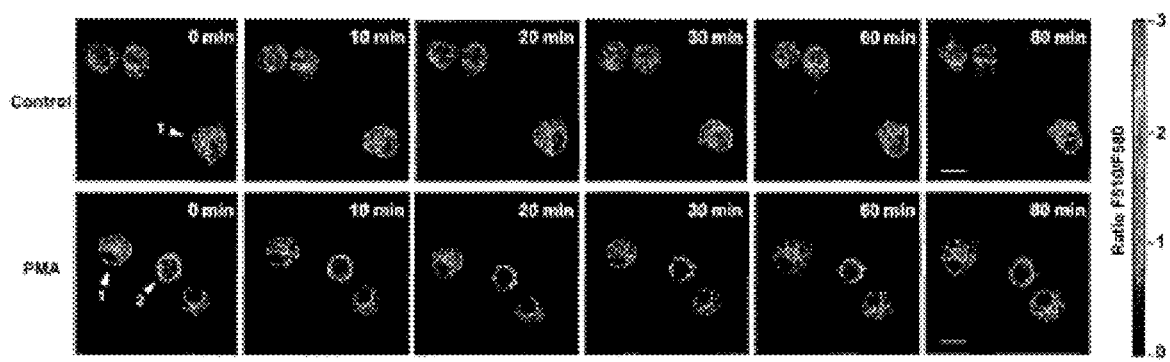
FIGS. 5a-5b show the results of observing in real time the level of thiols in living cells caused by activation of NADPH oxidase in RAW264.7 by use of the FreSH-tracer.
Figures 5B, 6:
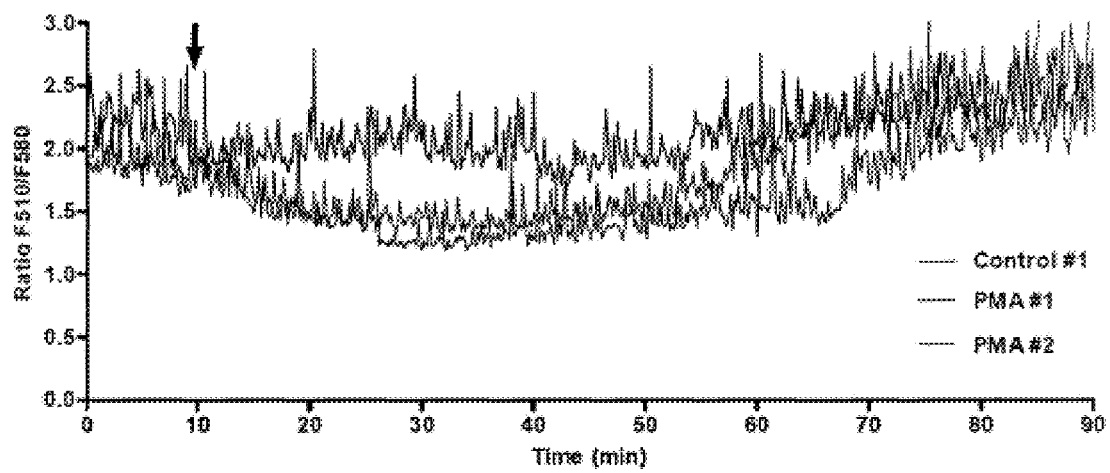
FIG. 6 shows the chemical equilibrium constant (Kd) values of sulfhydryl compounds for the FreSH-tracer.

1. Observation of the Property of FreSH-Tracer that Reacts Ratiometrically, Reversibly and Rapidly with GSH The FreSH-tracer has a Kd value in the mM range for compounds containing a sulfhydryl group (thiol group) (FIG. 6). This property of the FreSH-tracer is suitable to measure the amount of GSH that is the most abundant intracellular low-molecular-weight thiol and that is present at concentrations in units of mM. When GSH was added to the FreSH-tracer while the concentration of GSH increased, the absorbance of the tracer for UV light and visible light increased at $\lambda_{max}$=430 nm and decreased at $\lambda_{max}$=520 nm (FIG. 1b), and the fluorescence emission intensity of the tracer increased at about 510 nm (F510, $\lambda_{ex}$=430 nm; $\lambda_{em}$=510 nm) and decreased at about 580 nm (F 580, $\lambda_{ex}$=520 nm; $\lambda_{em}$=580 nm) (FIGS. 1c to 1e). The present inventors have newly found that the ratio of the intensity of F510 to the intensity of F580 (F510/F580) of the FreSH tracer changes in proportion to a wide range of the GSH concentration (FIG. 1e). This suggests that the tracer can be used as a radiometric sensor. The regression curve obtained from the fluorescence intensity ratio indicated linearity ($R^2$=0.9938) in a concentration range (0-50 mM) wider than the concentration of GSH present in the cells (FIG. 1f).

Furthermore, the present inventors measured the reactions of various derivatives falling within the scope of the FreSH-tracer, that is, the compounds represented by formulas 2 to 8, with β-mercaptoethanol or glutathione. The results of the measurement are shown in FIGS. 22 to 28.

As shown in FIGS. 22 to 28, in the case of various derivatives falling within the scope of the FreSH-tracer, the absorbance of the derivative for UV light and visible light increased at $\lambda_{max}$=430 nm and decreased at $\lambda_{max}$=520 nm, and the fluorescence emission intensity increased at about 510 nm (F510, $\lambda_{ex}$=430 nm; $\lambda_{em}$=510 nm) and decreased at about 580 nm (F580, $\lambda_{ex}$=520 nm; $\lambda_{em}$=580 nm). In addition, it was found that the ratio of the intensity of F510 to the intensity of F580 (F510/F580) changes in proportion to a wide range of the GSH concentration.

Thus, the present inventors have demonstrated that all various derivatives that may fall within the scope of the FreSH tracer may also be used as the sensor of the present invention.

Figure 7:
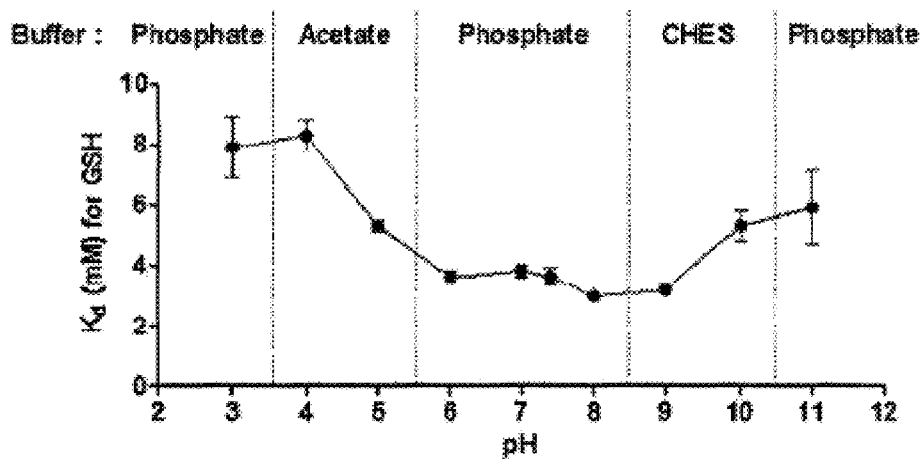
FIG. 7 shows the effect of pH on the Kd values of the FreSH-tracer and GSH.

The chemical equilibrium constant Kd between the FreSH-tracer and GSH did not greatly change at a pH between 6 and 9 (FIG. 7), suggesting that a general change in pH in cells does not greatly influence the reactivity of the FreSH-tracer with thiols.

The above data suggest that the FreSH-tracer has the most suitable sensor property for monitoring the intracellular GSH level.

Figure 1H:
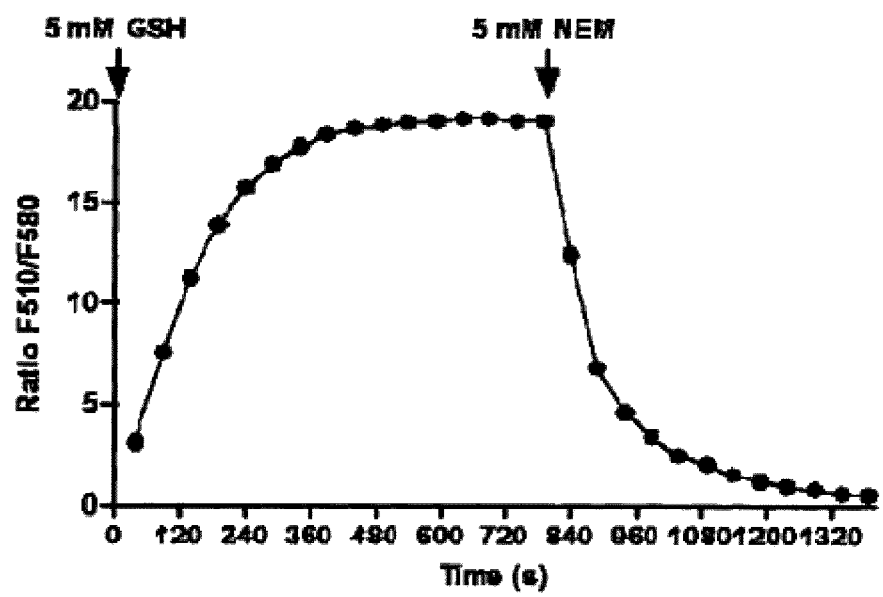
Figure 1I:
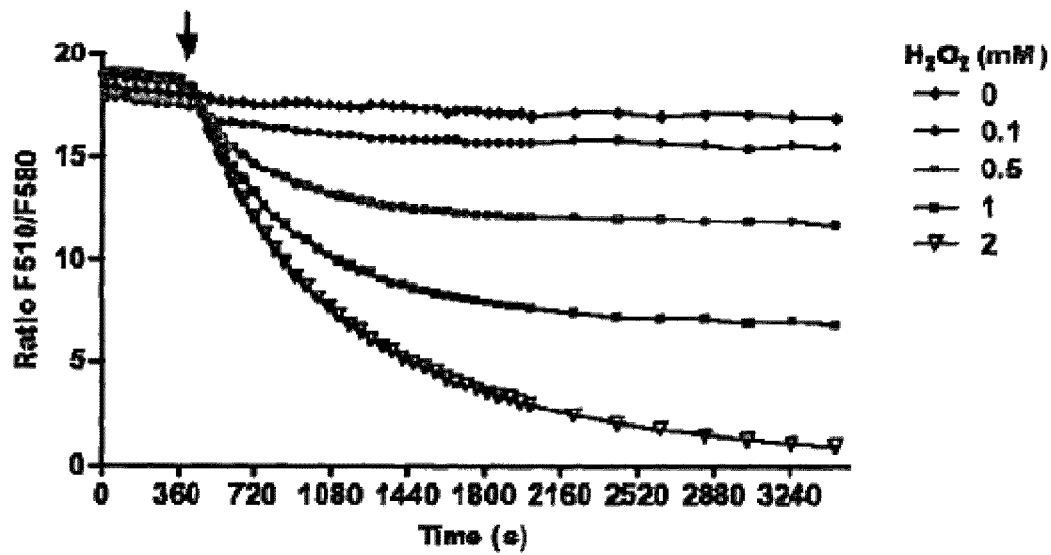
Figure 1J:
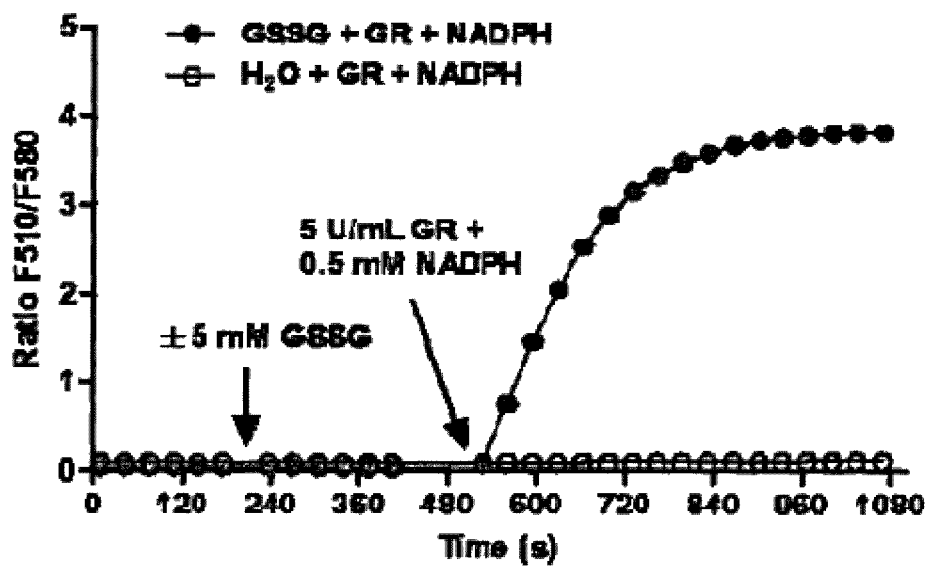
Figure 4A:
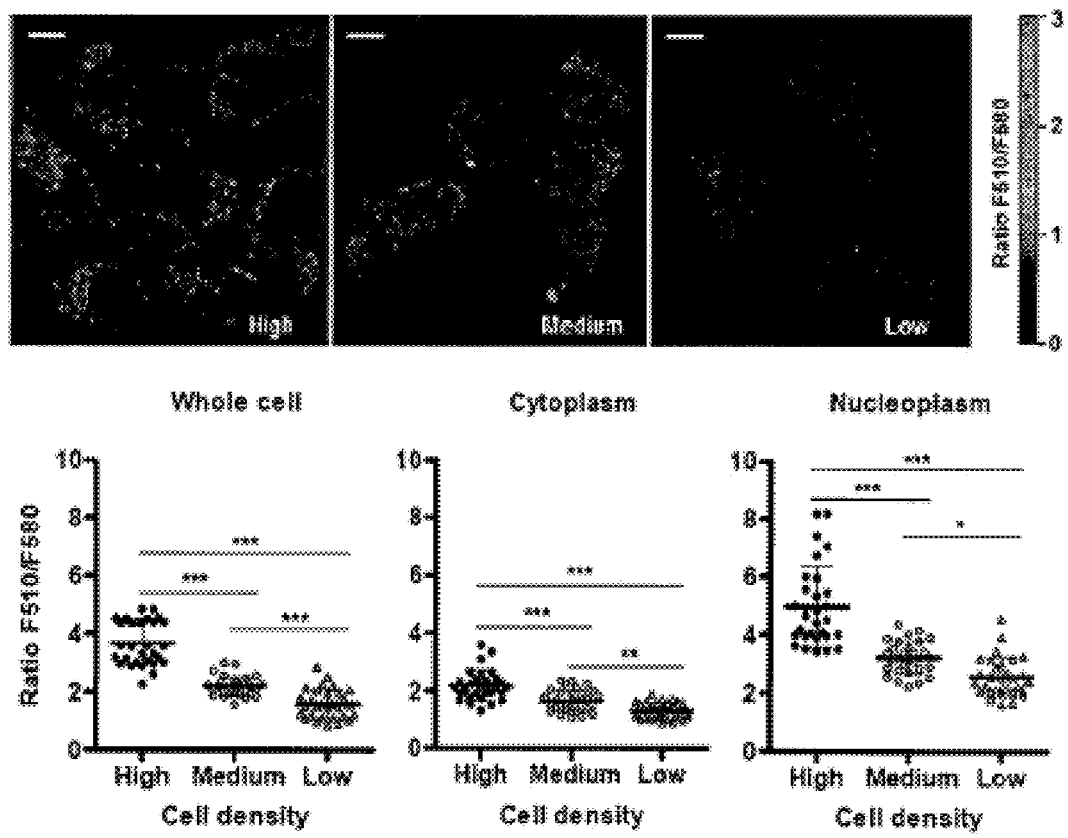
FIGS. 4a-4b indicate that the level of reduced thiols in cells is influenced by cell density and serum starvation. The experimental data are representative values for three repeated experiments (F510=Ex403-Em525/25; F580=Ex488-Em595/25; scale bar=10 μm; *P<0.05, P<0.01, *P<0.001).
Figure 8:
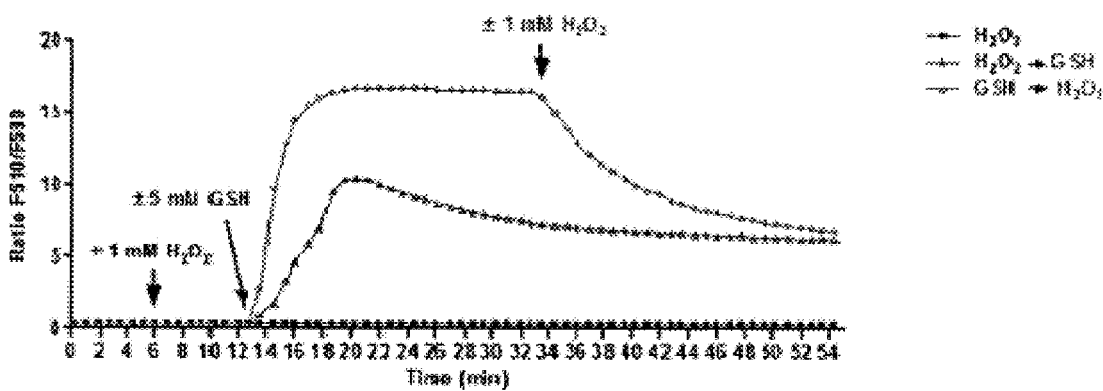
FIG. 8 shows in vitro experiment results that indicate that $H_2O_2$ (5 mM) reacts directly with the FreSH-tracer so as not to induce a change in the fluorescence intensity ratio.
Figure 9:
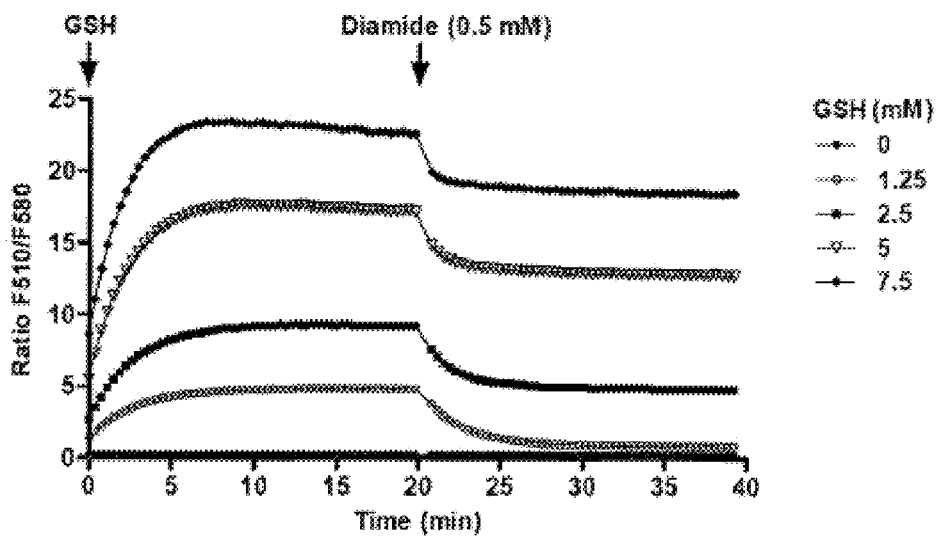
FIG. 9 indicates that the fluorescence intensity ratios of the FreS H-tracer in the presence of various amounts of glutathione are reduced to the same levels by treatment with 0.5 mM diamide.

Afterwards, the present inventors have examined the reaction rate of the FreSH-tracer. When 5 mM GSH was added to the FreSH-tracer, the intensities of F510 and F580 changed rapidly in opposite patterns for about 240 seconds, and when 5 mM of N-ethylmaleimide (NEM) that is a thiol-alkylating reagent was added to the FreSH-tracer at about 800 seconds, each of the fluorescence intensities returned to the initial value within 500 seconds. The fluorescence intensity ratio of the corresponding sensor was increased to about 20 by adding 5 mM GSH, and then returned to the initial level by adding the same amount of NEM (FIG. 1h). Afterwards, the present inventors have verified that the FreSH-tracer does not react with an oxidized form of GSH. First, the present inventors used the thiol-specific oxidizing agent diamine for oxidized GSH. Addition of 0.5 mM diamide reduced the sensor fluorescence intensity ratios, obtained from various amounts of GSH, to a constant level of about 4. Second, the sensor fluorescence intensity ratio obtained from 5 mM GSH decreased in a manner dependent on the amount of $H_2O_2$ added (FIG. 1i). The present inventors have found that, at the concentrations used in the experiment, $H_2O_2$ (FIG. 4a) and diamide (data not shown) did not directly influence the fluorescence intensity ratio (FIGS. 8a and 8b). Third, addition of GSSG did not influence the fluorescence intensity ratio of the sensor (FIG. 1j). When glutathione reductase and NADPH, which are essential for reducing GSSG to GSH, were added to the mixture, the fluorescence intensity ratio of the sensor increased rapidly.

Thus, the above results demonstrate that the FreSH-tracer can be used to monitor in real time a change in the amount of reduced GSH in vitro.

2. Dynamic Properties of FreSH-Tracer that Reacts with Cellular PSH (Cysteine Residues of Proteins)

Figure 2A:
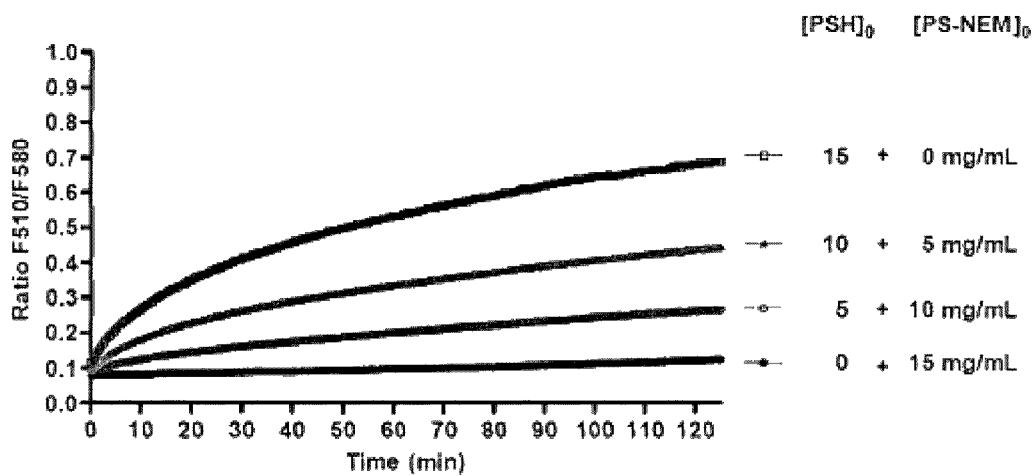
FIGS. 2a-2e indicate that a protein thiol (PSH) reacts quantitatively with the FreSH-tracer and the reaction rate thereof is slower than that of GSH.
Figure 2B:
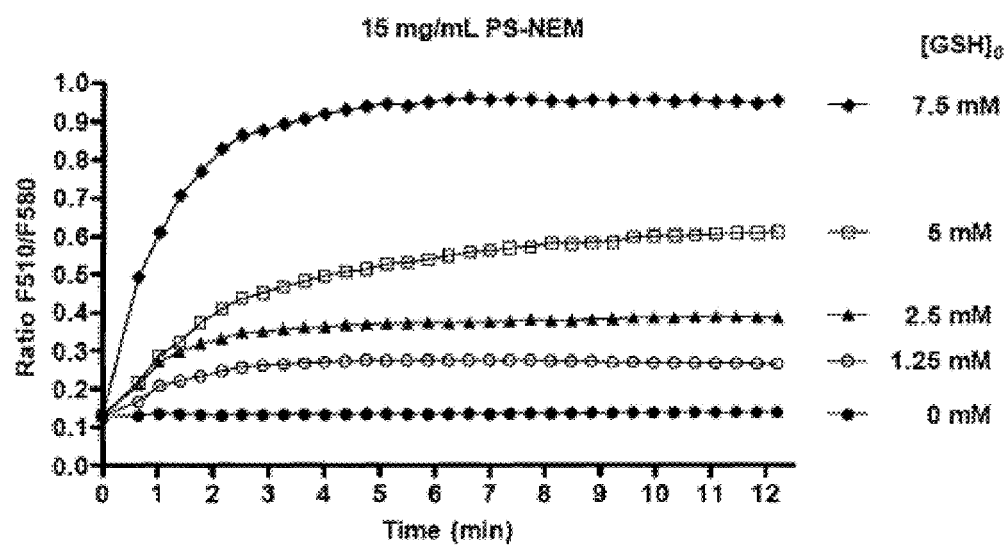
Figure 2C:
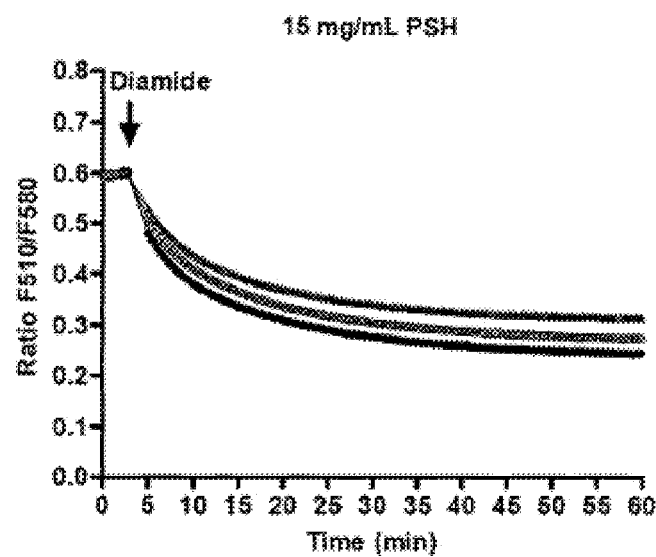
Figure 2D:
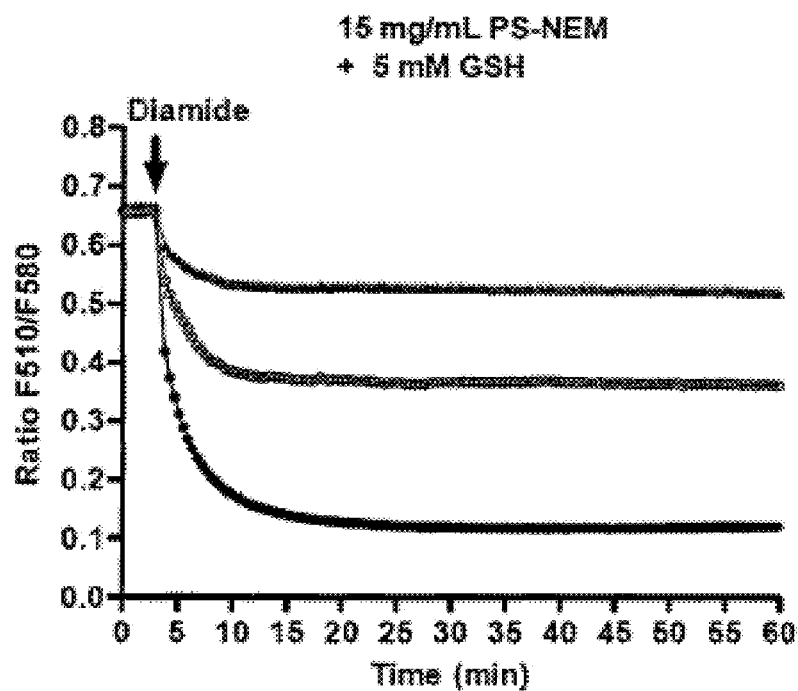
Figure 2E:
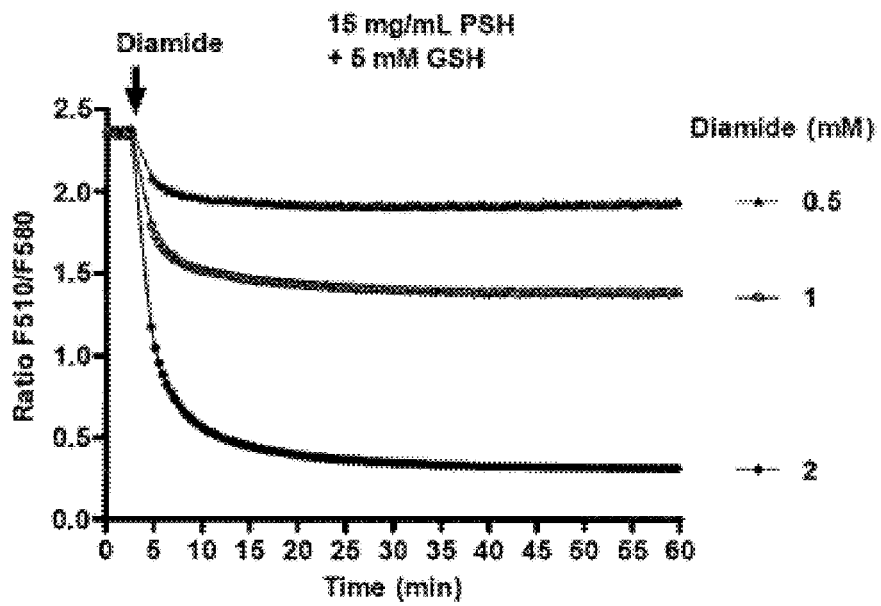
Figure 10A:
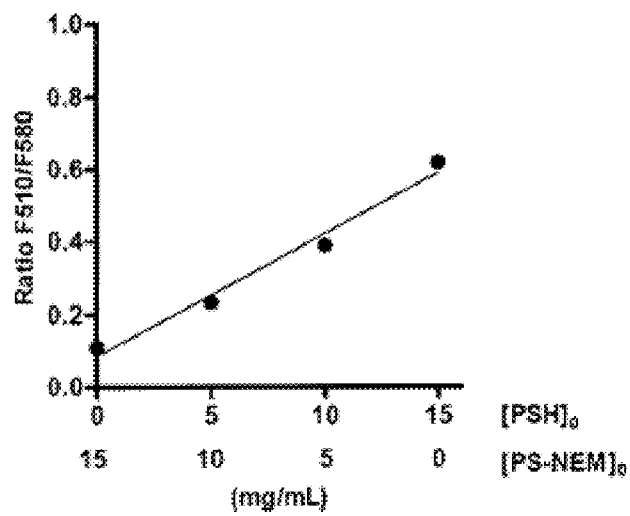
FIGS. 10a and 10b indicate that glutathione (GSH) and PSH in the presence of a high concentration of a cell protein are quantitatively detected by use of a FreSH-tracer sensor reaction.
Figure 10B:
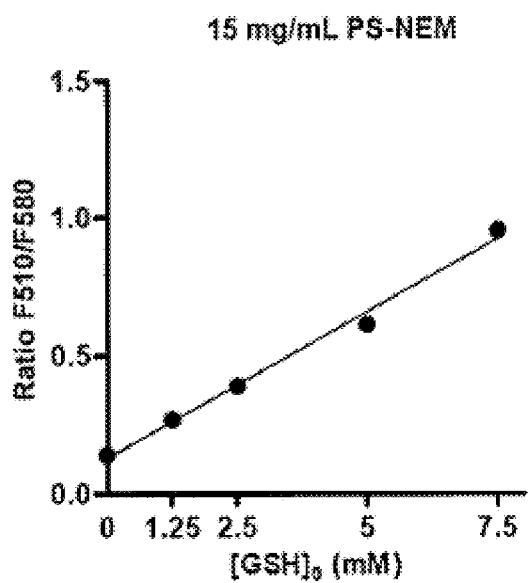
Figure 11A:
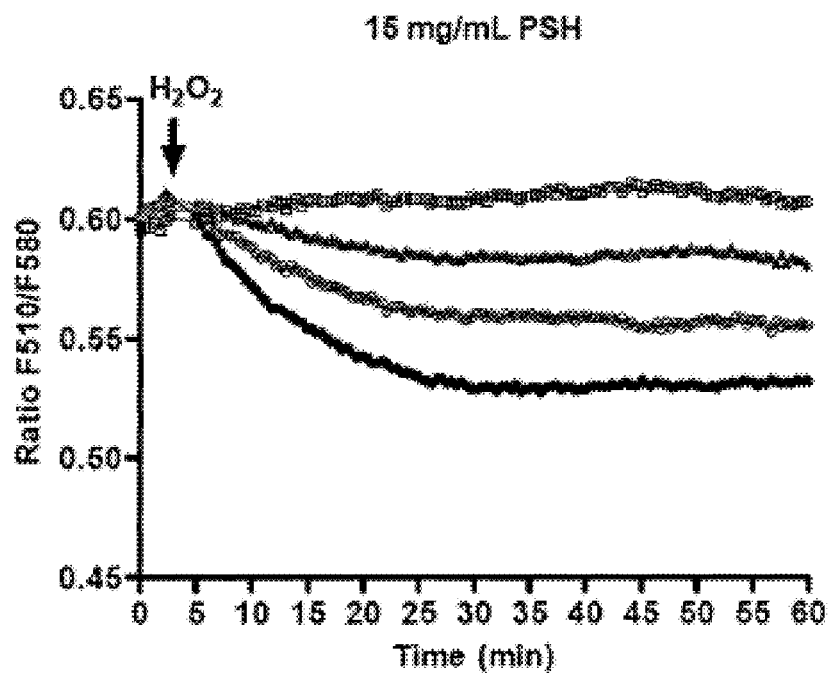
FIGS. 11a to 11c compare the reaction rates of FreSH-tracers derived from PSH, GSH or PSH plus GSH in oxidation reactions with $H_2O_2$.
Figure 11B:
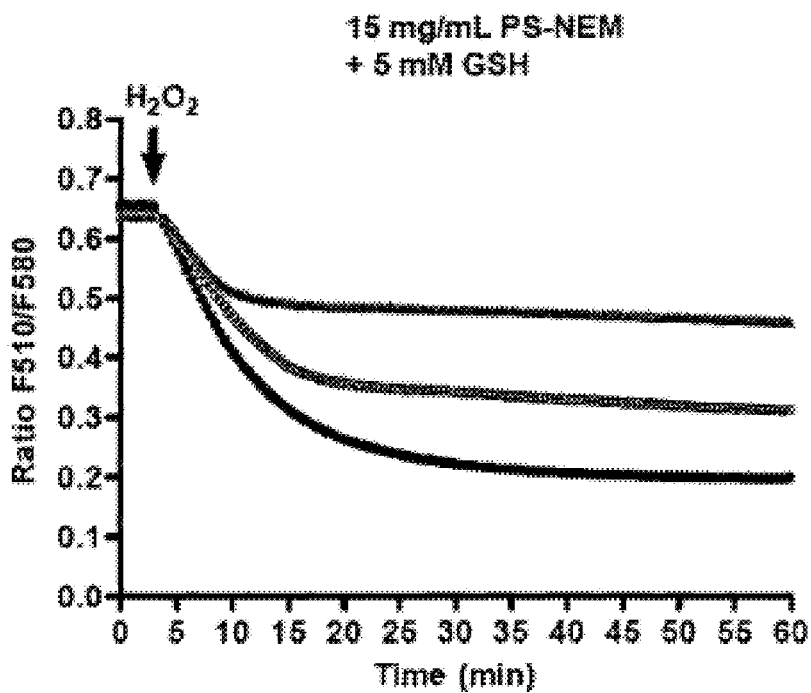
Figure 11C:
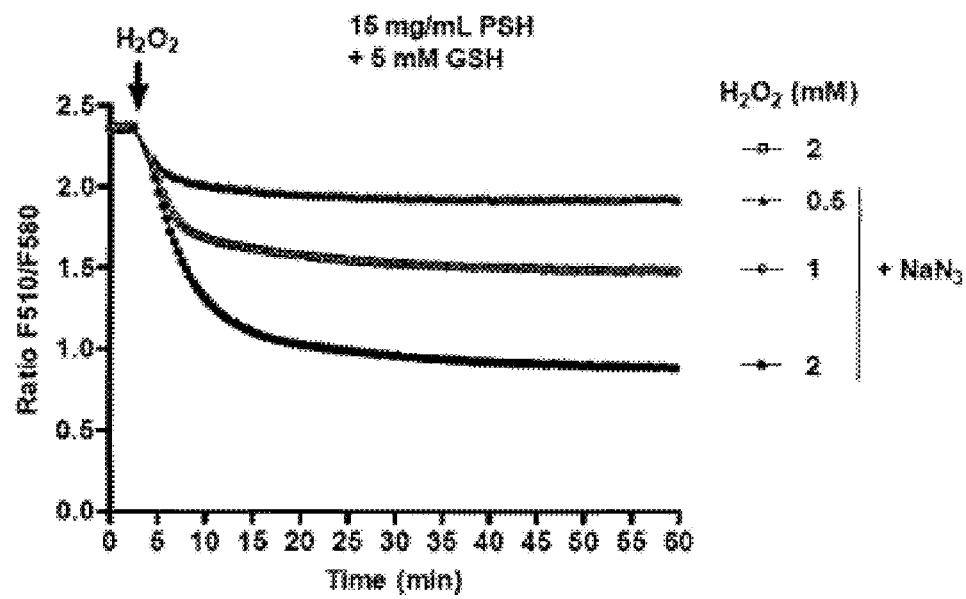
Figure 12A:
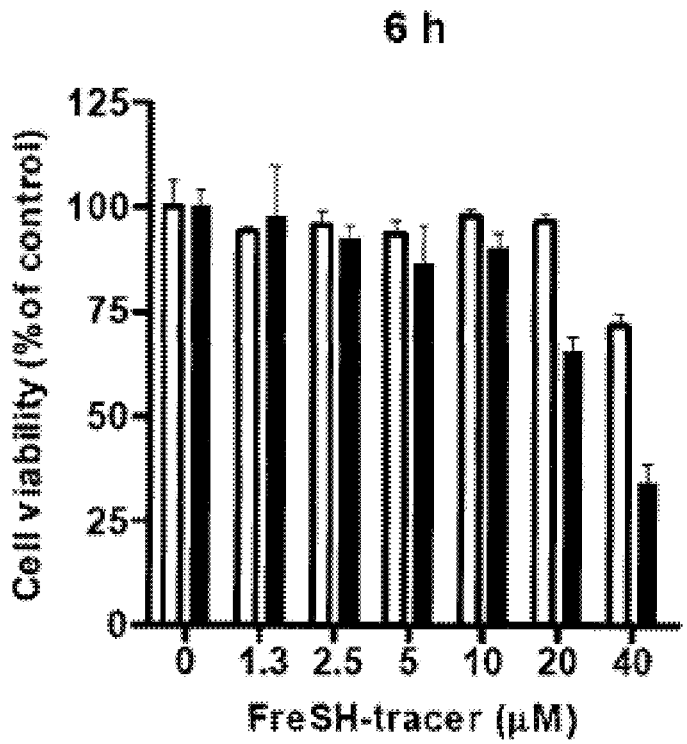
FIGS. 12a and 12b shows the results of observing the survival of HeLa cells at 6 hours and 12 hours after treatment with the FreSH-tracer. It can be seen that there is no cytotoxicity at the FreSH-tracer concentration (~5 μM) used in the cell experiment.
Figure 12B:
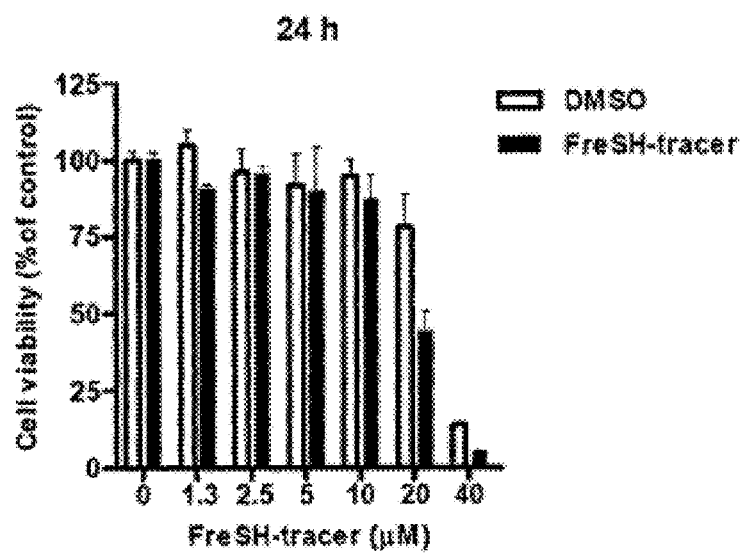

Because intracellular thiol groups are abundantly found in PSH together with GSH, the present inventors studied the mechanism by which the FreSH-tracer reacts with PSH. In order to examine the direct effect of PSH on a change in the fluorescence intensity ratio of the sensor, the present inventors prepared cellular PSH from a lysate of HeLa cells from which low-molecular-weight thiols including GSH were removed by dialysis, and added NEM-alkylated protein (PS-NEM) to control the total protein amount to 15 mg/ml corresponding to about 1/10 of the evaluated intracellular protein concentration. The fluorescence intensity ratio of the sensor increased slowly in a manner dependent on the amount of PSH added (FIGS. 2a and 10a). Meanwhile, GSH rapidly increased the fluorescence intensity ratio of the sensor even in the presence of 15 mg/ml PS-NEM (FIGS. 2b and 10b). Afterwards, the present inventors compared the reactions of GSH and PSH with the FreSH-tracer, based on changes in the sensor fluorescence intensity ratios obtained from three combinations of two types of thiols during the oxidation procedures caused by diamide (FIGS. 2c to 2e) and $H_2O_2$ (FIGS. 11a to 11c). In the present invention, a mixture of cellular proteins was pretreated with 0.1 mM sodium azide in order to remove catalyse activity from the mixture, and then an experiment using $H_2O_2$ was performed. The sensor fluorescence intensity ratio obtained from PSH was decreased slowly by treatment with the two oxidizing agent (FIGS. 2c and 11a), whereas the sensor fluorescence intensity ratio obtained from GSH decreased more rapidly (FIGS. 2d and 11b). The fluorescence intensity ratio of the sensor mixed with PSH and GSH was reduced by treatment with the oxidizing agent in a dynamic pattern similar to the fluorescence intensity ratio obtained from the sample mixed with GSH and PS-NEM (FIGS. 2e and 11c). In addition, the present inventors examined the effects of cellular PSH and GSH on the thiol sensor in cells, fixed with formaldehyde, by use of a microscope. When the fixed cells are treated with a detergent to increase the permeability of the cell membrane, low-molecular-weight thiols, including GSH, are removed. For this reason, an experiment was performed on the assumption that the fixed cells without detergent treatment contained GSH and PSH but the detergent-treated cells contained only PSH. When the present inventors observed the basal sensor fluorescence intensity ratio by confocal microscope analysis, it was shown that the sensor fluorescence intensity ratio was reduced to about ¼ by detergent treatment. This suggests that GSH is a major thiol that reacts with the sensor in cells. The present inventors observed the reaction of the sensor in the fixed cells by treatment with the oxidizing agent. The fluorescence intensity ratio of the sensor was reduced rapidly in the non-damaged cells containing GSH and PSH by treatment with 20 μM or 100 μM diamide, and was reduced slowly in the permeated cells containing no GSH. The above dynamic results were similar to the results obtained from the cell-free sample as shown in FIGS. 2e and 2c. The present inventors found similar results in a $H_2O_2$ treatment experiment (data now shown).

Taken together, the above experimental results demonstrated that the FreSH-tracer reacts more preferentially with GSH than with PSH among intracellular thiols.

Figure 3A:
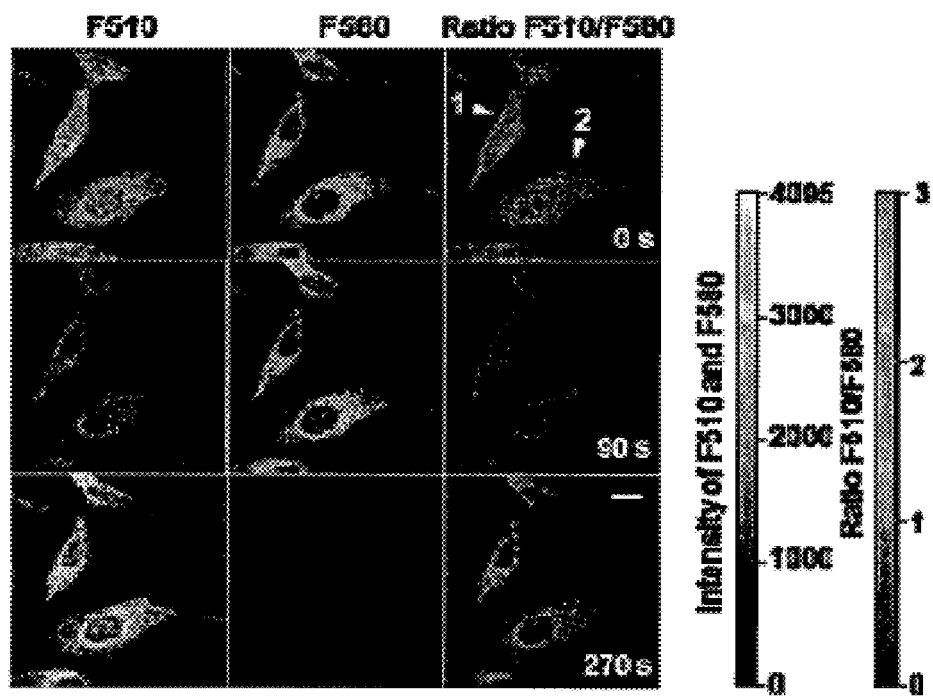
FIGS. 3a-3h indicate that the level of thiols in living cells can be imaged with the FreSH-tracer.
Figure 3B:
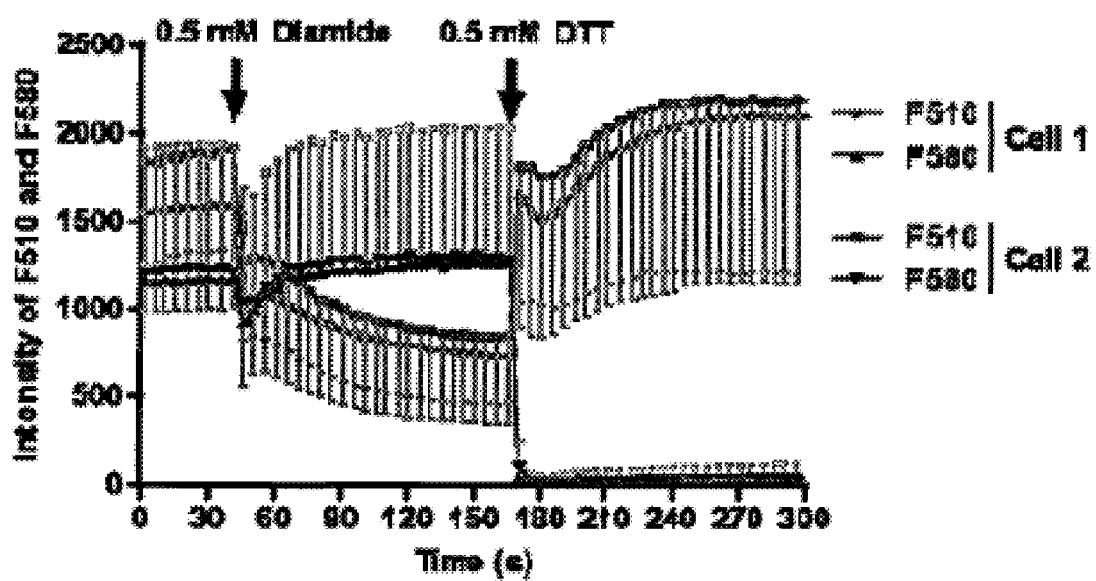
Figure 3C:
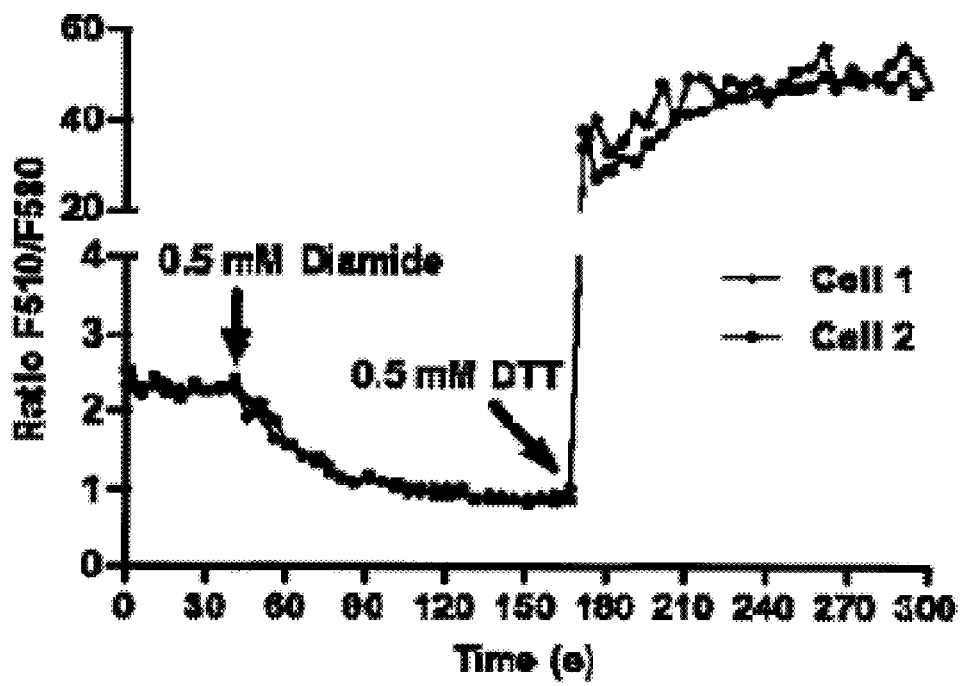
Figure 3D:
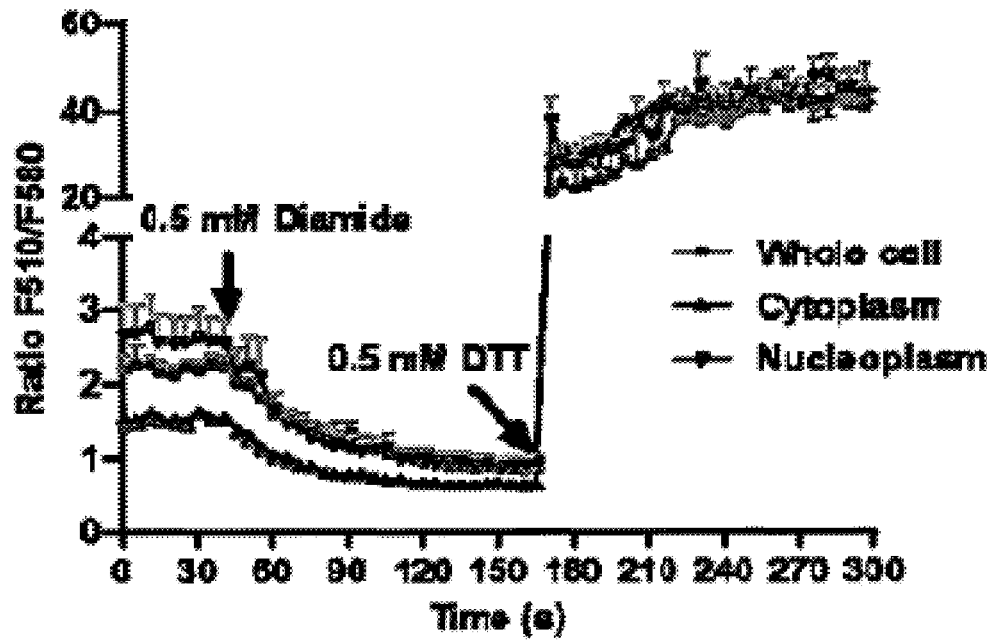
Figure 13:
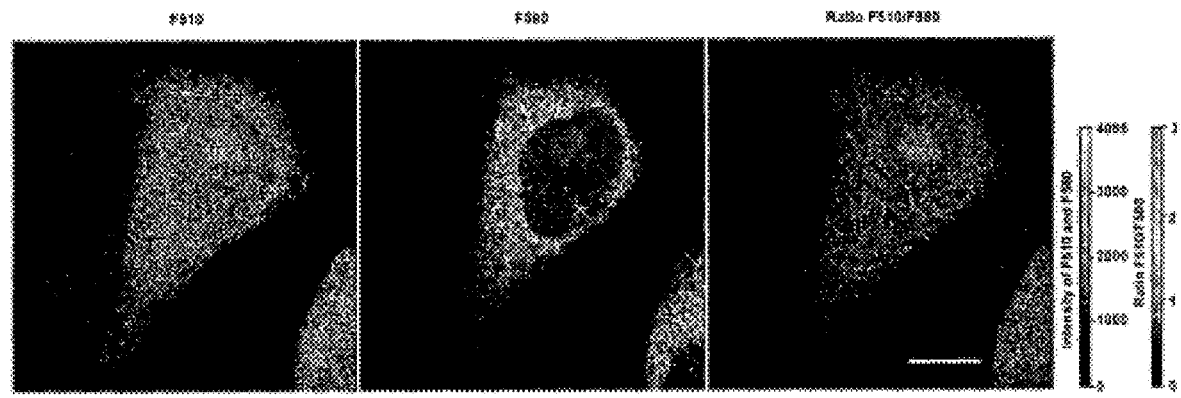
FIG. 13 shows representative images of HeLa cells loaded with the FreSH-tracer.
Figure 14A:
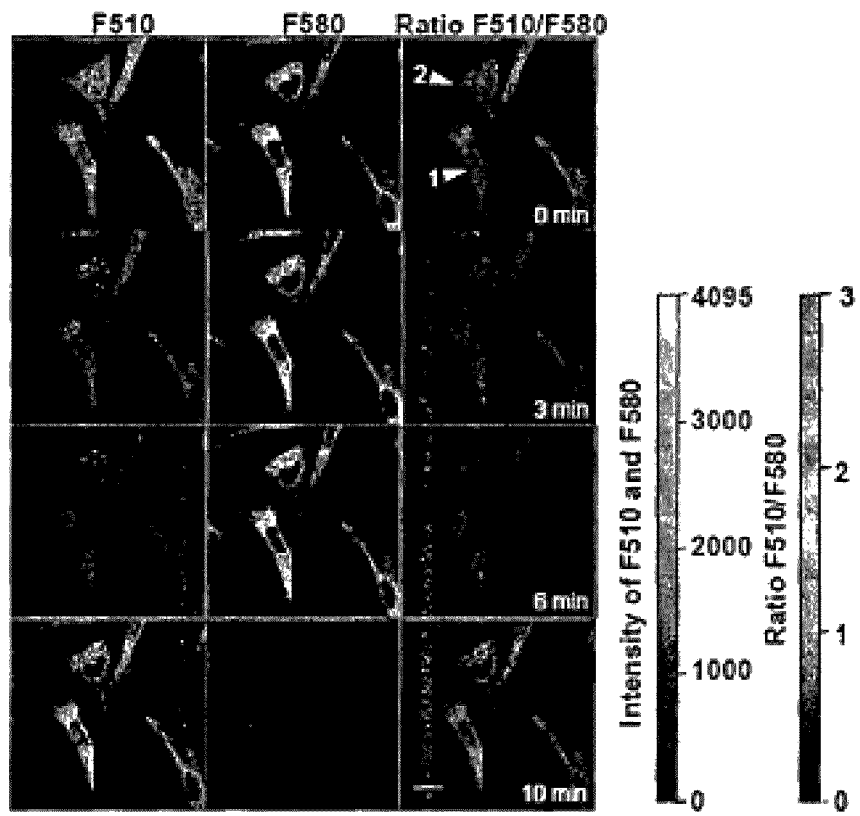
FIGS. 14a to 14d show the effects of NEM and DTT (dithiothreitol) intracellular thiol levels.
Figure 14B:
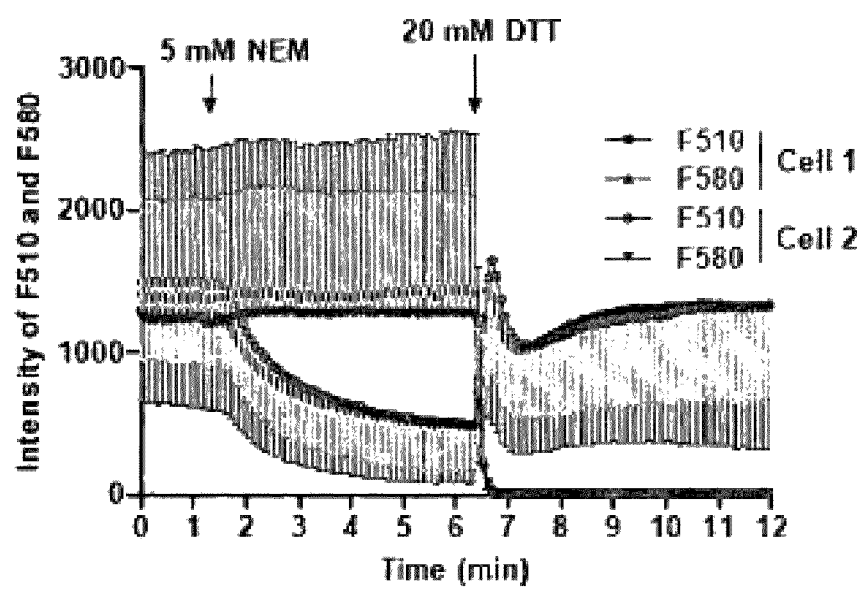
Figure 14C:
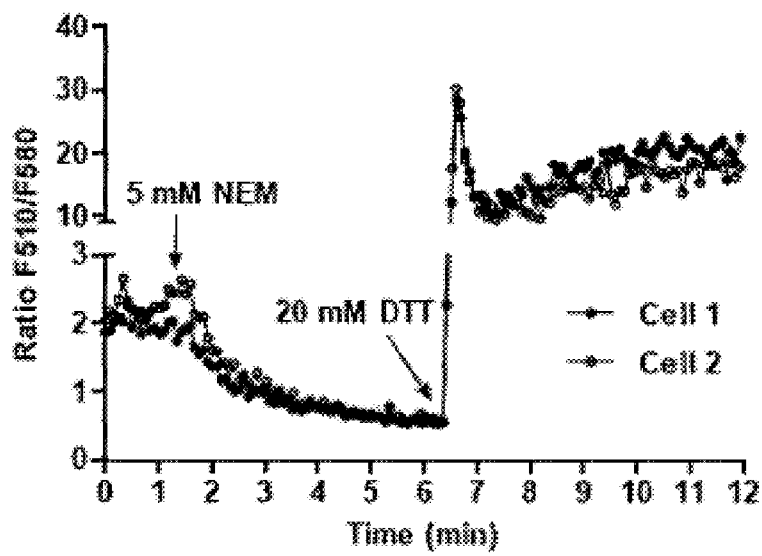
Figure 14D:
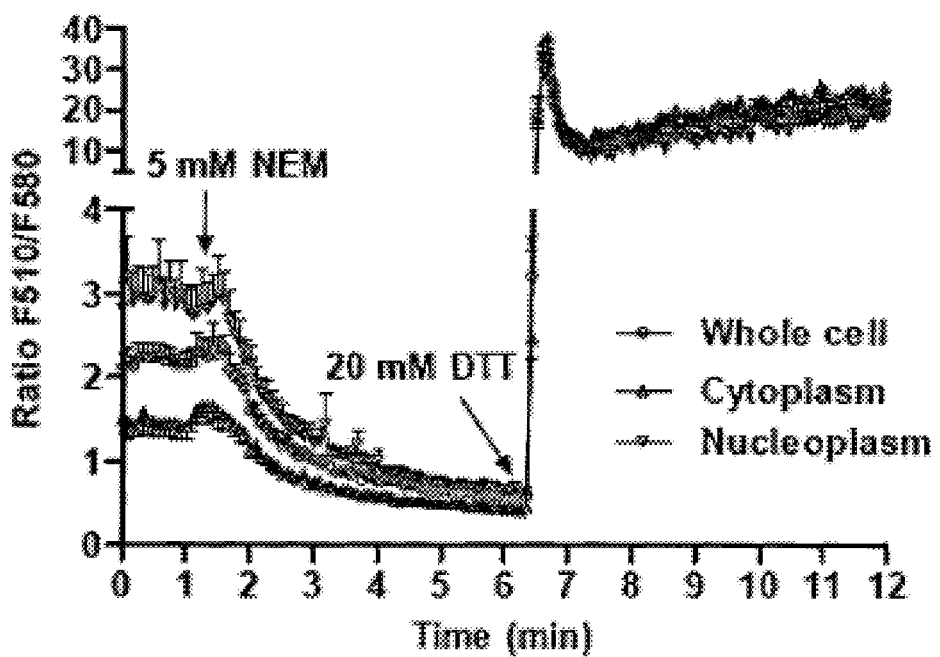
Figure 15A:
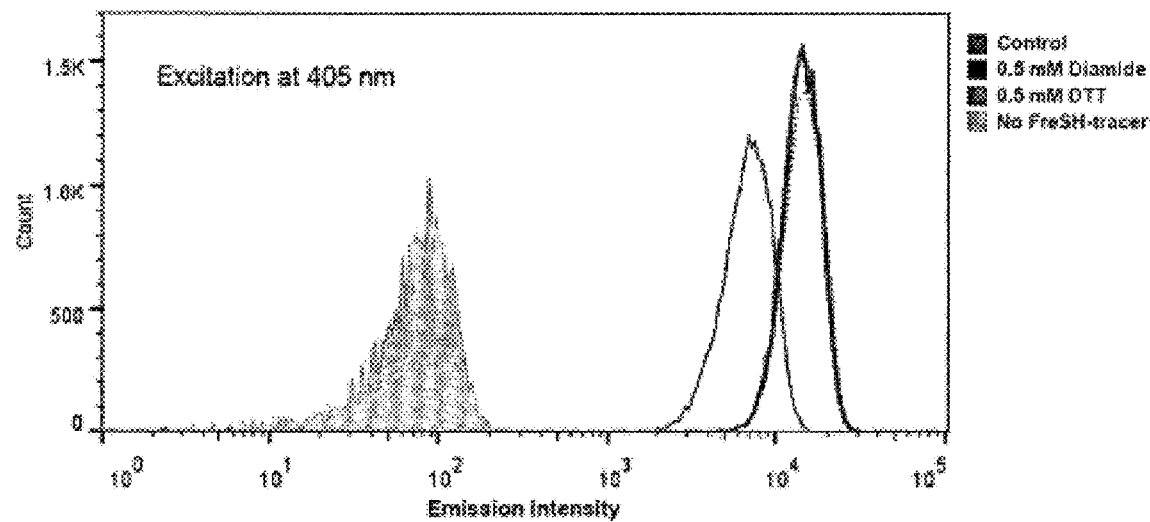
FIGS. 15a to 15c show the results of analyzing FreSH-tracer-treated HeLa cells by flow cytometry.
Figure 15B:
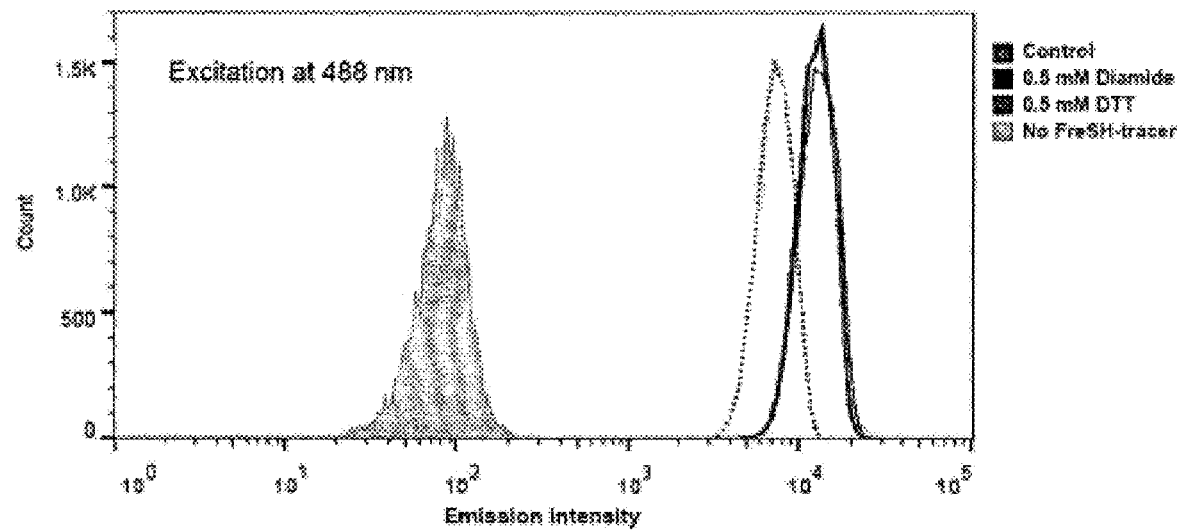
Figure 15C:
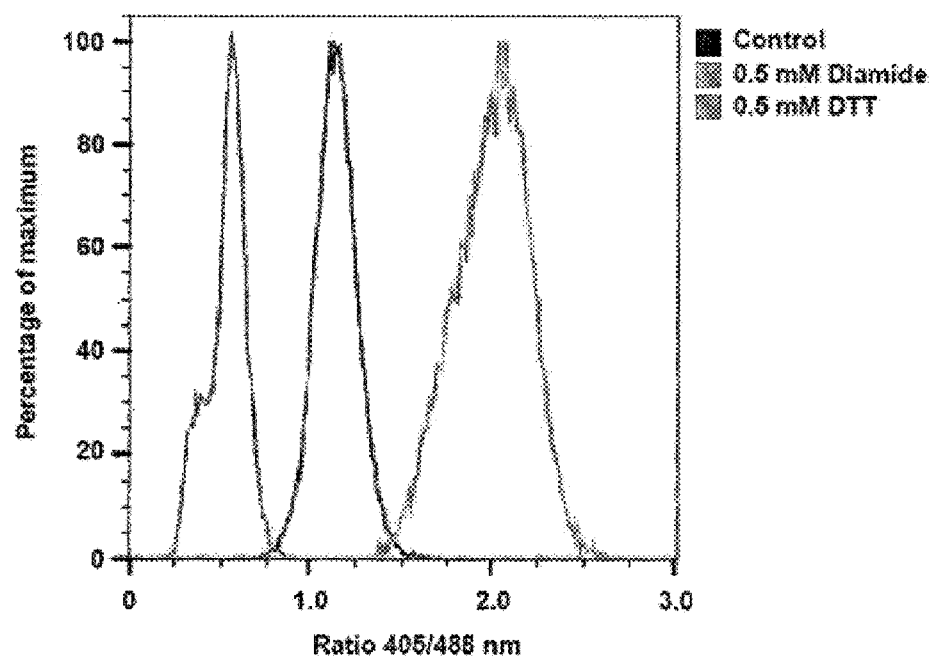
Figure 16A:
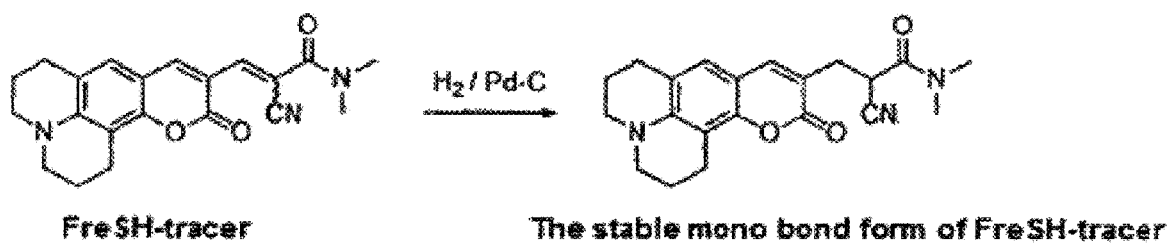
FIGS. 16a to 16i indicate that the stable single bond form of a derivative that changed from the FreSH-tracer having a coumarin double bond is not sensitive to treatment with thiol oxidizing agents (diamide and $H_2O_2$) in HeLa cells.
Figure 16B:
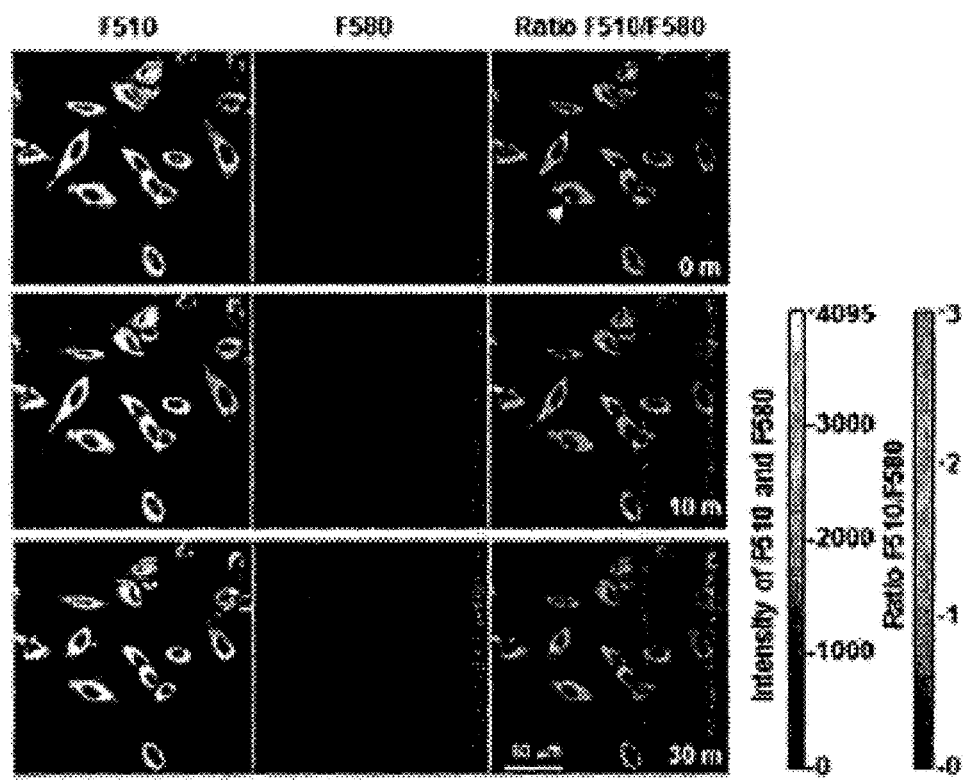
Figure 16C:
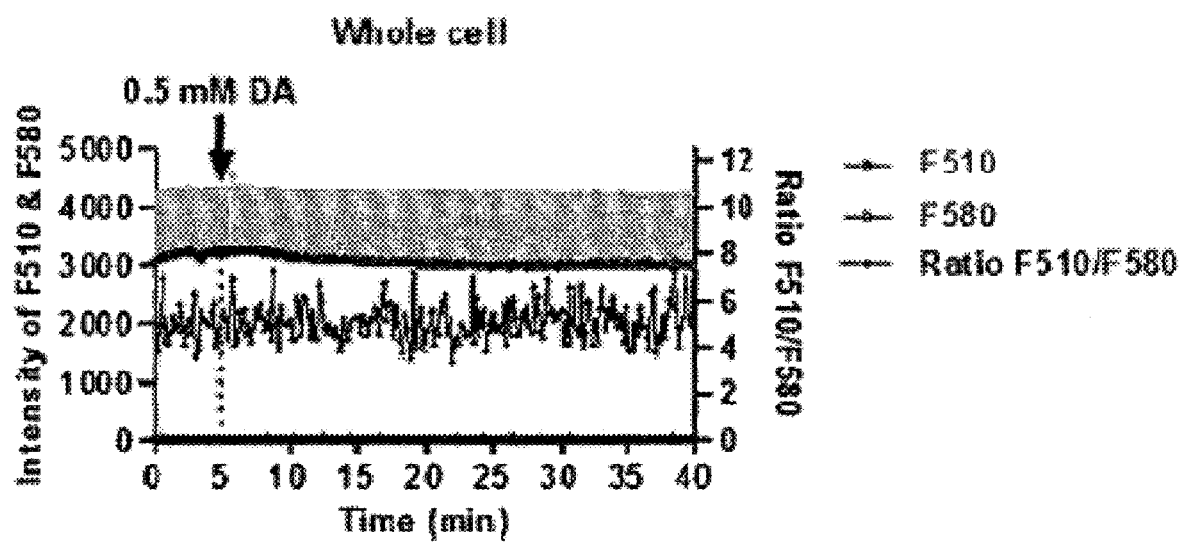
Figure 16D:
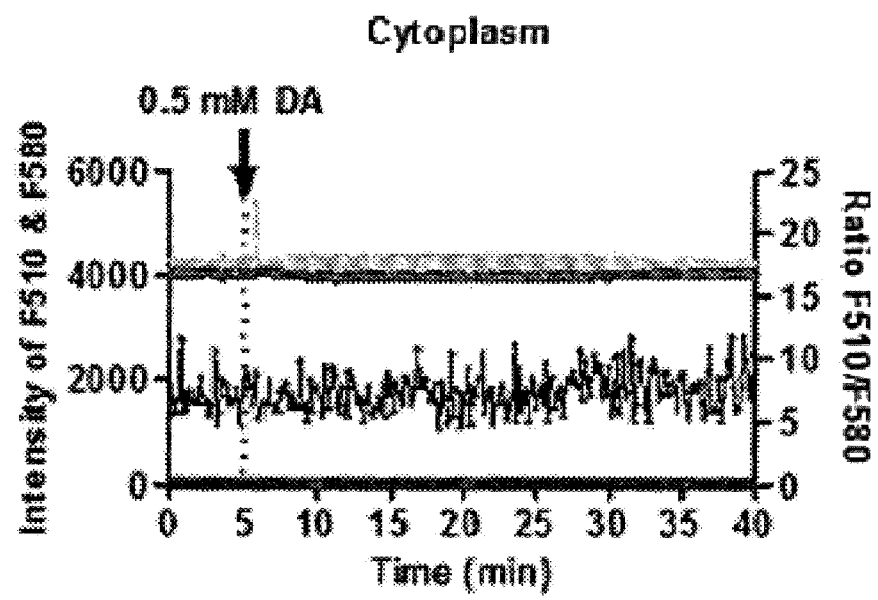
Figure 16E:
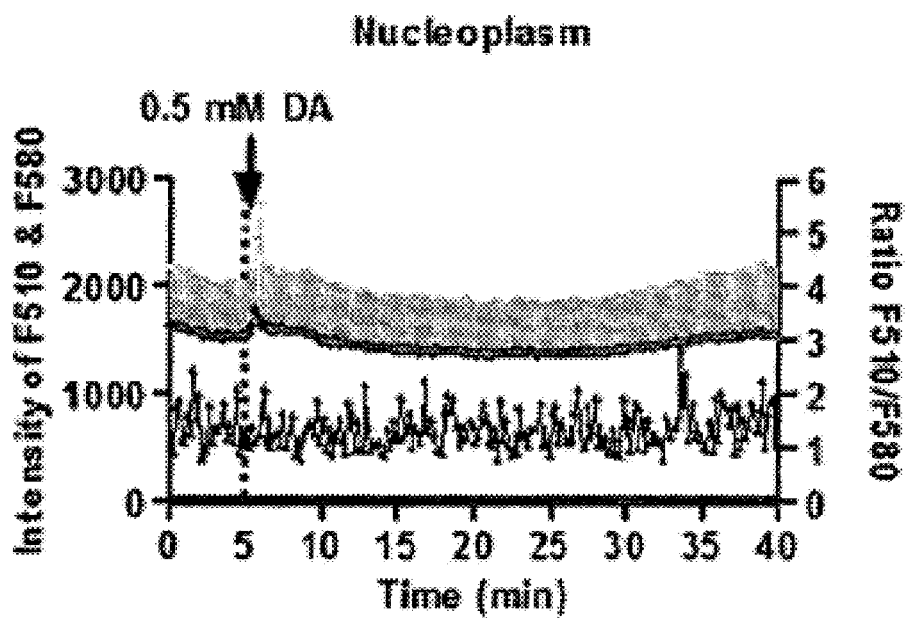
Figure 16F:
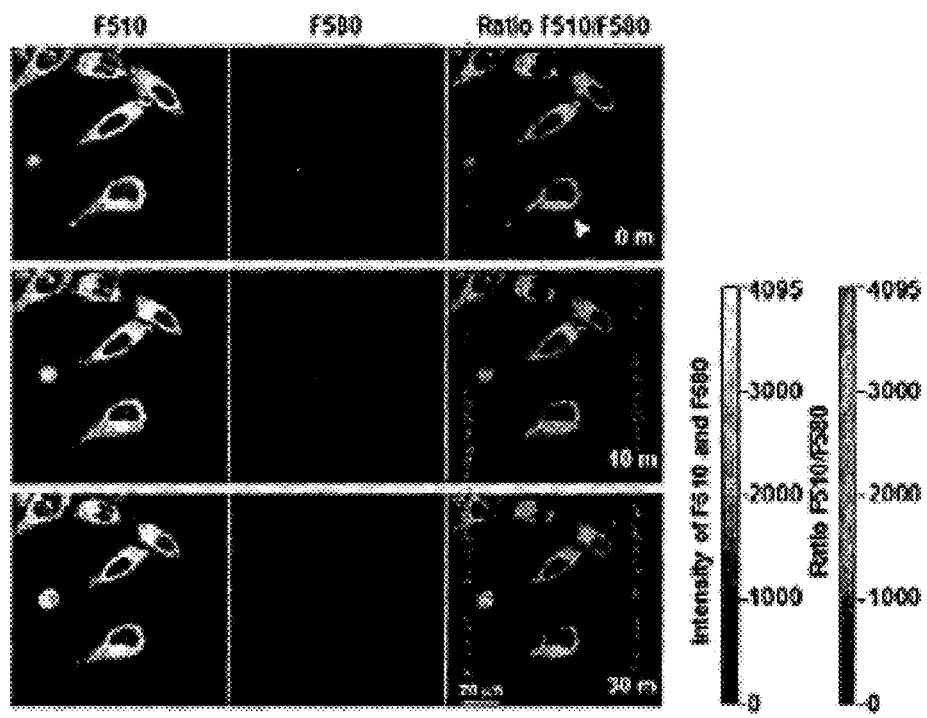
Figure 16G:
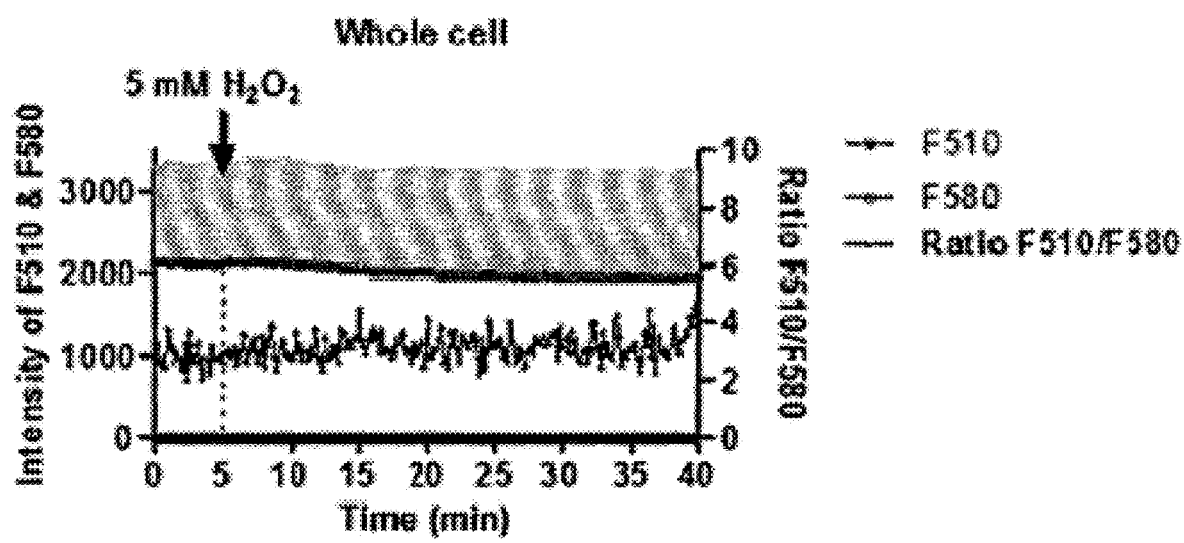
Figure 16H:
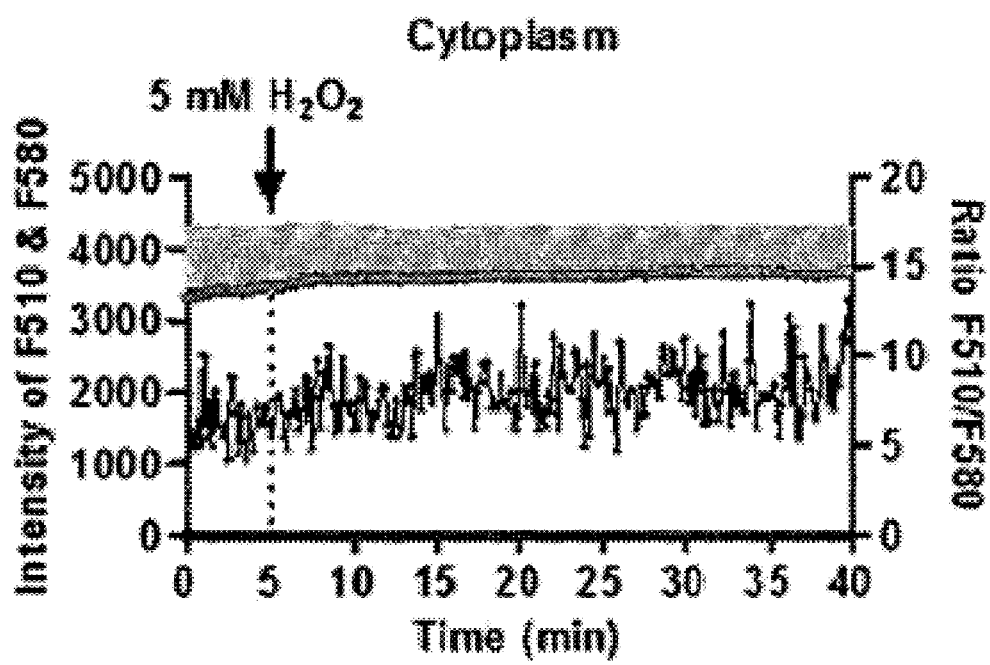
Figure 16I:
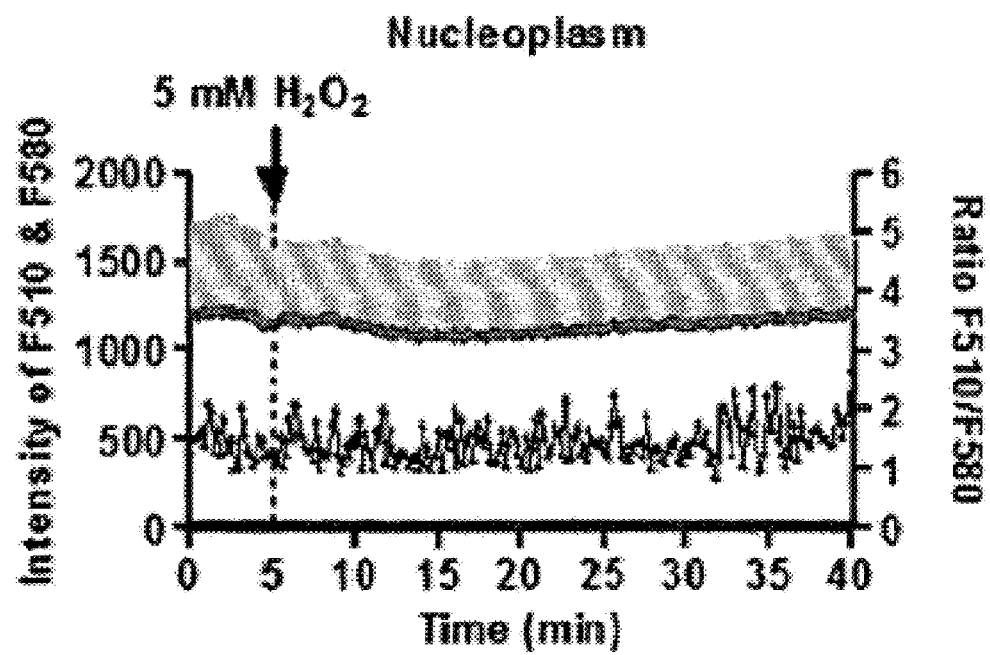

3. Visualization of Changes in Levels of Thiols in Living Cells by Ratiometric Analysis of FreSH-Tracer The present inventors studied the applicability of the FreSH-tracer to examination of changes in the levels of thiols in living cells. The present inventors could describe intracellular thiol levels as false color images based on the fluorescence intensity ratio measured by confocal microscope measurement during culture of HeLa cells in medium supplemented with 5 μM nontoxic FreSH-tracer for at least 24 hours (FIG. 13). In the present invention, in order to examine whether the sensor responds to the oxidation/reduction conditions of intracellular thiols, living cells loaded with the sensor were treated with 0.5 mM diamide to oxidize intracellular thiols, and after 125 seconds, 0.5 mM dithiothreitol (DTT) was added to the medium to reduce intracellular thiols. It was found that, when diamide and DTT were added to the culture medium, an immediate sensor reaction in the living cells was induced (FIGS. 3a to 3d). The emission intensity of F510 was reduced rapidly by treatment with diamide and returned immediately by addition of DTT, and the F580 signal changed in a completely different pattern (FIGS. 3a and 3b). The sensor fluorescence intensity ratio calculated from images of the living cells was reduced by treatment with diamide, and oversaturated rapidly by addition of DTT because of a direct reaction between the sensor and DTT (FIGS. 3a and 3b). The fluorescence intensity ratio of the nucleoplasm was higher than that of the cytoplasm, but there was no difference in the ratio change pattern between the two areas (FIGS. 3a and 3d). The present inventors could generalize the above results using NEM (FIGS. 14a to 14d). Furthermore, using flow cytometry, the present inventors could obtain the results that indicate that the fluorescence intensity ratio of the sensor in living HeLa cells is changed in the same pattern by treatment with diamide and DTT (FIGS. 15a to 15c). However, the FreSH-tracer-derived compound that continuously emits only F510 fluorescence without reacting with thiols did not respond to treatment with the oxidizing agent (FIGS. 16a to 16i). Thus, it was found that the fluorescence intensity of the FreSH-tracer is not influenced directly by treatment with the oxidizing agent.

Figure 3E:
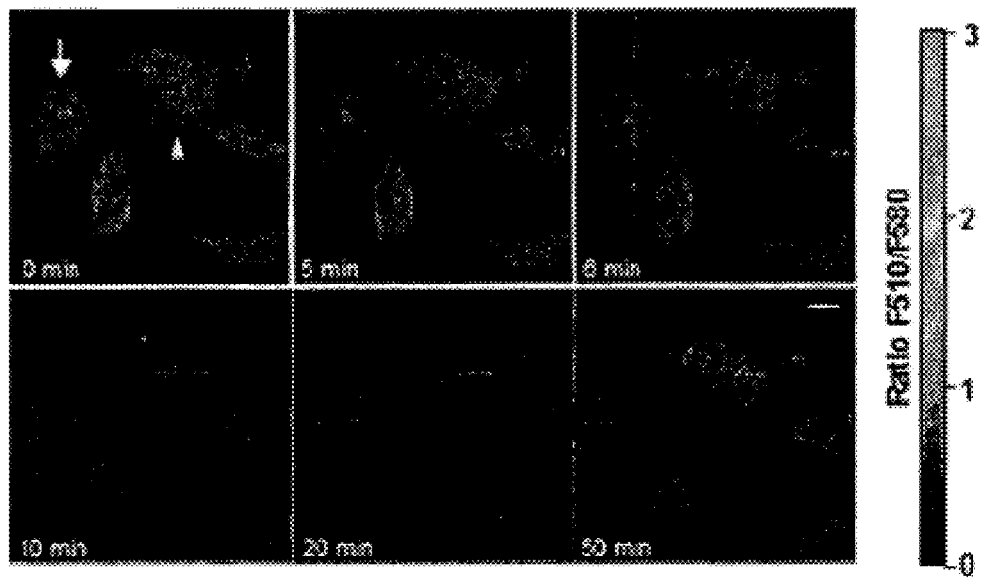
Figure 3F:
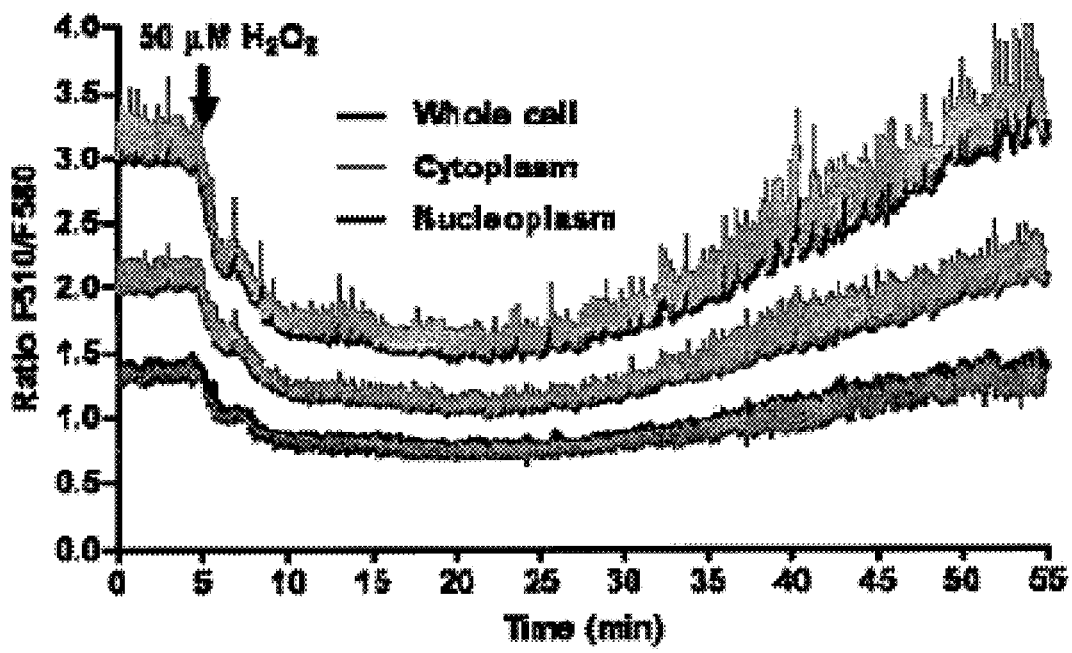
Figure 3G:
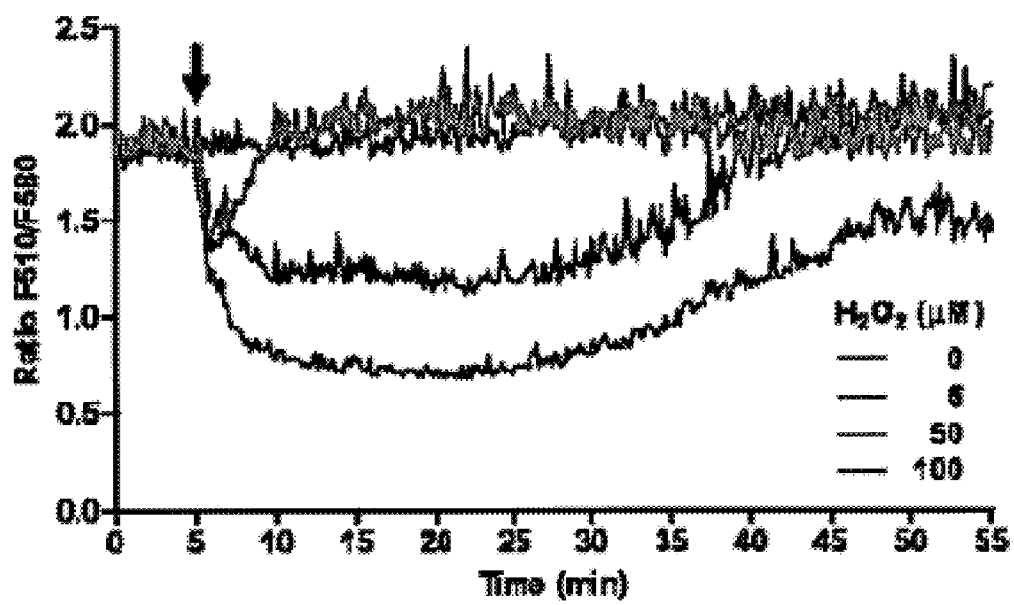
Figure 3H:
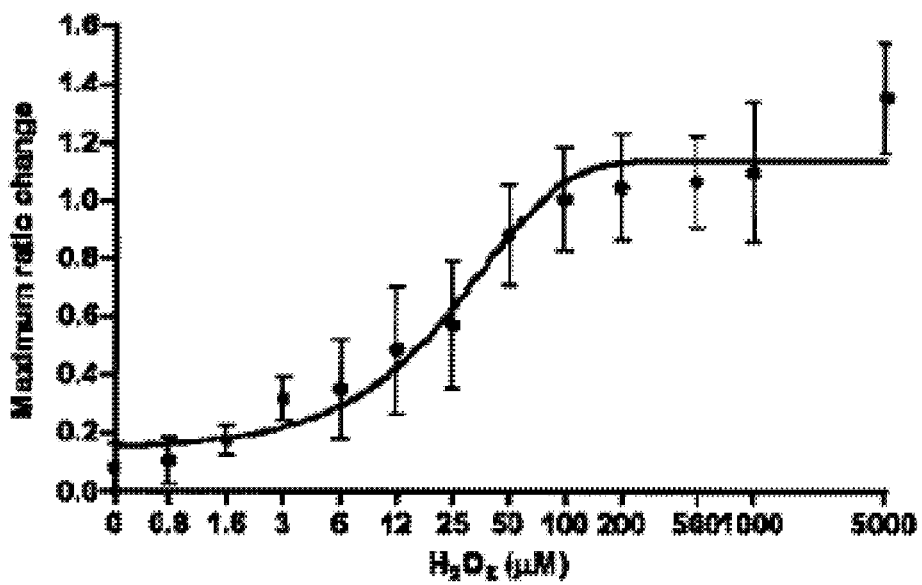
Figure 17A:
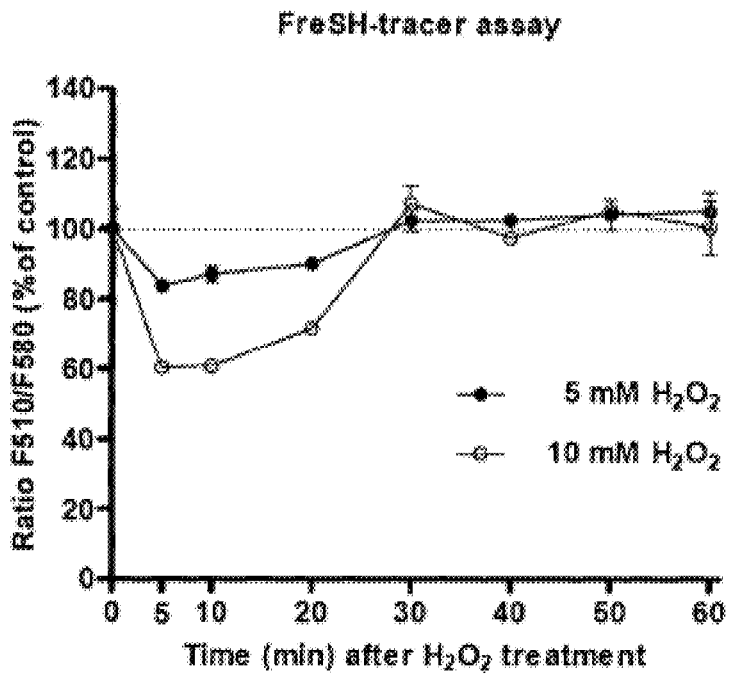
FIGS. 17a to 17c show the results of measuring the level of thiols in a lysate of HeLa cells, treated with $H_2O_2$ for the indicated time, using the FreSH-tracer (FIG. 17a) and Ellman's reagent (FIG. 17b), and show the results of measuring the level of reduced GSH by a GSH quantitative kit using GSH reductase (FIG. 17c).
Figure 17B:
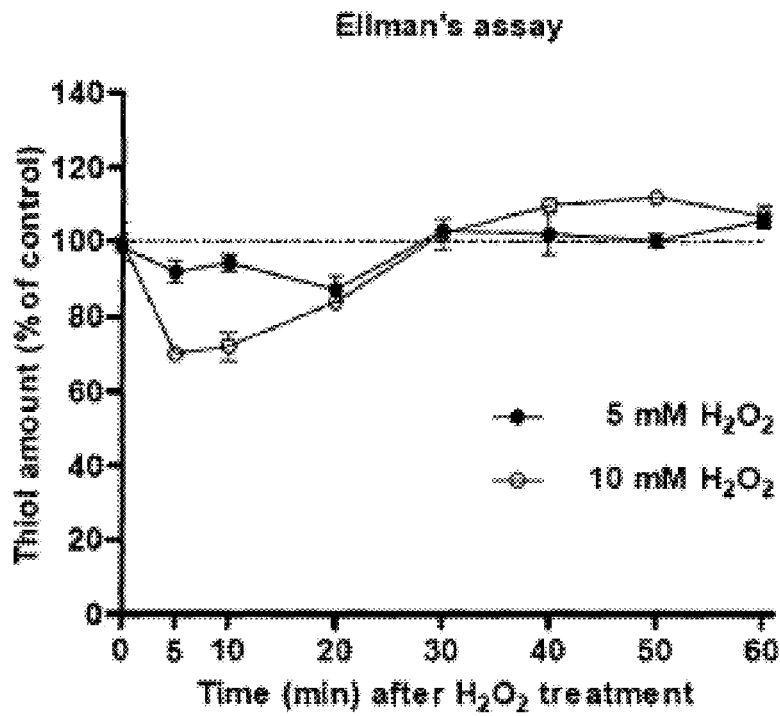
Figure 17C:
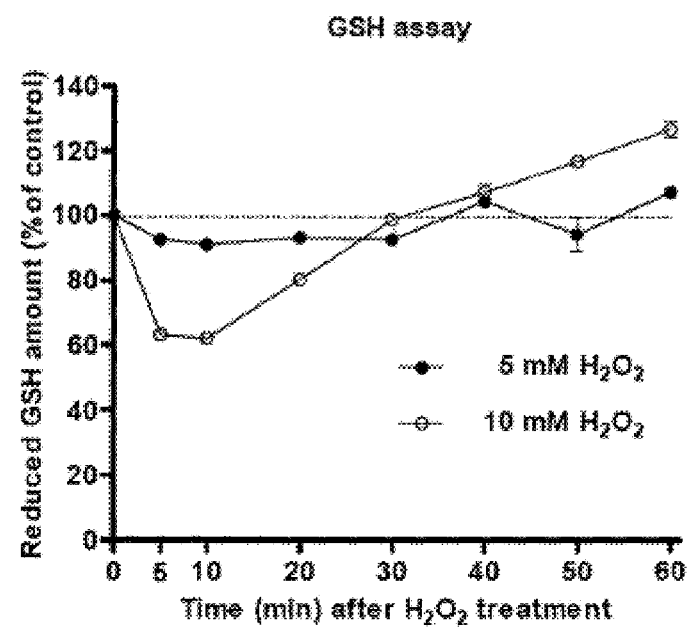

Afterwards, the present inventors used the FreSH-tracer to observe the oxidation/reduction reactions of cells with $H_2O_2$. When cells loaded with the sensor were treated with 50 μM $H_2O_2$, the fluorescence intensity ratio of the sensor was immediately reduced for about 5 minutes and started to be generally returned after about 20 minutes. This shows that an effective antioxidant response to oxidative stress in living cells occurs (FIGS. 3e and 3f). There was no difference in the fluorescence intensity ratio between the cytoplasm and the nucleoplasm (FIG. 3f). Afterwards, in order to measure the reactivity of the sensor as a function of the intensity of oxidative stress, the present inventors treated living cells with various amounts of $H_2O_2$, and then observed the reaction of the sensor. As the amount of $H_2O_2$ treated increased, the time for the fluorescence intensity ratio of the sensor to return increased, and the maximum change in the fluorescence intensity ratio also increased (FIGS. 3g and 3h). The present inventors obtained similar results through an experiment that measures the change in the thiol oxidation level in a lysate of HeLa cells, treated with 5 and 10 mM $H_2O_2$, by use of the FreSH-tracer and Ellman's reagent (FIGS. 17a and 17b). When the amount of GSH in the same sample was analyzed, the pattern of change in the level of reduced GSH was the same as the pattern of change in the thiol level in the whole cells (FIG. 17c).

The above experimental results demonstrated that the fluorescence intensity ratio of the FreSH-tracer in living cells generally indicates the amount of reduced GSH.

Figure 18A:
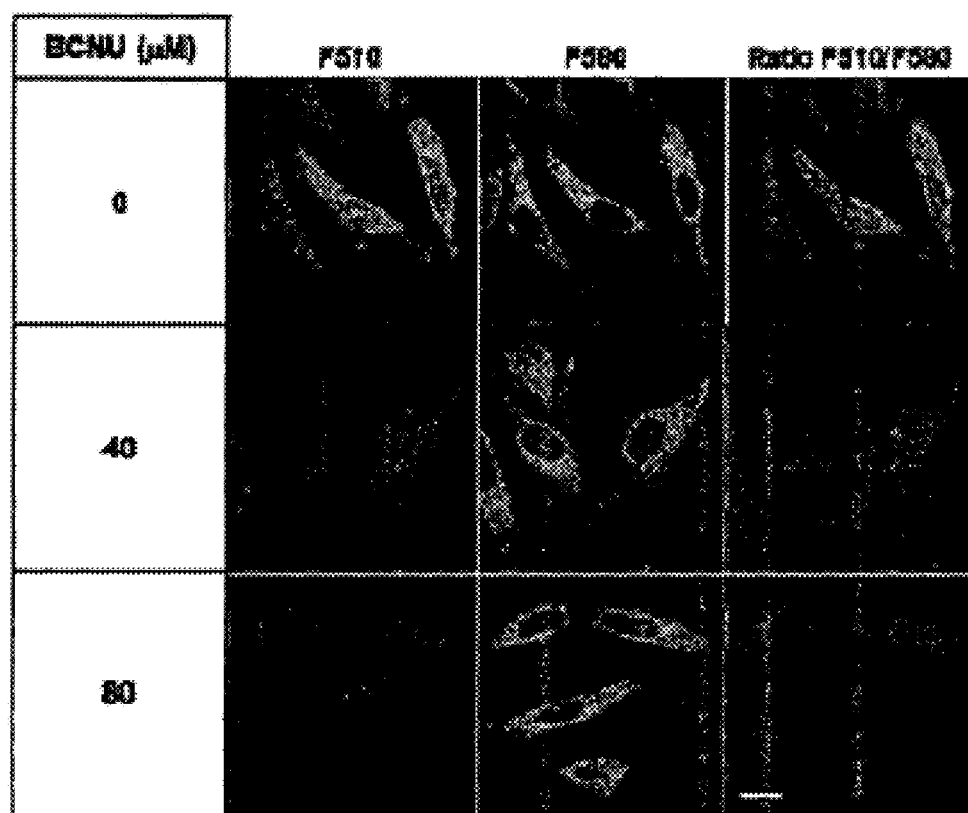
FIGS. 18a and 18b show the effects of treatment with the GSH reductase inhibitor BCNU (bis-chloroethylnitrosourea, FIG. 18a) and the gamma-glutamyl cysteine synthetase inhibitor BSO (buthionine sulfoximine, FIG. 18b) on the level of thiols in HeLa cells.
Figure 18A:
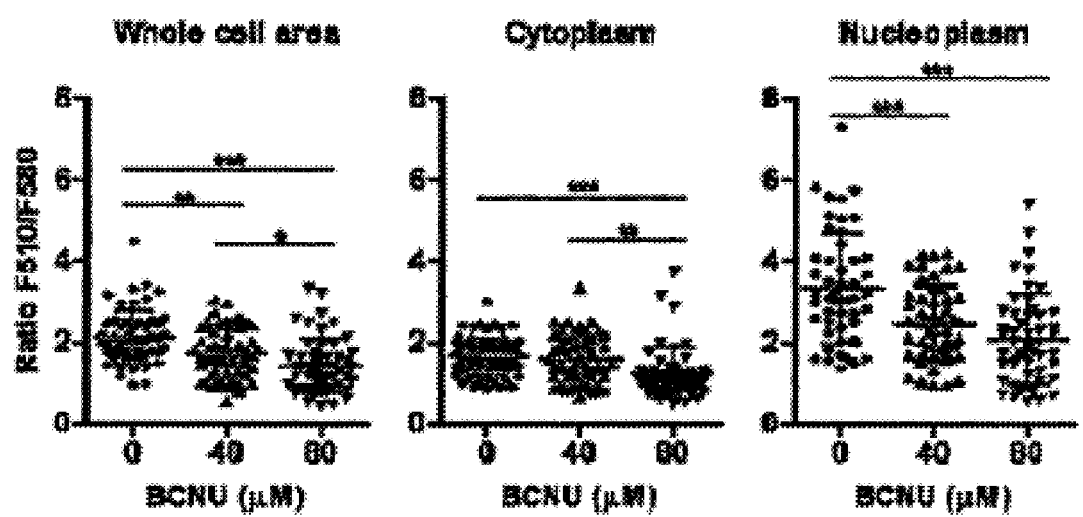
Figure 18B:
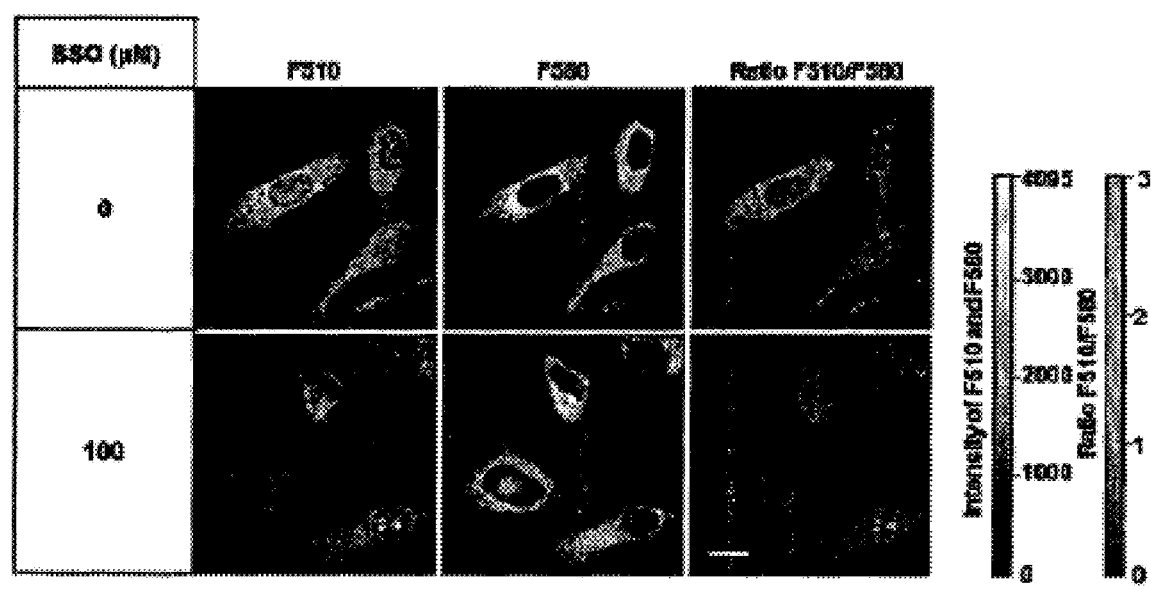
Figure 18B:
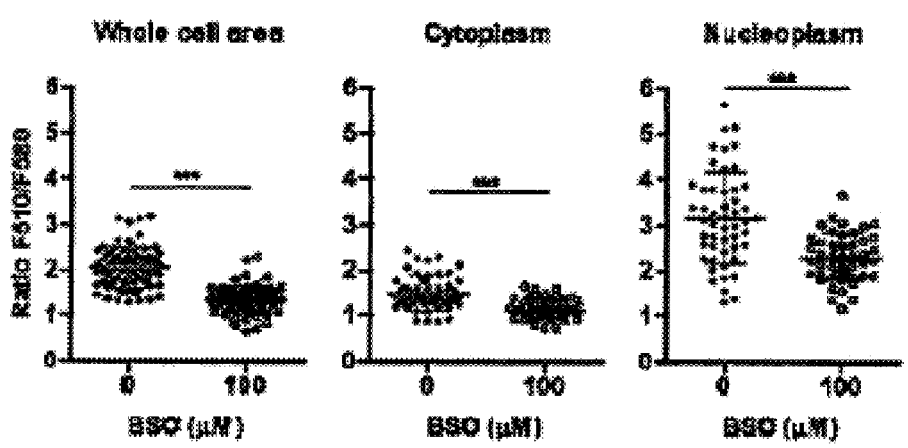
Figure 19A:
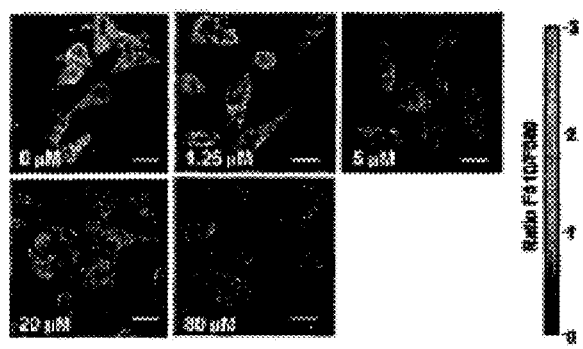
FIGS. 19a and 19b show the relationship between the GSH level measured in a lysate of HeLa cells treated with various concentrations of BSO and the fluorescence intensity ratio measured using a fluorescence microscope (FIG. 19a) and flow cytometry (FIG. 19b) after treating living cells with the FreSH-tracer under the same conditions.
Figure 19A:
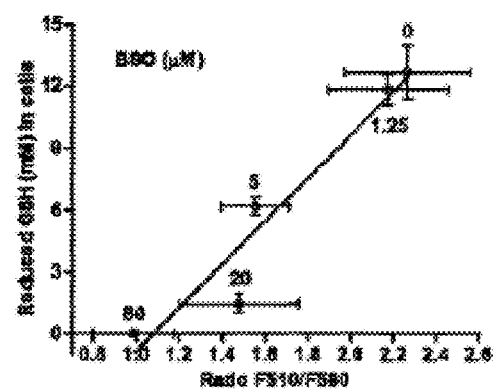
Figure 19B:
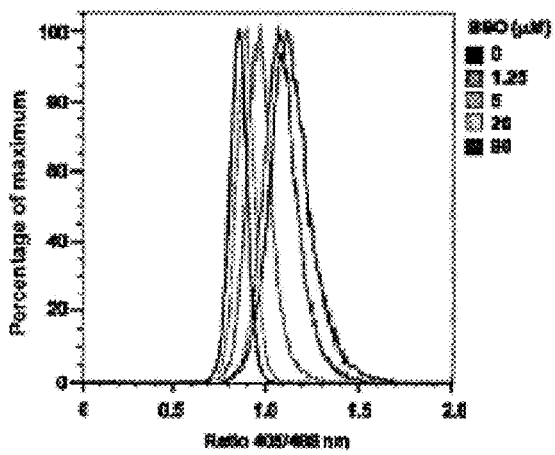
Figure 19B:
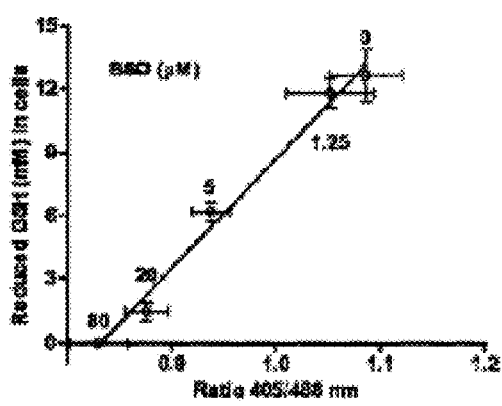

4. Detection of Intracellular GSH Level, which Changed by Treatment with GSH-Related Enzyme Inhibitor, by Use of FreSH-Tracer In the present invention, in order to confirm whether the change in intracellular GSH level caused by inhibition of GSH metabolism-related enzymes can be detected by the FreSH-tracer, the cell culture was treated with the glutathione reductase inhibitor bis-chloroethylnitrosourea (BCNU) and the γ-glutamyl cysteine synthetase inhibitor buthionine sulphoximine (BSO) to reduce the level of reduced GSH in the HeLa cells, and the FreSH-tracer was added to the culture for 2 hours before measurement of the fluorescence intensity ratio, followed by measurement of the fluorescence intensity ratio of the sensor. The fluorescence intensity ratio of the sensor was reduced by treatment with the two inhibitors (FIGS. 18a and 18b). The tendency of a decrease in the fluorescence intensity ratio was observed in the whole intracellular area including the cytoplasm and the nucleoplasm (FIGS. 18a and 18b). In order to further examine the relationship between the fluorescence intensity ratio of the sensor and the level of GSH in living cells, the present inventors treated HeLa cells with various concentrations of BSO for 24 hours. The living cells were treated with the FreSH-tracer, and then the sensor fluorescence intensity ratio, measured using a microscope and flow cytometry, and the concentration of reduced GSH in a lysate of the cells, quantitatively analyzed under the same conditions, were compared. When the measured sensor fluorescence intensity ratio and the amount of reduced GSH were graphically shown, it was found that the graphs all had a linear relationship (FIGS. 19a and 19b). In other words, it can be seen that the fluorescence intensity ratio of the FreSH-tracer, measured in the BSO-treated cells, indicates the level of reduced GSH in the cells.

Figure 20A:
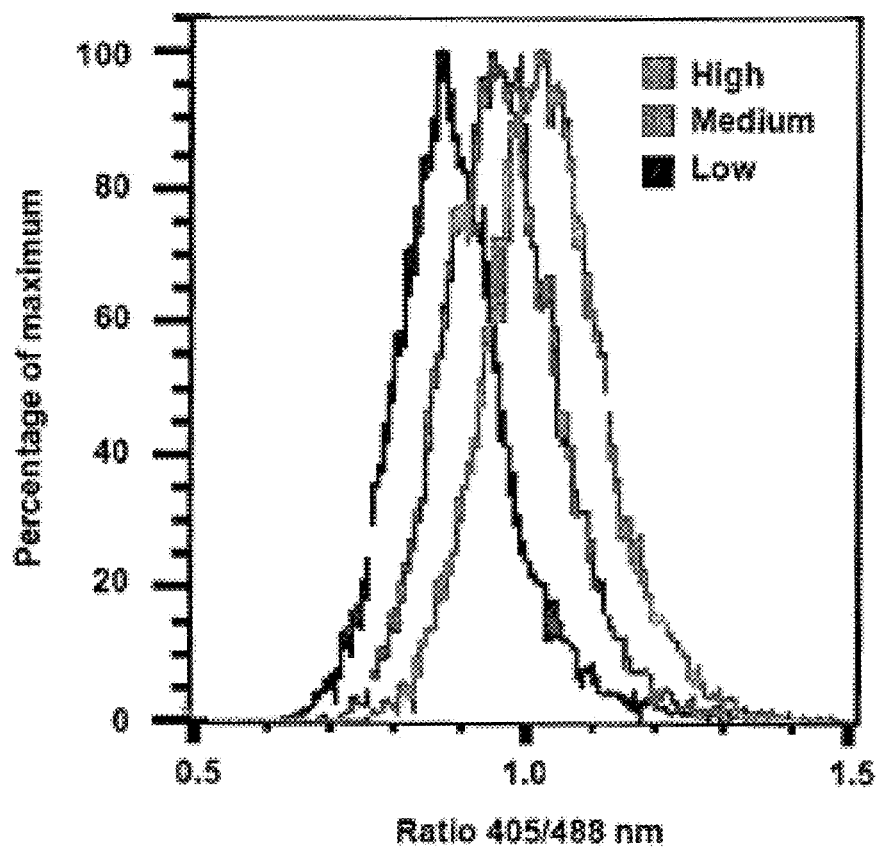
FIGS. 20a and 20b show the results of measuring the level of reduced thiols in living cells, which change depending on the density of cultured cells, by flow cytometry.
Figure 20B:
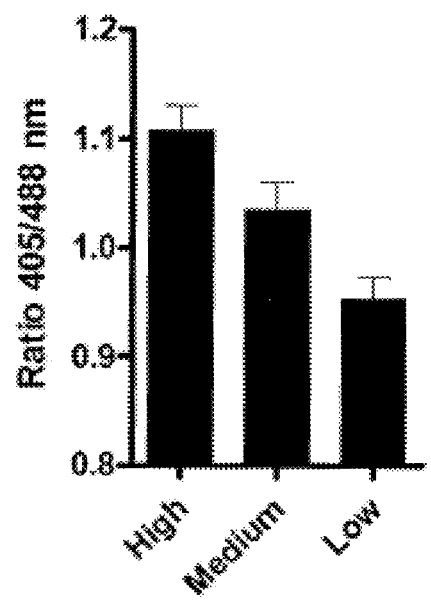
Figure 21A:
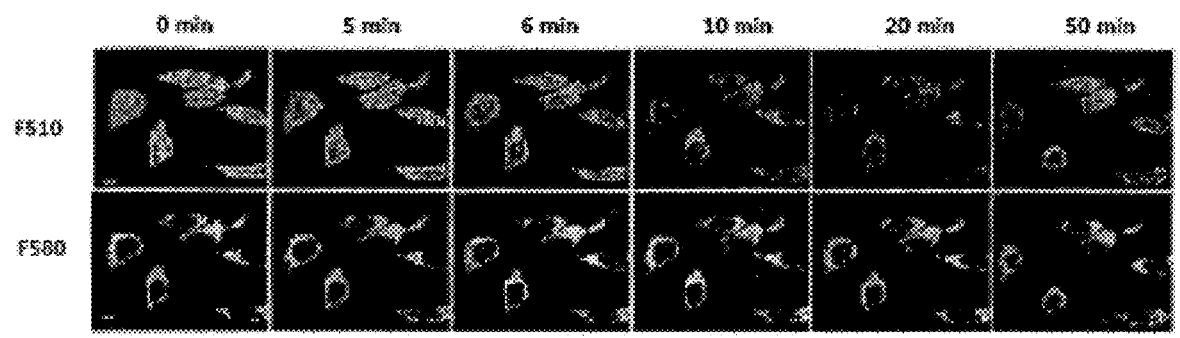
FIGS. 21a to 21d show images of fluorescence emission intensities.
Figure 21B:
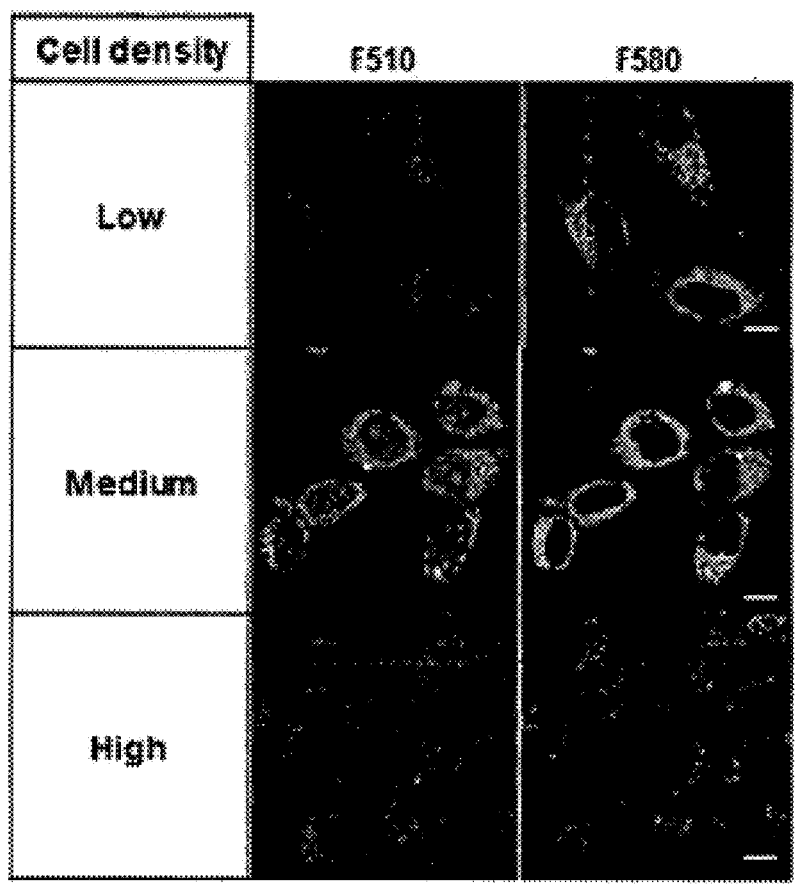
Figure 21C:
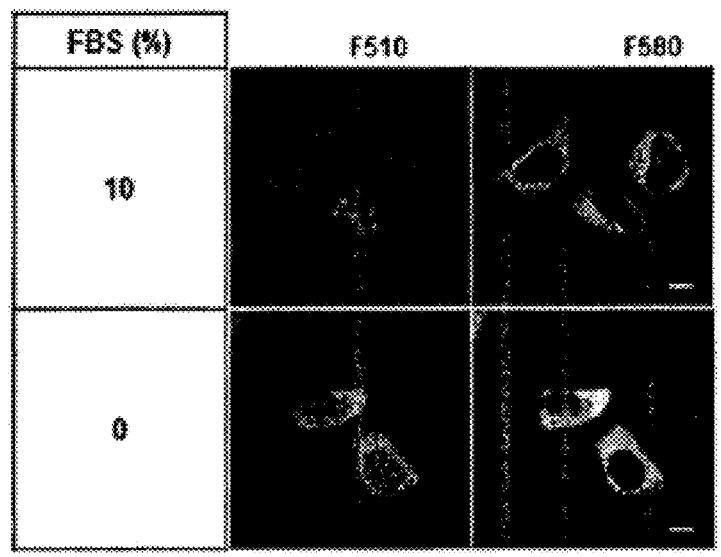
Figure 21D:
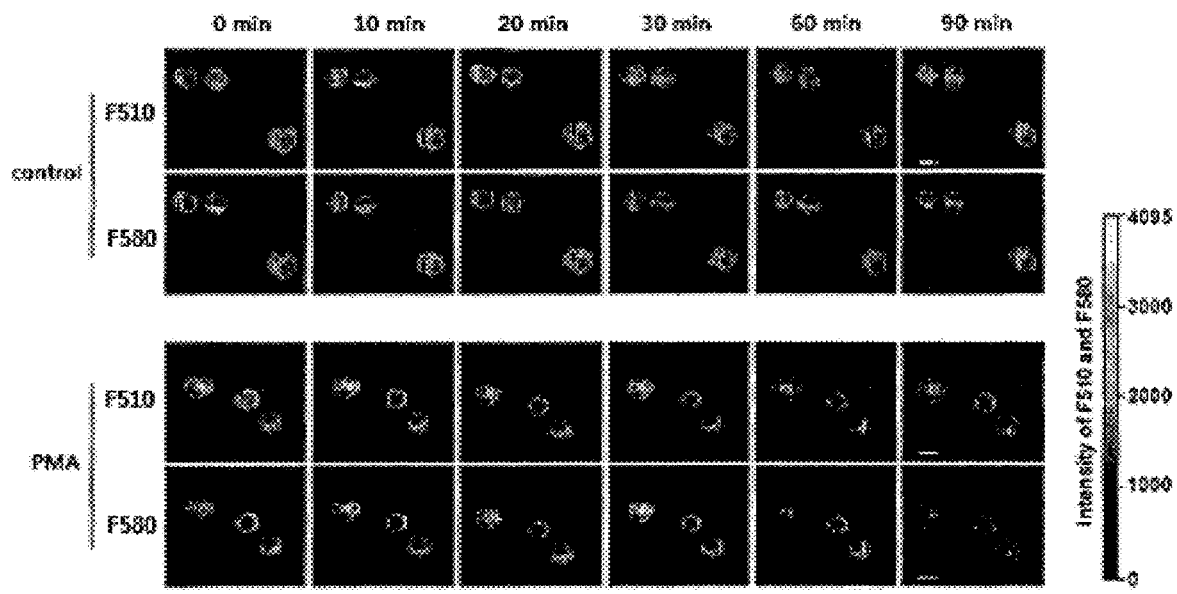
Figure 22A:
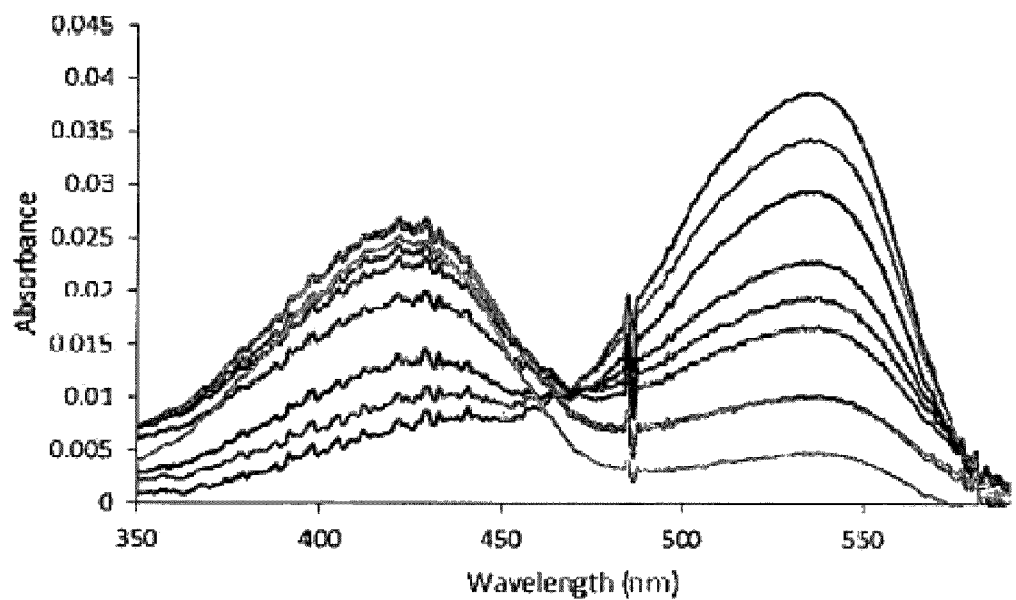
FIGS. 22a to 22c show the results of measuring the reversible reaction of the compound represented by formula 2 by the UV-Vis absorption spectrum (FIG. 22a), and show the fluorescence emission spectra (FIGS. 22b and 22c) obtained by measuring the reaction with the compound of formula 2 after equilibration with β-mercaptoethanol (Kd=12±1 mM).
Figure 22B:
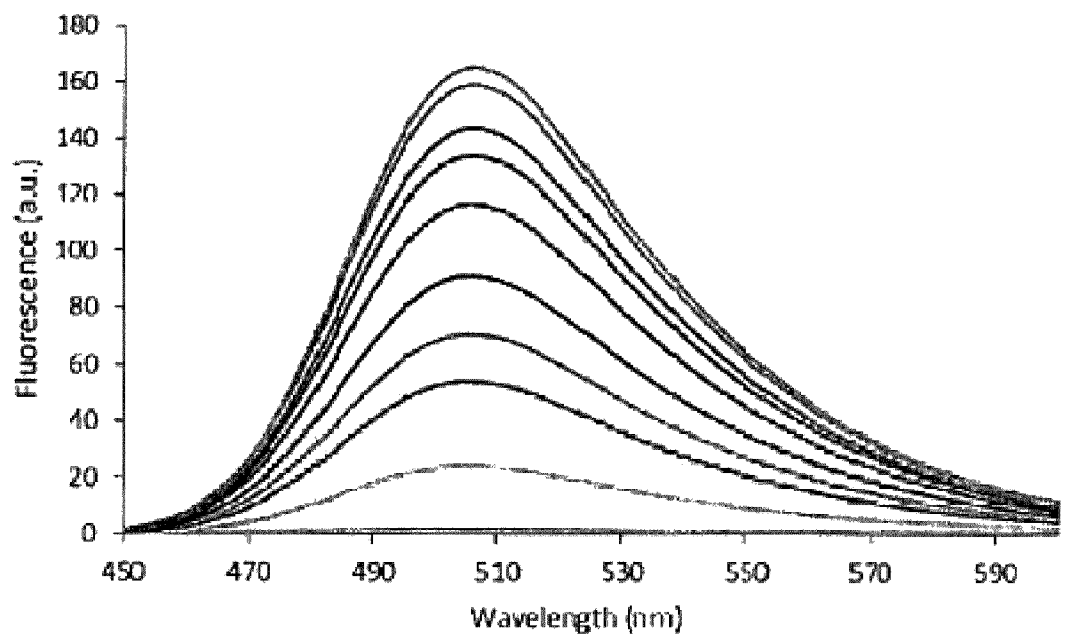
Figure 22C:
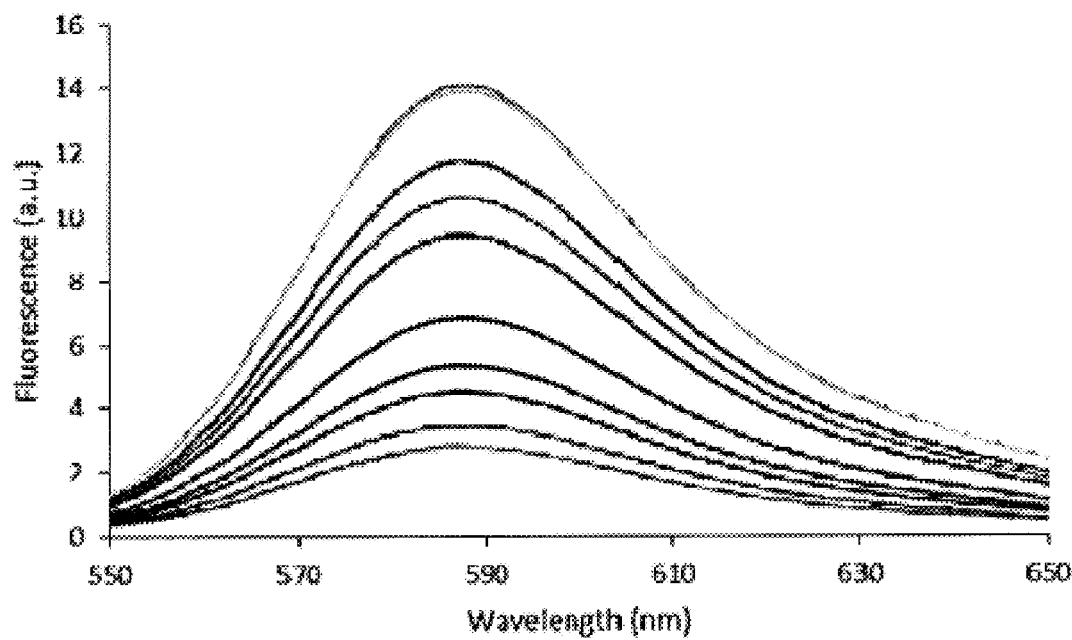
Figure 23A:
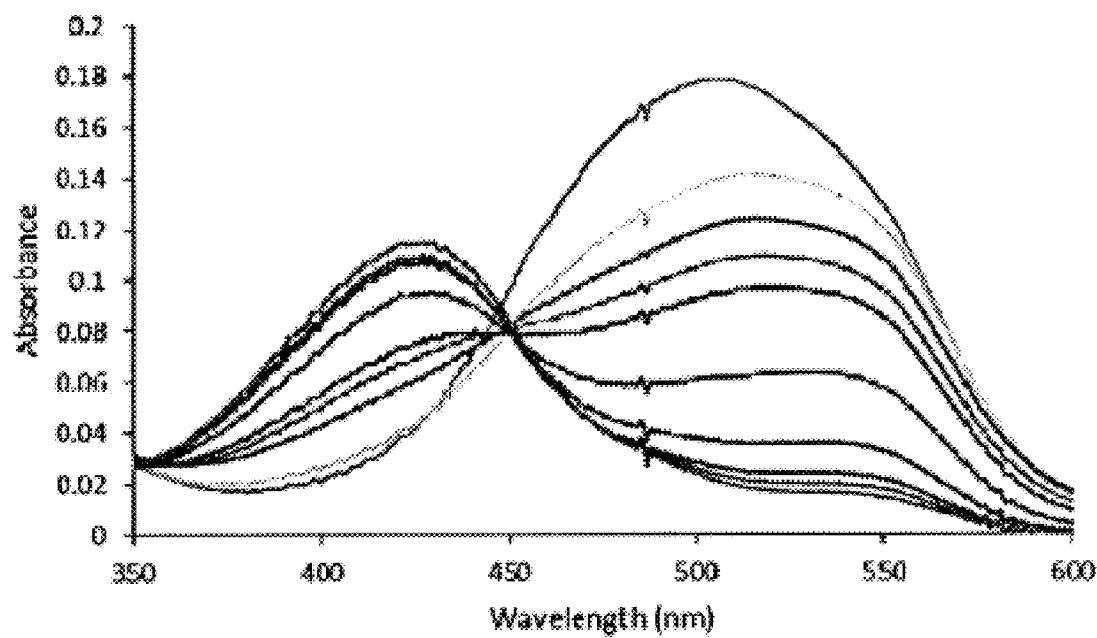
FIGS. 23a to 23c show the results of measuring the reversible reaction of the compound represented by formula 3 by the UV-Vis absorption spectrum (FIG. 23a), and show the fluorescence emission spectra (FIGS. 23b and 23c) obtained by measuring the reaction with the compound of formula 3 after equilibration with β-mercaptoethanol (Kd=14±1 mM).
Figure 23B:
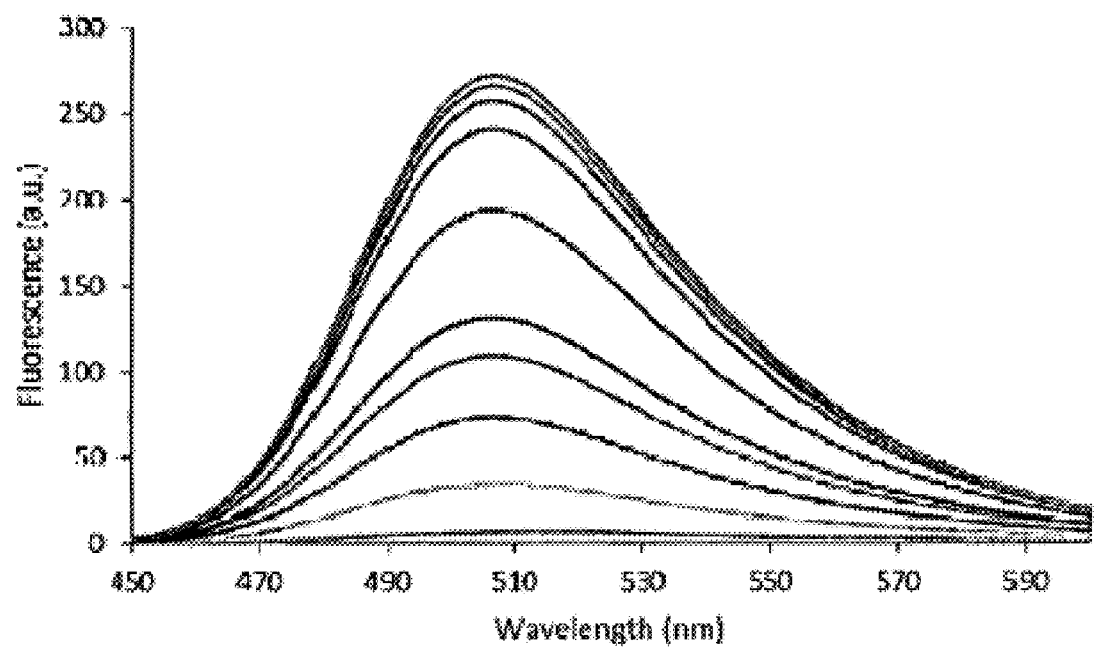
Figure 23C:
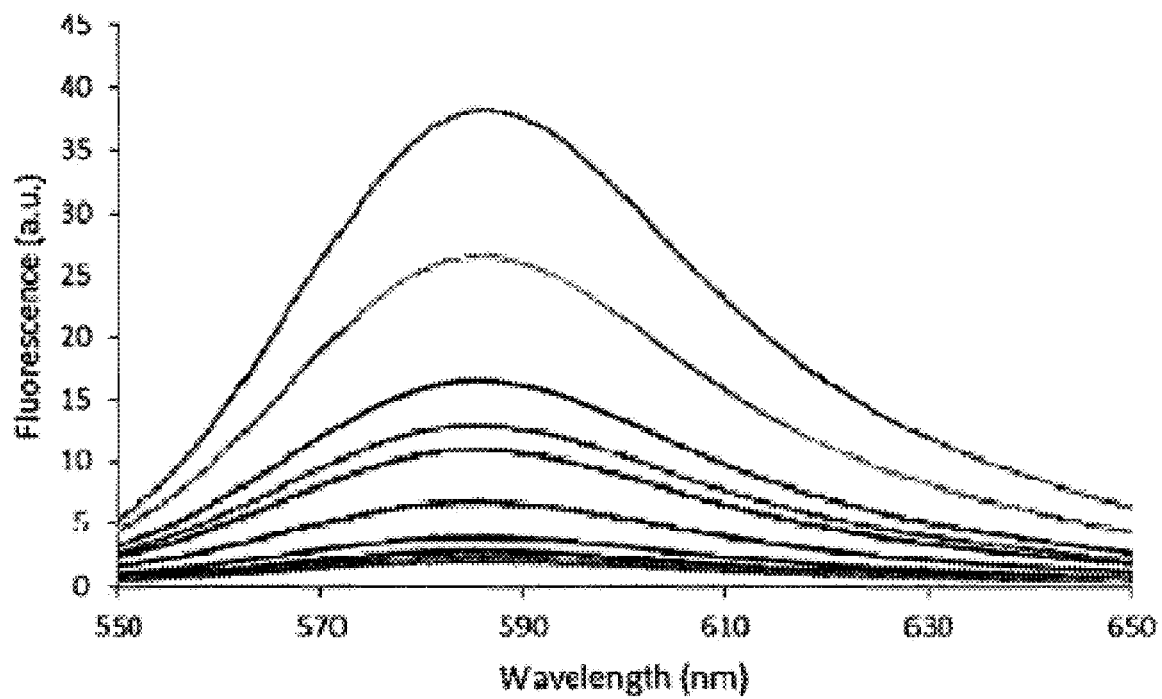
Figure 24A:
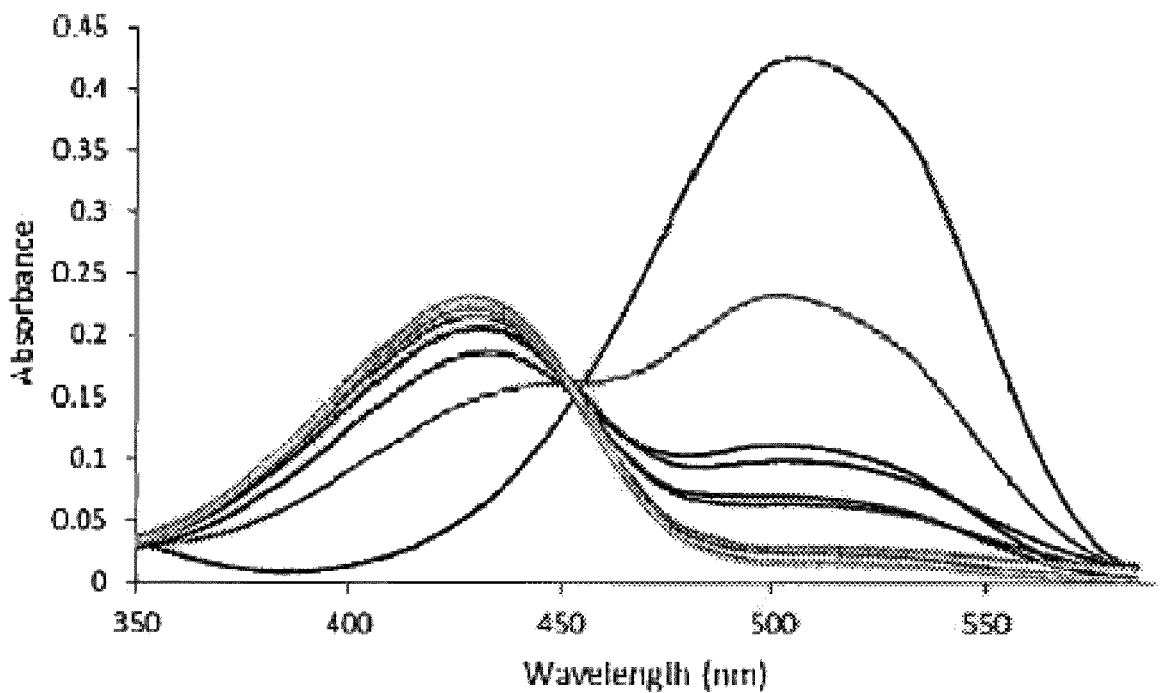
FIGS. 24a to 24c show the results of measuring the reversible reaction of the compound represented by formula 4 by the UV-Vis absorption spectrum (FIG. 24a), and show the fluorescence emission spectra (FIGS. 24b and 24c) obtained by measuring the reaction with the compound of formula 4 after equilibration with GSH (K d=2.8±0.4 mM).
Figure 24B:
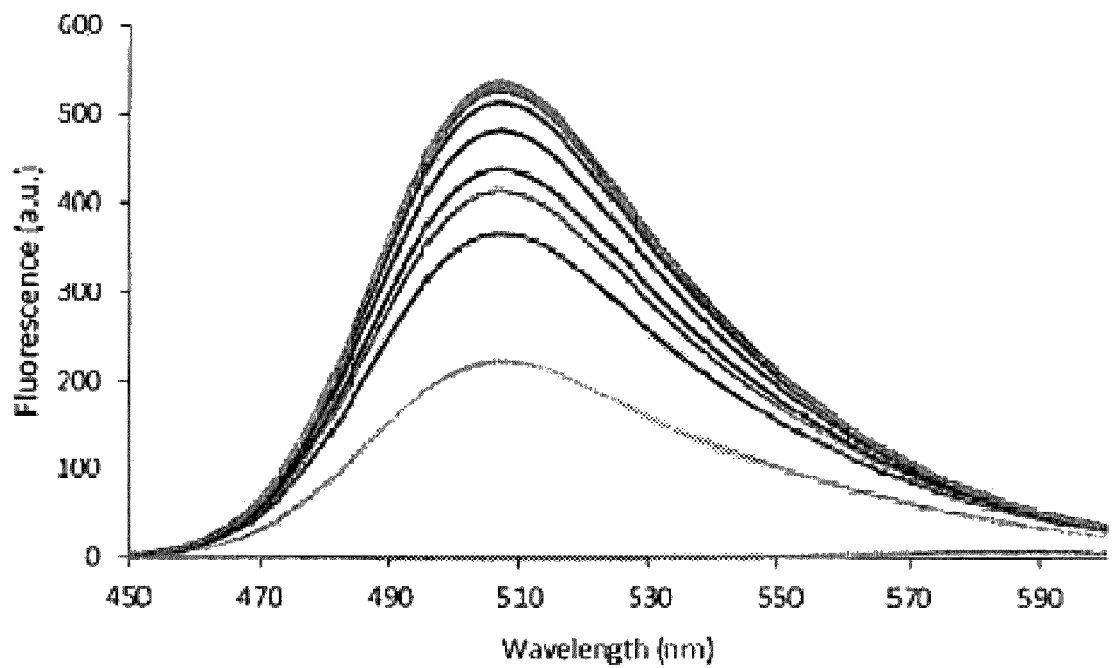
Figure 24C:
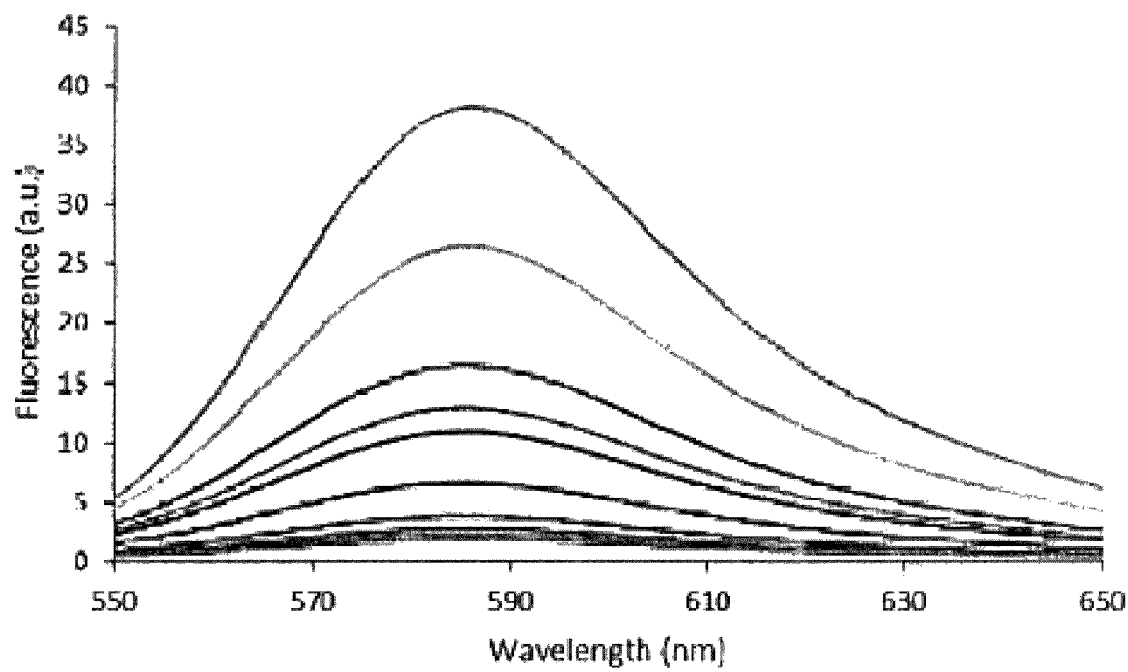
Figure 25A:
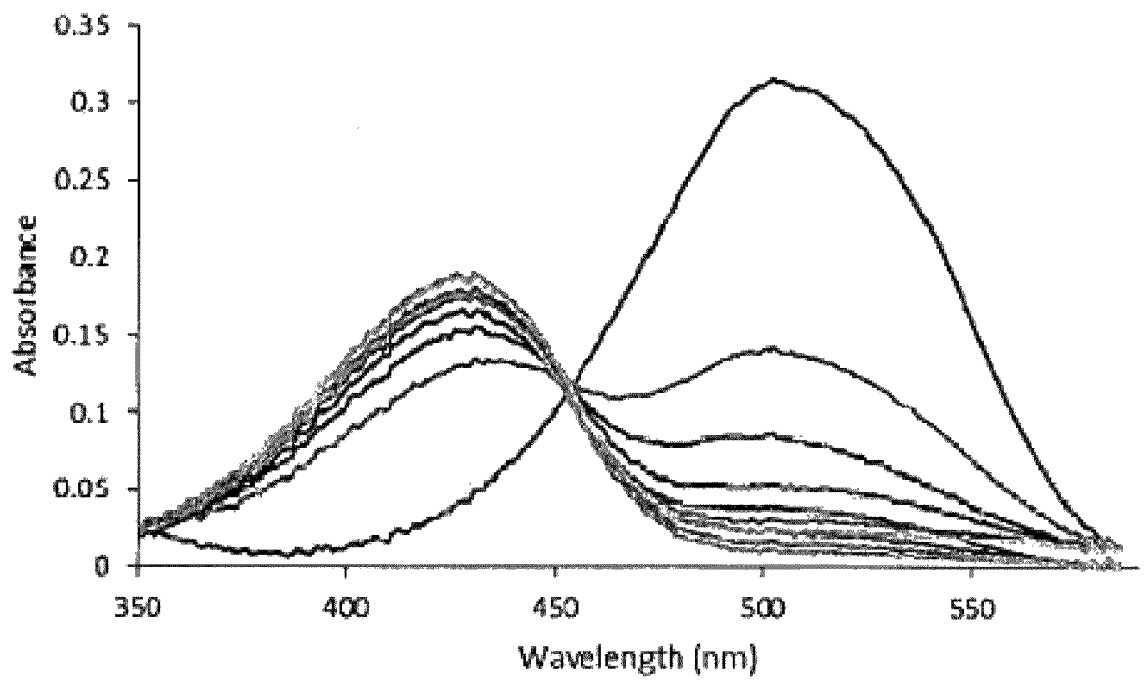
FIGS. 25a to 25c show the results of measuring the reversible reaction of the compound represented by formula 5 by the UV-Vis absorption spectrum (FIG. 25a), and show the fluorescence emission spectra (FIGS. 25b and 25c) obtained by measuring the reaction with the compound of formula 5 after equilibration with β-mercaptoethanol (Kd=2.2±0.1 mM).
Figure 25B:
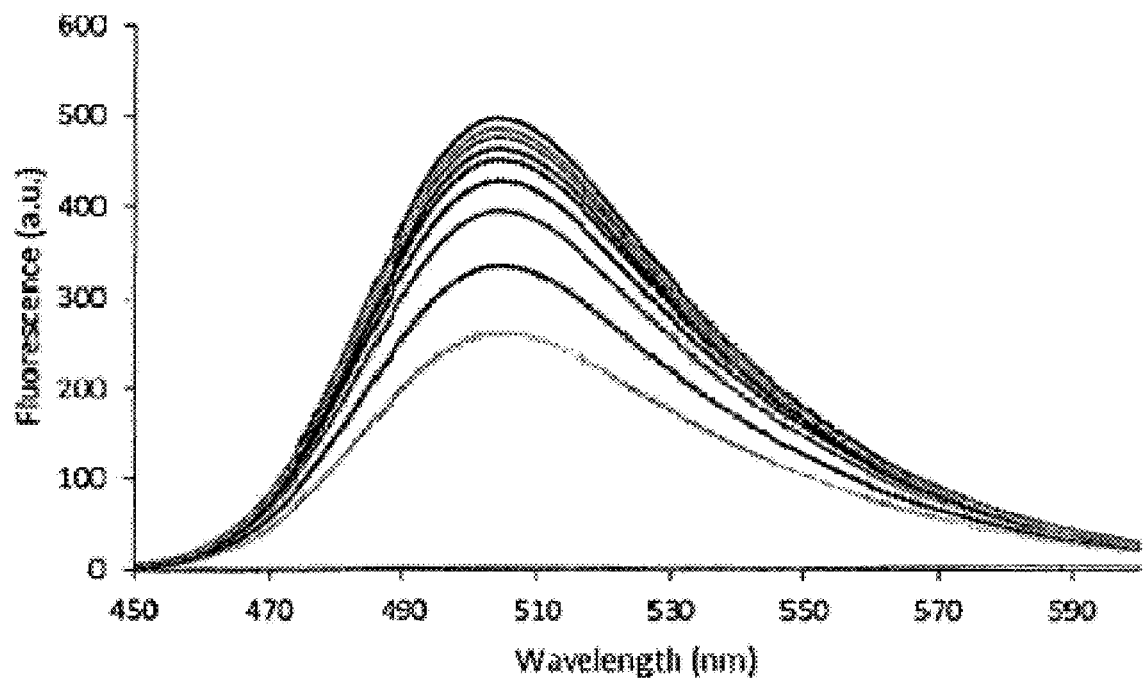
Figure 25C:
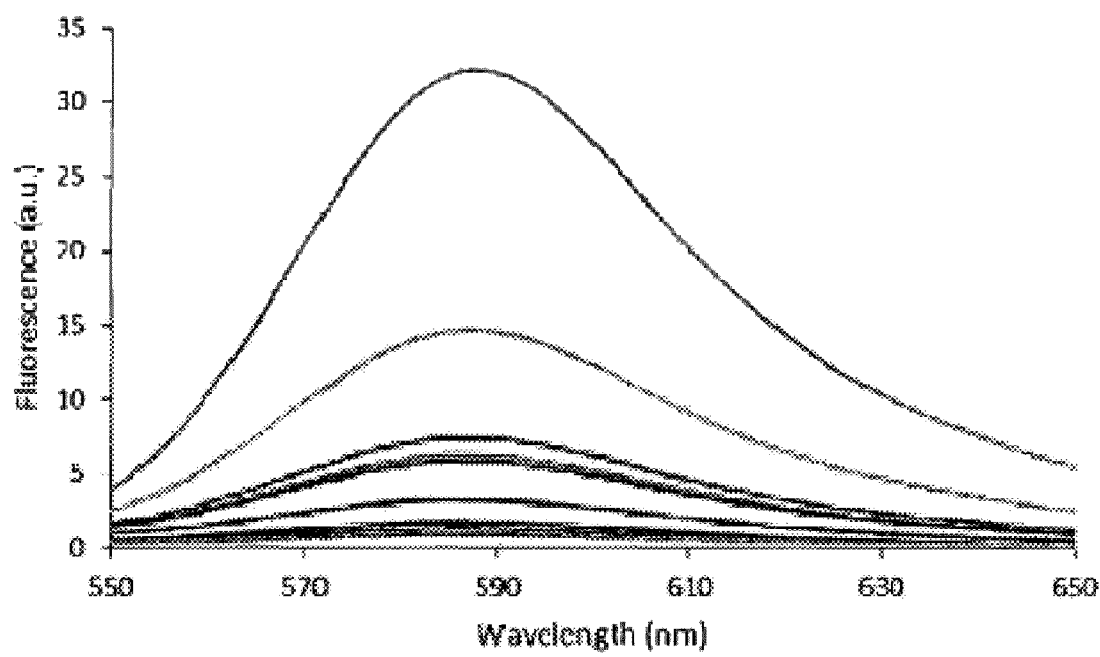
Figure 26A:
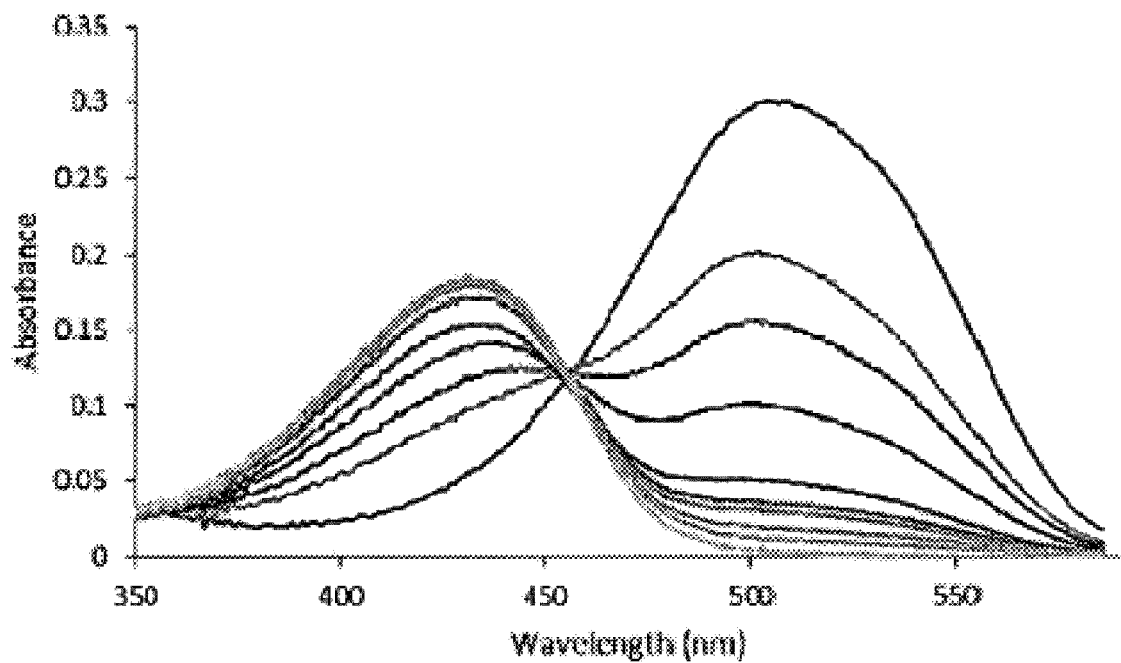
FIGS. 26a to 26c show the results of measuring the reversible reaction of the compound represented by formula 6 by the UV-Vis absorption spectrum (FIG. 26a), and show the fluorescence emission spectra (FIGS. 26b and 26c) obtained by measuring the reaction with the compound of formula 6 after equilibration with GSH (Kd=1.3±0.1 mM).
Figure 26B:
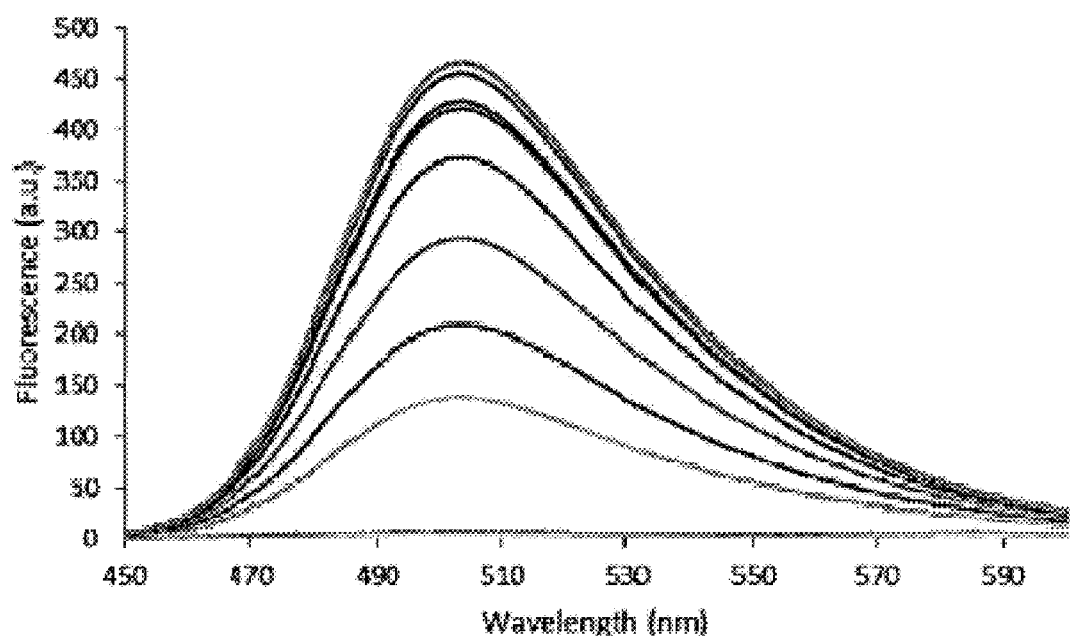
Figure 26C:
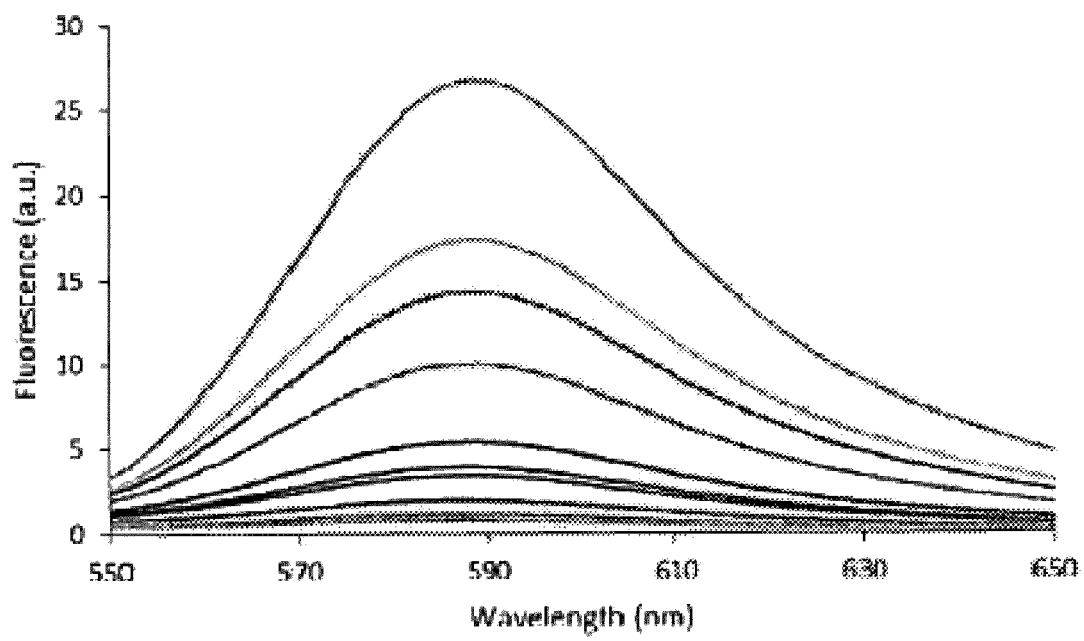
Figure 27A:
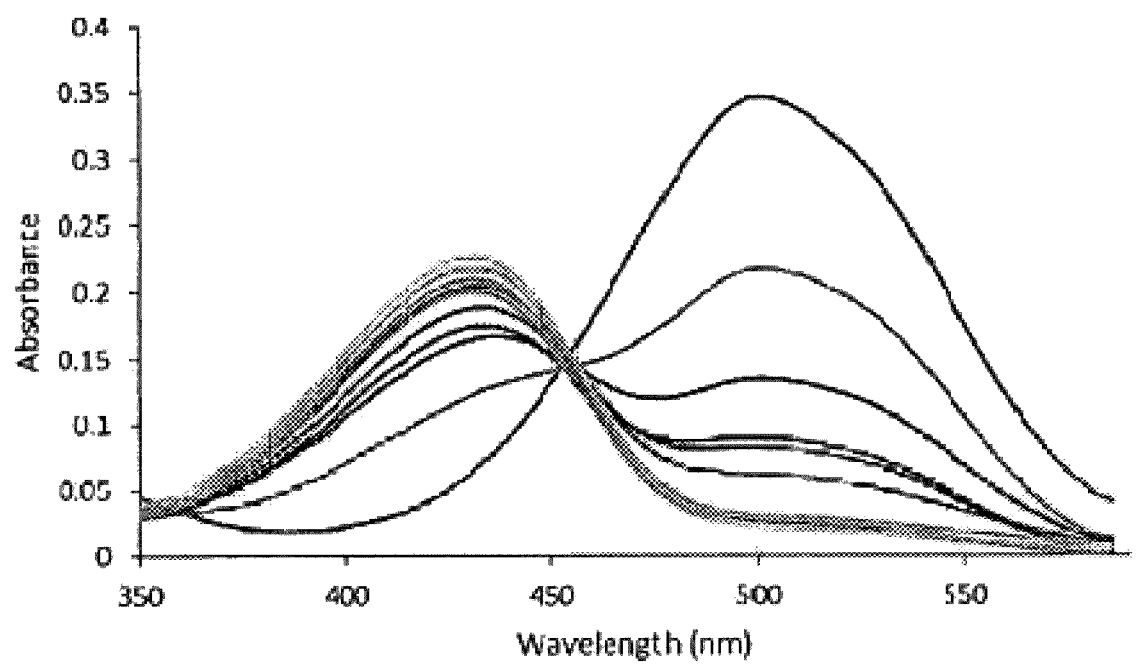
FIGS. 27a to 27c show the results of measuring the reversible reaction of the compound represented by formula 7 by the UV-Vis absorption spectrum (FIG. 27a), and show the fluorescence emission spectra (FIGS. 27b and 27c) obtained by measuring the reaction with the compound of formula 7 after equilibration with GSH (Kd=3.7±0.2 mM).
Figure 27B:
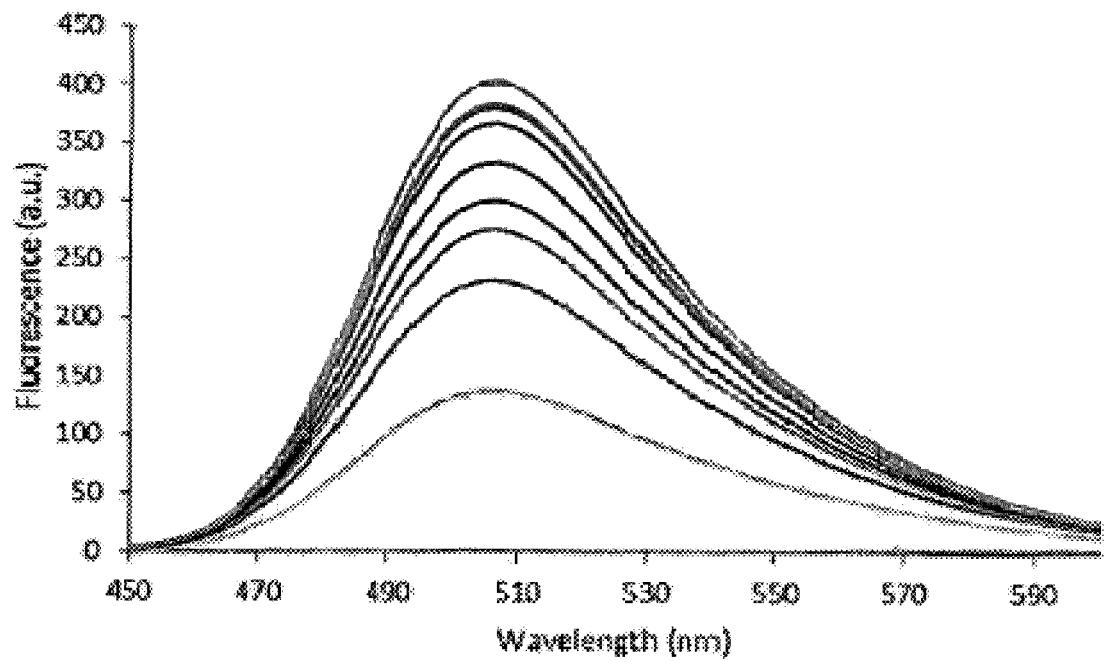
Figure 27C:
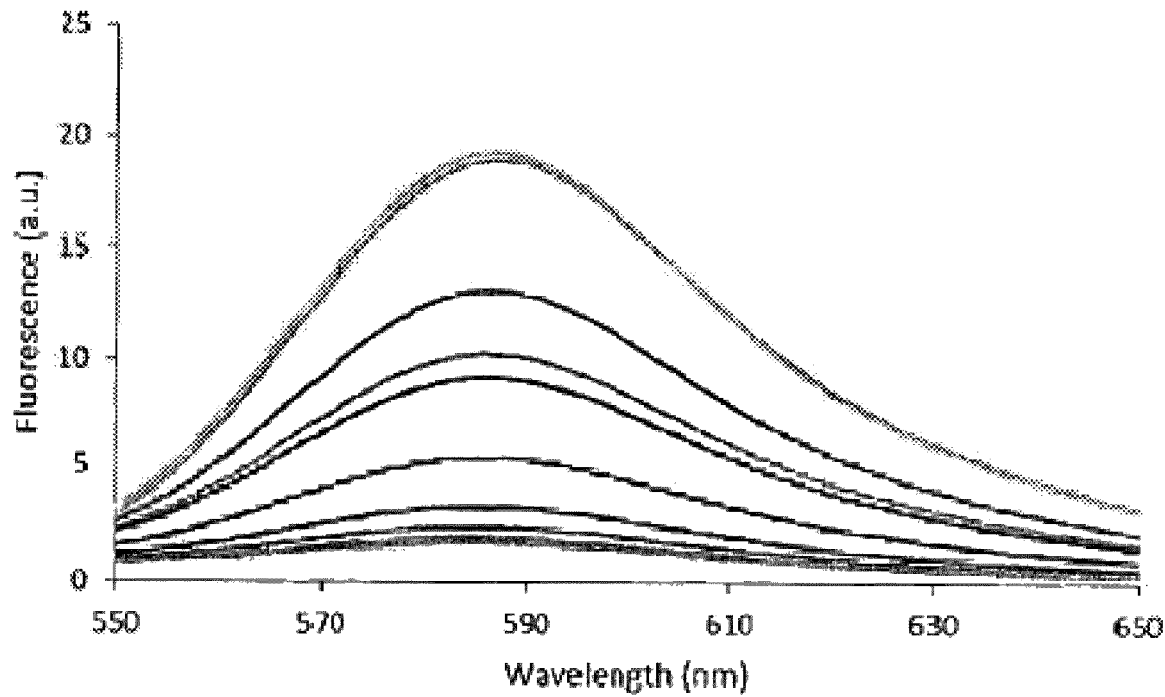
Figure 28A:
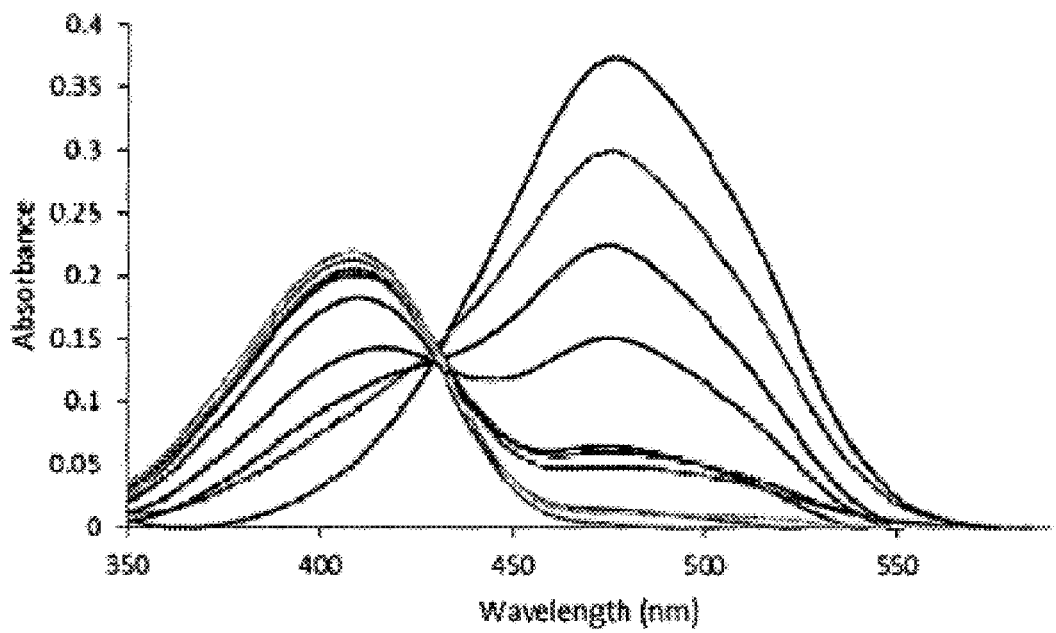
FIGS. 28a to 28c show the results of measuring the reversible reaction of the compound represented by formula 8 by the UV-Vis absorption spectrum (FIG. 28a), and show the fluorescence emission spectra (FIGS. 28b and 28c) obtained by measuring the reaction with the compound of formula 8 after equilibration with various concentrations of β-mercaptoethanol (Kd=2.2±0.1 mM).
Figure 28B:
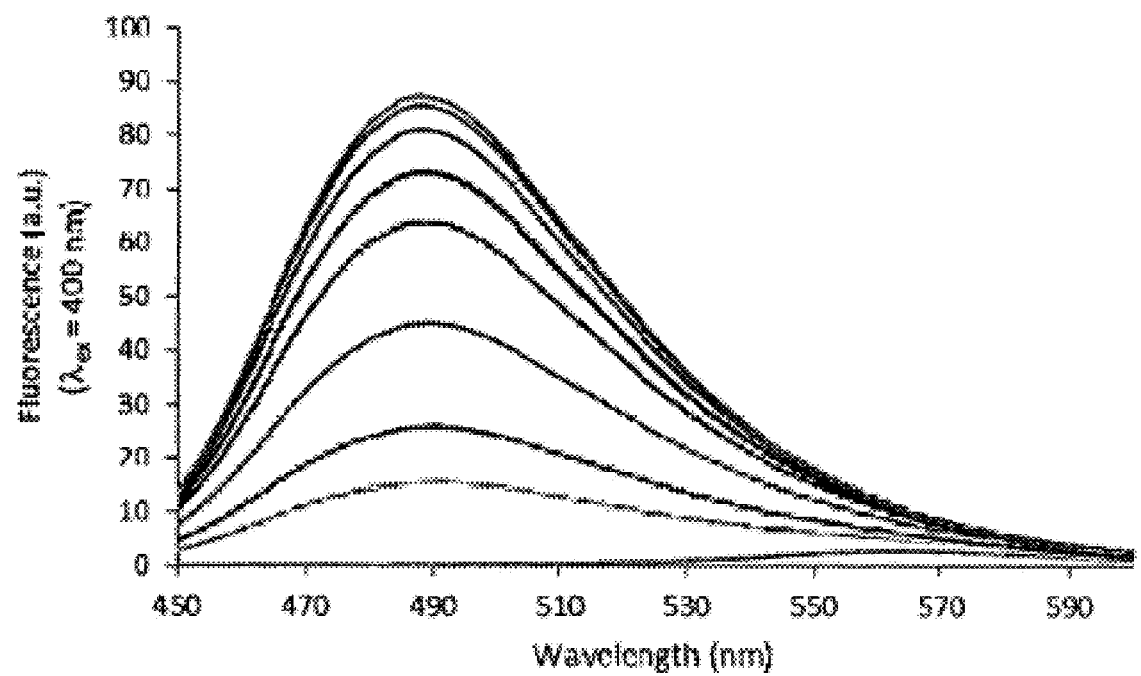
Figure 28C:
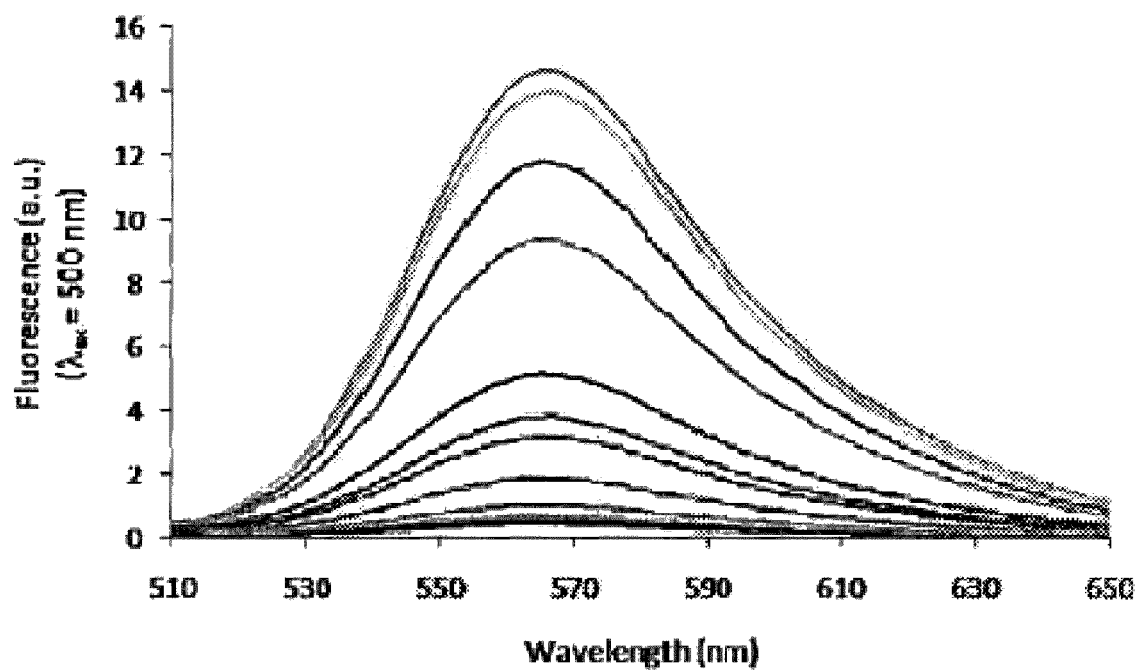

5. Observation of the Change in Intracellular Thiol Level with Change in Cell Culture Conditions The present inventors examined whether the FreSH-racer can also detect the intracellular thiol level that changed by intracellular reactive oxygen species (ROS). It is known that the generation of ROS in cells during cell culture changes depending on the density of the cells[3]. In the present invention, in order to examine whether the intracellular thiol level is also influenced by the cell density, HeLa cells were cultured at various densities, and then the cells were treated with the FreSH-tracer and analyzed using a microscope (FIG. 4a) and flow cytometry (FIGS. 20a and 20b). Using the two analysis techniques, the present inventors observed that there is a reproducible relationship between the cell density and the intracellular thiol level. It was found that, as the cell density in culture increases, the thiol level in the whole cell area including the cytoplasm and the nucleoplasm significantly increases.

Figure 4B:
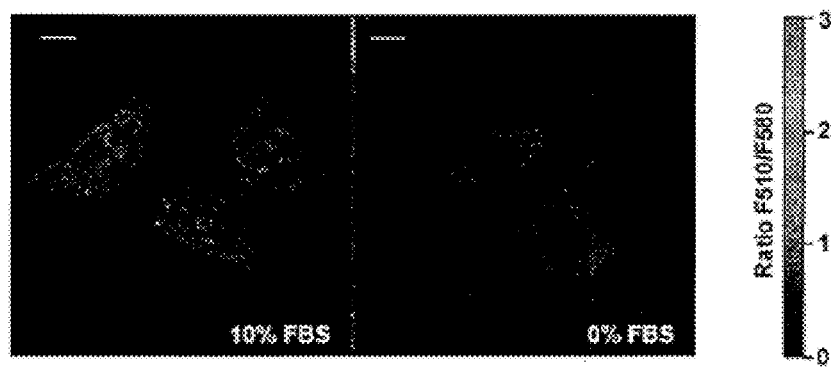
Figure 4B:
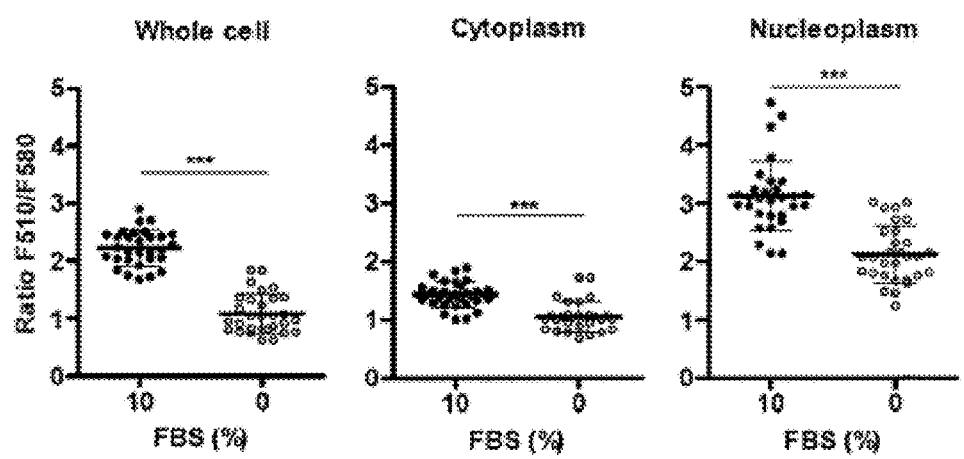

It is also well known that serum starvation in cell culture induces the generation of ROS in cells[4]. In the present invention, HeLa cells were cultured in a serum-containing or serum-starved growth medium, and the level of thiols in the cells was microscopically observed using the FreSH-tracer (FIG. 4b). As a result, the intracellular thiol level significantly decreased under the serum-starved conditions.

Taken together, the above experimental results demonstrated that the FreSH-tracer can be effectively used to analyze intracellular thiol levels that are controlled by intrinsic ROS.

6. Observation of Intracellular Thiol Levels that are Changed by ROS from NADPH Oxidase ROS that are generated by phagocytic NADPH oxidase (Phox) activity are essential defense substances that kill invasive microorganisms. It is known that the oxidation/reduction state of thiols in cells containing GSH and PSH are changed rapidly by Phox activation[5]. In the present invention, in order to activate the Phox of RAW264.4 macrophages loaded with the FreSH-tracer, the cells were treated with phorbol 12-myristate 13-acetate (PMA). The level of thiols in the cells was reduced by PMA treatment for 10-20 minutes and returned to the basal level after 40-50 minutes, whereas the cells treated with the carrier ethanol alone the initial thiol level (FIG. 5).

Taken together, the above experimental results demonstrated that the FreSH-tracer can be used as a biosensor for thiol levels in vitro and in vivo.

Although the present disclosure has been described in detail with reference to the specific features, it will be apparent to those skilled in the art that this description is only of a preferred embodiment thereof, and does not limit the scope of the present invention. Thus, the substantial scope of the present invention will be defined by the appended claims and equivalents thereof.

REFERENCES

1. Maher P. The effects of stress and aging on glutathione metabolism. *Ageing Res Rev.* 2005 May; 4(2):288-314.

2. Winterbourn CC1, Hampton M B., *Free Radic Biol Med.* 2008 Sep. 1; 45(5):549-61.

3. Pani, G. et al. A redox signaling mechanism for density-dependent inhibition of cell growth. *J. Biol. Chem.* 275, 38891-38899 (2000).

4. Satoh, T., Sakai, N., Enokido, Y., Uchiyama, Y. & Hatanaka, H. Survival factor-insensitive generation of reactive oxygen species induced by serum deprivation in neuronal cells. *Brain Res.* 733, 9-14 (1996).

5. Seres, T. et al. Protein S-thiolation and dethiolation during the respiratory burst in human monocytes. A reversible post-translational modification with potential for buffering the effects of oxidant stress. *J. Immunol.* 156, 1973-1980 (1996).

The invention claimed is:

1. A method for detection of recovering antioxidant activity in living cells, comprising a step of adding a composition comprising a compound selected from the group consisting of compounds represented by the following formulas 2 to 5, 7 and 8, or a salt thereof to the living cells, wherein the detection of recovering ability of antioxidant activity is performed by obtaining the ratio of the fluorescence intensity of the living cells at 430-550 nm to the fluorescence intensity at 550-680 nm:

[Formula 2]

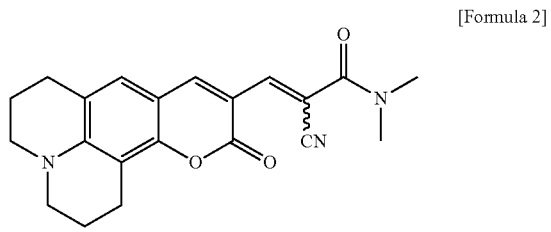

[Formula 3]

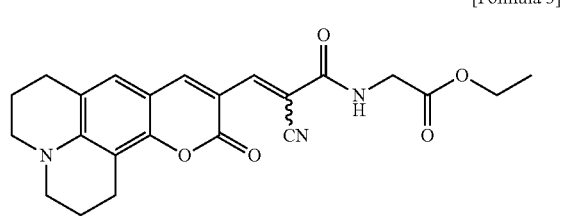

[Formula 4]

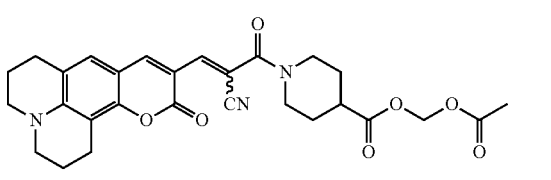

[Formula 5]

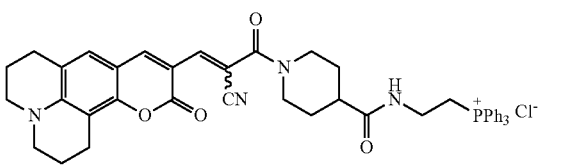

[Formula 7]

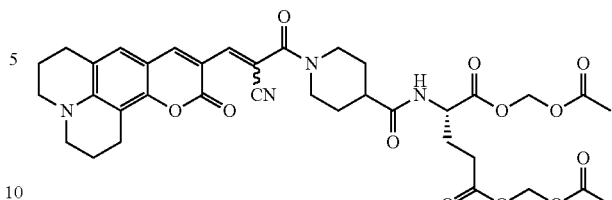

[Formula 8]

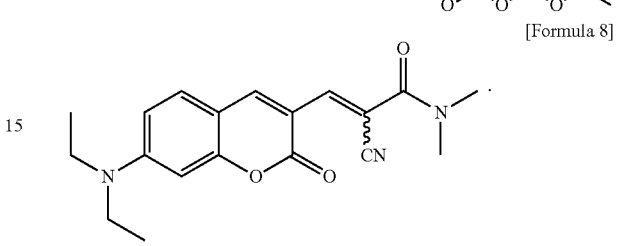

2. The method of claim 1, wherein the method further comprises the detection of a response of the living cells to an oxidative stress.

3. The method of claim 2, wherein the method comprises a step of detecting changes of the fluorescence intensity of the compounds of claim 1 at the emission wavelength as the amount of thiols in living cells increases or decreases.

4. The method of claim 3, fluorescence intensity at the emission wavelength changes in the range of 430 nm to 680 nm.

5. The method of claim 3 wherein the compound shows a decrease in the fluorescence intensity at 550-680 nm and an increase in the fluorescence intensity at 430-550 nm as the level of thiols in living cells increases.

6. The method of claim 1, wherein the ratio is a relationship between the fluorescence intensity at 430-550 nm and the fluorescence intensity at 550-680 nm.

7. The method of claim 6, wherein the relationship is a mathematical ratio between the fluorescence intensity at 430-550 nm and the fluorescence intensity at 550-680 nm, and the mathematical ratio changes ratio metrically and reversibly depending on the amount of thiols in living cells to thereby indicate the amount of thiols in living cells in real time.

8. The method of claim 1, wherein the detection is quantitative or qualitative detection of the thiols in the living cells.

9. The method of claim 1, wherein the detection is real-time quantitative detection.

10. The method of claim 3, wherein the thiols include glutathione (GSH), homocysteine (Hcy), cysteine (Cys), or thiols in cysteine residues of proteins.

11. The method of claim 1, wherein the method comprises the steps of:
   (a) measuring the ratio of the fluorescence intensity of the living cells at 430-550 nm to the fluorescence intensity at 550-680 nm;
   (b) adding the compounds of claim 1 to the living cells;
   (c) adding an oxidizing agent which induces oxidative stress to the living cells of step (b);
   (d) observing a change in the ratio of the fluorescence intensities of step (a);
   (e) after step (d), measuring the time for the ratio of the fluorescence intensities measured in the step (d) to return to the fluorescence intensity ratio intensity by comparing the ratio value of the fluorescence intensity measured in the step (a).

12. The method of claim 11, further comprising the step of determining that antioxidant activity is higher, when concentration of the composition in step (b) is lower, the concentration of oxidizing agent in step (c) is higher or the time in step (e) is shorter.

\* \* \* \* \*